(12) United States Patent
Reddy et al.

(10) Patent No.: US 7,598,232 B2
(45) Date of Patent: Oct. 6, 2009

(54) AMINO-SUBSTITUTED (E)-2,6-DIALKOXYSTYRYL 4-SUBSTITUTED-BENZYLSULFONES FOR TREATING PROLIFERATIVE DISORDERS

(75) Inventors: E. Premkumar Reddy, Villanova, PA (US); M. V. Ramana Reddy, Upper Darby, PA (US); Stanley C. Bell, Narberth, PA (US)

(73) Assignees: Temple University - Of the Commonwealth System of Higher Education, Philadelphia, PA (US); Onconova Therapeutics, Inc., Newtown, PA (US)

( * ) Notice: Subject to any disclaimer, the term of this patent is extended or adjusted under 35 U.S.C. 154(b) by 651 days.

(21) Appl. No.: 10/506,005

(22) PCT Filed: Feb. 28, 2003

(86) PCT No.: PCT/US03/06357

§ 371 (c)(1),
(2), (4) Date: Aug. 27, 2004

(87) PCT Pub. No.: WO03/072062

PCT Pub. Date: Sep. 4, 2003

(65) Prior Publication Data

US 2005/0130942 A1    Jun. 16, 2005

Related U.S. Application Data

(60) Provisional application No. 60/360,697, filed on Feb. 28, 2002.

(51) Int. Cl.
*A01N 57/00* (2006.01)
*A61K 31/66* (2006.01)

(52) U.S. Cl. .................. 514/114; 514/486; 514/618; 558/190; 560/16

(58) Field of Classification Search .......... 514/708, 514/601, 602, 603, 114, 486, 618; 564/84, 564/85, 86, 87, 88, 89, 90; 568/28; 530/402; 558/190; 560/16

See application file for complete search history.

(56) References Cited

U.S. PATENT DOCUMENTS

| | | | |
|---|---|---|---|
| 2,531,367 A | 11/1950 | Sprague | |
| 2,532,612 A | 12/1950 | Doumani | 260/609 |
| 3,185,743 A | 5/1965 | Combe et al. | 260/682 |
| 3,418,101 A | 12/1968 | Buchholtz et al. | 71/72 |
| 3,463,774 A | 8/1969 | Wilhelm et al. | 260/239.3 |
| 3,514,386 A | 5/1970 | Oswald et al. | 204/162 |
| 3,917,714 A | 11/1975 | Richmond | 260/607 A |
| 4,161,407 A | 7/1979 | Campbell | 96/114 |
| 4,258,058 A | 3/1981 | Witte et al. | 424/309 |
| 4,386,221 A | 5/1983 | Hyatt et al. | 568/28 |
| 4,937,388 A | 6/1990 | Bushell et al. | 568/56 |
| 5,659,087 A | 8/1997 | Aikins et al. | 568/27 |
| 5,733,909 A | 3/1998 | Black et al. | 514/238.8 |
| 5,780,483 A | 7/1998 | Widdowson et al. | 514/311 |
| 6,191,170 B1 | 2/2001 | Medina | 514/604 |
| 6,359,013 B1 | 3/2002 | Reddy et al. | 514/710 |
| 6,486,210 B2 * | 11/2002 | Reddy et al. | 514/708 |
| 6,541,475 B2 | 4/2003 | Reddy et al. | 514/252.12 |
| 6,548,553 B2 | 4/2003 | Reddy et al. | 514/710 |
| 6,586,617 B1 | 7/2003 | Tabuchi et al. | 558/394 |
| 6,599,932 B1 | 7/2003 | Reddy et al. | 514/438 |
| 6,646,009 B2 | 11/2003 | Reddy et al. | 514/604 |
| 6,656,973 B2 | 12/2003 | Cosenza et al. | 514/710 |
| 6,667,346 B2 | 12/2003 | Reddy et al. | 514/710 |
| 6,762,207 B1 | 7/2004 | Reddy et al. | 514/709 |
| 6,767,926 B1 | 7/2004 | Cosenza et al. | 514/710 |
| 6,787,667 B2 | 9/2004 | Reddy et al. | 562/429 |
| 7,053,123 B2 | 5/2006 | Reddy et al. | 514/710 |
| 7,056,953 B2 | 6/2006 | Reddy et al. | 514/710 |
| 7,161,031 B2 * | 1/2007 | Reddy et al. | 564/84 |
| 2005/0096484 A1 | 5/2005 | Reddy et al. | 564/92 |

FOREIGN PATENT DOCUMENTS

| | | |
|---|---|---|
| WO | WO95/24190 | 9/1995 |
| WO | WO96/40629 | 12/1996 |
| WO | WO 02/28828 | 4/2002 |

OTHER PUBLICATIONS

Balia et al., "Preparation & Absorption Spectra Of Some cis- & trans-αβ-Unsaturated Sulphides & Sulphones", *Indian J. Chem.* 9(3):220-5 (1971).

Kamigata et al., "Desulfonylation Of Arylmethane-Sulfonyl Chlorides Catalyzed By Dichlorotris(Triphenylphosphine)-Ruthenium(II)", *Phosphorous and Sulfur and the Related Elements* 20 (2): 139-44 (1984).

Reddy et al., "Preparation Of Styryl Benzylsulfones And 1,2-Bis-(Styrylsulfonymethyl)-4,5-Dimethylbenzenes", *Org. Prep. Proc. Int.*, 20(3):205-212 (1988).

CA:110:74956, abs of Reddy et al., "Preparation Of Styrl Benzyl Sulfones And 1,2-Bis(Styrylsulfonylmethyl)-4,5-Dimethylbenzenes", *Org Prep Proced Int*, 20(3) pp. 205-212 1988.

Reddy et al., "Synthesis And Cyclopropanataion Of (E)—And (Z)-Styryl Benzyl Sulfones", *Sulfur Lett.*, 13(2):83-90 (1991).

CA:126:185889, abs of Japanese Pat. App. 09-03,037 (Jan. 7, 1997).

Reddy and Reddy, "Synthesis Of α,β-Unsaturated Sulfones", *Acta Chim. Acad. Sci. Hung.*, 115(3):269-271 (1984).

Reddy et al., "Synthesis Of Some Novel α,β-Ethylenic Sulfones", *Phosphorus, Sulfur Silicon Relat. Elem.*, 60:209-214 (1991).

(Continued)

*Primary Examiner*—Karl J Puttlitz
*Assistant Examiner*—Chukwuma O Nwaonicha
(74) *Attorney, Agent, or Firm*—Daniel A. Monaco; Drinker Biddle & Reath LLP

(57) ABSTRACT

Compounds useful as antiproliferative agents, including, for example, anticancer agents, are provided according to formula (I); wherein: X, $X^1$, $X^2$, $R^a$, $R^1$, $R^2$, $R^3$, $R^4$, $R^5$, $R^6$, $R^7$, g, M, y, a, b, d, e, V, W, Z and Q are as defined herein.

122 Claims, 1 Drawing Sheet

OTHER PUBLICATIONS

Reddy and Reddy, "Synthesis And Spectral Studies Of Some (E)-α-[(Aryl)Sulfonyl]Chalcones", *Acta Chim. Acad. Sci. Hung.*, 120(4):275-280 (1985).

Reddy and Reddy, "A Novel Synthesis Of (E)-Substituted Styryl (Z)-Styryl Sulfones", *Synthesis* No. 4, 322-323 (1984).

Reddy et al., "A Facile Method For The Synthesis Of 2-(Arylsulfonyl)-1-Phenyl-3-Aryl-2-Propen-1-Ones", *Sulfur Lett.*, 7(2):43-48. (1987).

Reddy et al., "A New Route For The Synthesis Of Styrylbenzylsulfones, Precursors Of 1-Benzylsulfonyl-2-Arylcyclopropanes" *Phosphorus, Sulfur, and Silicon*, 53(1-4):285-290 (1990).

Makosza and Krylova, "Some Reactions Of The Chloromethyl Trans-β-Styryl Sulfone Carbanion", *Liebigs Ann./Recueil*, 2337-2340 (1997).

Reddy et al., "Phase Transfer Catalysis—A Facile Method For Cyclopropanation Of Some Isomeric Styryl Benzyl Sulfones And Bis(Styryl)Sulfones", *Acta Chim. Hung.*, 131(1):83-92 (1994).

CA:124:175763, abs of Reddy et al., "Syntheis Of 1,1-Disubstituted 2,6-Diaryl-4,4-Dioxides, Part II", *Indian J. Heterocycl. Chem.*, (1995), 5(1), 11-14.

CA:124:146025, abs of Reddy et al., "E, Z and E, E-Bis-(Styryl)Sulfones as Precursors for Thiane Oxides" *Indian J. Heterocycl. Chem.* (1995), 4(4), 259-264.

CA:126:166162, abs of Thompson et al., "Sulfone Metabolite Of Sulindac Inhibits Mammary Carcinogenesis", *Cancer Res.*, (1997) 57(2), 267-271.

Benati, et al., "Free-Radical Addition Of Alkanethiols To Alkynes. Rearrangements Of The Intermediate β-Thiovinyl Radicals", *J. Org. Chem.*, 59:2818-2823 (1994).

CA:120:323356, abs of Reddy et al., "Synthesis And Reactivity Of Some New Mono- And Bis(2-Pyrazolyl) Sulfones", *Sulf. Lett.* (1993), 16(5-6), 227-35.

CA:122:132682, abs of Reddy et al., "Stereospecific Synthesis Of Some New Z- And E-Cyclopropyl Benzyl Sulfones And E,Z- And E,E-Bix(Cyclopropyl) Sulfones By PTC Method", *Phosphorus, Sulfur Silicon Relat. Elem.* (1994), 90(1-4), 1-10.

CA:124:8731, abs of Reddy et al., "Tetrahydro-1,4-Thiazine-1, 1-Dioxides. Part Iv. Synthesis And Conformational Analysis Of Some 2,3,5-Trisubstituted Tetrahydro-1,4-Thiazine-1,1-Dioxides", *Indian J. Chem. Sect.B: Org. Chem. Incl. Med. Chem.* (1995) 34B(9), 816-22.

CA:76:121420, abs of Findlay et al. "Chemical Protectors Against Sunburn. Optical Evaluation, With Special Reference To P-Aminobenzoic Acid", *Brit. J. Dermatol., Suppl.* (1971), No. 7, 44-9.

CA:105:133446, abs of Naidu et al., "Synthesis Of Some New Bis-(Styryl)Sulfones", *Proc. Indian Acad. Sci., Chem Sci* (1985), 95(4), 391-5.

CA:132:263142, abs of Hillaire et al., "Cirrhosis", *Pathol. Biol.* (1999), 47(9), 895-902.

CA:130:336836, abs of Olson, "A Proposed Role For Nerve Growth Factor In The Etiology Of Multiple Sclerosis", *Med. Hypotheses* (1999), 51(6), 493-498.

CA:127:33922, abs of Evans and Taylor, "The Epoxy-Ramberg-Baecklund Reaction: A New Route To Allylic Alcohols", *Tetrahedron Lett.* (1997), 3055-3058.

CA:125:327911, abs of Riad et al., "Kinetics And Mechanism Of The Catalytic Reduction Of [[(4-Nitrophenyl)Methyl]Sulfonyl]Acetic Acid In Alkaline Dioxane-Water Media", *Egypt J. Chem.* (1996), 39(4), 353-364.

CA:120:210378, abs of Cheng and Hwang, "Metabolism Of 14c-Ring-Labeled Benthiocarb In Mice And Rats", *J. Chin. Biochem. Soc.* (1993), 22(1), 27-35.

CA:103:141088, abs of Janczewski and Ksiezopolski, "Effect Of Molecular Structure On Optical Properties Sulfoxide Systems. M-Bromobenzylsulfinylacetic Acids And Some Of Their Derivatives. Part VII", *Pol. J. Chem.* (1984), 58(1-2-3), 103-16.

CA:121:256180, abs of Li et al., "Synthesis And Pharmacological Evaluation Of Vinyl Sulfone Based Anticancer Agents", *Bioorg. Med. Chem. Lett.* (1994), 4(13), 1585-90.

Tanaka et al., "Structure Modifications Of S-*n*-Butyl S'*p-tert*-Butylbenzyl N-3-Pyridyldithiocarbonimidate (S-1358, Denmert®) And Fungicidal Activites", *Agric. Biol. Chem.* 41, 1953-1959, (1977).

CA:123:198103, abs of Riad et al., "Mechanism Of The Reaction Of Sodium Hydroxide And Nitrobenzylsulfones", *Egypt. J. Chem.* (1994) 37(2), 157-71.

Vedula et al., "Synthesis And Biological Evauation Of [4-(2-Phenylethylenesulfonylmethyl)Phenyl]-Quinazoline-4-Yl-Amines As Orally Active Anti-Cancer Agents", Bioorg. And Med. Chem. Lett, 14, (2004), pp. 67-71.

Vedula et al., "New Styryl sulfones as anticancer agents", European J. Med. Chem., 38 (2003), pp. 811-824.

Patent Abstracts of Japan, Abstract of JP04202173.

A. DeMilo, "Sulfonamide Insect Chemosterilants", *J. Agr. Food Chem.*, 1974, 22(2), 197-99.

C. R. A. Godfrey, et al., "A Novel Route to Unsymmetrical Stilbene Derivatives via Intramolecular Free Radical ipso Substitution Reactions", *Tetrahedron Lett.*, 1998, 39, 723-26.

*Chem. Abs.* 66:18556, abstracting S. Hartig, "Über einige Derivate der β-Styrolsulfonsäure", *Journal für praktische Chemie*, 1966, 33(3-4), 215-24.

S. Hartig, "Über einige Derivate der β-Styrolsulfonsäure", *Journal für praktische Chemie*, 1966, 33(3-4), 215-24.

*Chem. Abs.* 75:98861, abstracting G Manecke, et al., "Polymere Hydrochinosulfonamide", *Die Makromolekulare Chemie*, 1971, 145, 53-66.

G. Manecke, et al., "Polymere Hydrochinonsulfonamide", *Die Makromolekulare Chemie*, 1971, 145, 53-66.

K. Okuma, et al., "Reactions of (Aryloxy)oxosulfonium Ylides with Carbonyl Compounds", *J. Org. Chem.*, 1984, 49, 1402-07.

D. M. Purohit, et al., "Synthesis and Antimicrobial Activity of Sulfonamides, Imidazolinones, N', N"-Diarylphosphinic Amide Derivatives with Potent "Dichloran" Moiety", *Ind. J. Het. Chem.*, 1998, 8, 67-70.

W. E. Truce, et al., "Cyclopropanesulfonic Acid Esters and Amides", 1968, 33(10), 3849-51.

* cited by examiner

AMINO-SUBSTITUTED (E)-2,6-DIALKOXYSTYRYL 4-SUBSTITUTED-BENZYLSULFONES FOR TREATING PROLIFERATIVE DISORDERS

FIELD OF THE INVENTION

The invention relates to compositions and methods for the treatment of cancer and other proliferative disorders.

BACKGROUND OF THE INVENTION

Extracellular signals received at transmembrane receptors are relayed into the cells by the signal transduction pathways (Pelech et al., *Science* 257:1335 (1992)) which have been implicated in a wide array of physiological processes such as induction of cell proliferation, differentiation or apoptosis (Davis et al., *J. Biol. Chem.* 268:14553 (1993)). The Mitogen Activated Protein Kinase (MAPK) cascade is a major signaling system by which cells transduce extracellular cues into intracellular responses (Nishida et al., *Trends Biochem. Sci.* 18:128 (1993); Blumer et al., *Trends Biochem. Sci.* 19:236 (1994)). Many steps of this cascade are conserved, and peptides with considerable homology with MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., *Science* 255:212 (1992); Biggs III et al., *Proc. Natl. Acad. Sci. USA* 89:6295 (1992); Garner et al., *Genes Dev.* 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., *Genes Dev.* 7:2135 (1993)). JNKs are members of the class of stress-activated protein kinases (SPKs). JNKs have been shown to be activated by treatment of cells with UV radiation, pro-inflammatory cytokines and environmental stress (Derijard et al., *Cell* 1025 (1994)). The activated JNK binds to the amino terminus of the c-Jun protein and increases the protein's transcriptional activity by phosphorylating it at ser63 and ser73 (Adler et al., *Proc. Natl. Acad. Sci. USA* 89:5341 (1992); Kwok et al., *Nature* 370:223 (1994)).

Analysis of the deduced primary sequence of the JNKs indicates that they are distantly related to ERKs (Davis, *Trends Biochem. Sci.* 19:470 (1994)). Both ERKs and JNKs are phosphorylated on Tyr and Thr in response to external stimuli resulting in their activation (Davis, *Trends Biochem. Sci.* 19:470 (1994)). The phosphorylation (Thr and Tyr) sites, which play a critical role in their activation are conserved between ERKs and JNKs (Davis, *Trends Biochem. Sci.* 19:470 (1994)). However, these sites of phosphorylation are located within distinct dual phosphorylation motifs: Thr-Pro-Tyr (JNK) and Thr-Glu-Tyr: (ERK). Phosphorylation of MAPKs and JNKs by an external signal often involves the activation of protein tyrosine kinases (PTKs) (Gille et al., *Nature* 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., *Annu Rev Biochem* 54:897 (1985)). Receptor tyrosine kinases in: particular are attractive targets for drug design since blockers for the substrate domain of these kinases is likely to yield an effective and selective antiproliferative agent The potential use of protein tyrosine kinase blockers as antiproliferative agents was recognized as early as 1981, when quercetin was suggested as a PTK blocker (Graziani et al., *Eur. J. Biochem.* 135:583-589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription. factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What are also needed are new cell antiproliferative agents, and anticancer therapeutics in particular, which are highly selective in the killing of proliferating cells such as tumor cells, but not normal cells.

SUMMARY OF THE INVENTION

It is an object of the invention to provide compounds, compositions and methods for the treatment of cancer and other proliferative diseases. The biologically active compounds are in the form of substituted styryl benzylsulfones.

It is an object of the invention to provide compounds which are selective in killing tumor cells but not normal cells.

According to one embodiment, compounds of the invention have the formula I

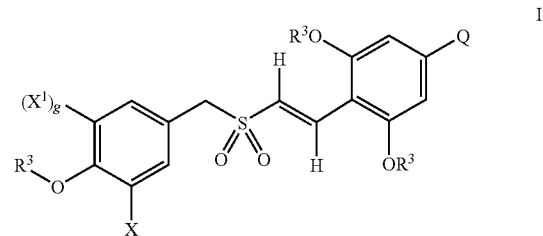

wherein:
X is selected from the group consisting of (i) and (ii) below:

$X^1$ is selected from the group consisting of (i), (ii) and (iii) below:

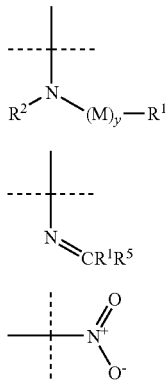

wherein $X^1$ is optionally protected with one or more chemical protecting groups;

g is 0 or 1;

each M is a bivalent connecting group independently selected from the group consisting of —$(C_1\text{-}C_6)$alkylene-, —$(CH_2)_a$—V—$(CH_2)_b$—, —$(CH_2)_d$—W—$(CH_2)_e$— and -Z-;

each y is independently selected from the group consisting of 0 and 1;

each V is independently selected from the group consisting of arylene, heteroarylene, —C(=O)—, —C(=S)—, —S(=O)—, —$SO_2$—, —C(=O)O—; —C(=O)$(C_1\text{-}C_6)$perfluoroalkylene-, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

-Z- is

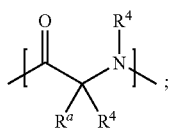

wherein the absolute stereochemistry of -Z- is D or L or a mixture of D and L;

each $R^a$ is independently selected from the group consisting of —H, —$(C_1\text{-}C_6)$alkyl, —$(CH_2)_3$—NH—C$(NH_2)$(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$—(2-imidazolyl), —CH$(CH_3)$—$CH_2$—$CH_3$, —$CH_2$CH$(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH$(CH_3)_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$, —$(C_1\text{-}C_6)$perfluoroalkyl, —$CF_2$Cl, —P(=O)$(OR^4)_2$, —OP(=O)$(OR^4)_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —$(C_1\text{-}C_6)$alkyl, and aryl$(C_1\text{-}C_3)$alkyl, wherein —$R^2$ and -$(M)_y$-$R^1$ may optionally be linked covalently to form a 5-, 6- or 7-membered substituted or unsubstituted heterocycle;

each $R^3$ is independently selected from —$(C_1\text{-}C_6)$alkyl;

each $R^4$ is independently selected from the group consisting of —H, and —$(C_1\text{-}C_6)$alkyl;

wherein:
when $R^4$ and $R^1$ are bonded to the same nitrogen atom, $R^1$ and $R^4$ may combine to form a heterocycle; and
when two $R^4$ groups are geminally bonded to the same nitrogen, the two $R^4$ groups may combine to form a heterocycle;

each $R^5$ is independently selected from the group consisting of —H, —$(C_1\text{-}C_6)$alkyl and —$(C_1\text{-}C_6)$acyl;

each $R^6$ is independently selected from the group consisting of —H, —$(C_1\text{-}C_6)$alkyl, —$CO_2R^5$, —C(=O)$R^7$, —$OR^5$, —OC(=O)$(CH_2)_2CO_2R^5$, —$SR^4$, guanidino, —$NR^4_2$, —$N^+R^4_3$, —$N^+(CH_2CH_2OH)_3$, phenyl, substituted phenyl, heterocyclic, substituted heterocyclic and halogen;

each $R^7$ is independently selected from the group consisting of —H, —$R^a$, halogen, —$(C_1\text{-}C_6)$alkyl, —$NR^4_2$ and heterocycles containing two nitrogen atoms; and Q is selected from the group consisting of —H, —$(C_1\text{-}C_6)$alkoxy, halogen, —$(C_1\text{-}C_6)$alkyl and —$NR^4_2$;

wherein the substituents for the substituted aryl and substituted heterocyclic groups comprising or included within $R^1$, $R^a$, $R^2$, $R^6$ and $R^7$, are independently selected from the group consisting of halogen, $(C_1\text{-}C_6)$alkyl, $(C_1\text{-}C_6)$alkoxy, —$NO_2$, —C≡N, —$CO_2R^5$, —C(=O)O$(C_1\text{-}C_3)$alkyl, —$OR^5$, —$(C_2\text{-}C_6)$alkylene-OH, phosphonato, —$NR^4_2$, —NHC(=O)$(C_1\text{-}C_6)$alkyl, sulfamyl, —OC(=O)$(C_1\text{-}C_3)$alkyl, —O$(C_2\text{-}C_6)$alkylene-N$((C_1\text{-}C_6)$alkyl$)_2$ and —$CF_3$;

provided
(1) when $R^1$ is a monovalent peptidyl moiety of molecular weight less than 1000 and V is —C(=O)—, —C(=S)—, —S(=O)— or —$SO_2$—, and b is 0;
then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)$NR^4$— or —$SO_2NR^4$—, and b is 0,
then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —$NR^4$—, —S— or —O—, and e is 0,
then said pepfidyl moiety is coupled to M through the carboxy terminus of the peptidyl moiety or through a sidechain carboxyl group to form a carboxamide, carbothioic acid ester or carboxylic ester respectively;

or a salt of such a compound.

According to one sub-embodiment thereof, there are provided compounds of formula I, wherein:

each V is independently selected from the group consisting of —C(=O)—, —C(=S)—, —S(=O)—, —O$_2$—; —C(=O)NR$^4$—, —C(=S)NR$^4$— and —SO$_2$NR$^4$—;

-Z- is

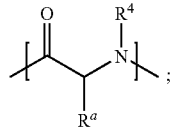

wherein the absolute stereochemistry of -Z- is either D or L each R$^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein R$^a$ and R$^1$ combine to form a 5-, 6- or 7-membered heterocyclic ring;

each R$^1$ is independently selected from the group consisting of —H, unsubstituted aryl, substituted aryl, substituted heterocyclic, unsubstituted heterocyclic, —CO$_2$R$^5$, —C(=O)NR$^4$$_2$, —CHR$^6$R$^7$, —C(=NH)—NR$^4$$_2$, and a monovalent peptidyl moiety with a molecular weight of less than 1000; provided that when y is 0 and R$^1$ is O$_2$R$^5$, R$^5$ is not —H;

each R$^6$ is independently selected from the group consisting of —H, —(C$_1$-C$_6$)alkyl, O$_2$R$^5$, —C(=O)R$^7$, —OH, —SR$^4$, —(C$_1$-C$_3$)alkoxy, —(C$_1$-C$_3$)alkylthio, guanidino, —NR$^4$$_2$, phenyl, substituted phenyl, heterocyclic, substituted heterocyclic and halogen; and each R$^7$ is independently selected from the group consisting of —H, halogen, —(C$_1$-C$_6$)alkyl, —NR$^4$$_2$ and heterocycles containing two nitrogen atoms;

wherein the substituents for the substituted aryl and substituted heterocyclic groups comprising or included within R$^1$, R$^a$, R$^2$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$.

According to a preferred sub-embodiment, there are provided compounds of formula I, wherein each V is independently selected from the group consisting of

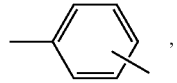

—C(=O), —C(=S, (=O)—, —SOs, C(=O)O—; —C(=O)NR$^4$—, —C(=S)NR$^4$— and —SO$_2$NR$^4$—.

According to a more preferred sub-embodiment thereof, there are provided compounds of formula I, wherein each V is independently selected from the group consisting of

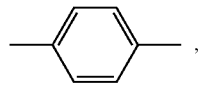

—C(=O)—, —C(=S)—, —S(=O)—, —SO$_2$—, —C(=O)O—; —C(=O)NR$^4$—, —C(=S)NR$^4$— and —SO$_2$NR$^4$—.

According to another sub-embodiment thereof, there are provided compounds of formula I, wherein Z has an L absolute configuration.

Preferred compounds of formula I, include for example, the following compounds and salts thereof:

(E)-2,4,6-trimethoxystyryl-3-[4-(4-methylpiperazin-1-yl] benzamido)-4-methoxybenzylsulfone;

(E)-2,4,6-trimethoxystyryl-3-(acetoxyacetamido)-4-methoxy-benzylsulfone;

(E)-2,4,6-tnimethoxystyryl-3-(triethylammoniumacetamido)-4-methoxybenzylsulfone;

(E)-2,4,6-trimethoxystyryl-3-[tri-(2-hydroxyethylammonium)acetamido]-4-methoxybenzylsulfone;

(E)-2,4,6-trimethoxystyryl-3-(2-methyl-2-hydroxypropionamido)-4-methoxybenzylsulfone;

(E)-2,4,6-trimethoxystyryl-3-(2-methyl-2-acetoxypropionamido)-4-methoxybenzylsulfone;

(E)-2,4,6-trimethoxystyryl-3-(2-acetoxypropionamido)-4-methoxybenzylsulfone;

(E)-2,4,6-trimethoxystyryl-3-(trifluoroacetamido)-4-methoxybenzylsulfone;

(E)-2,4,6-trimethoxystyryl-3-(trifluoromethanesulfonamido)-4-methoxybenzylsulfone;

(E)-2,4,6-trimethoxystyryl-3-[3-(3-carboxypropanoyloxy) acetamido]-4-methoxybenzylsulfone;

(E)-2,4,6-trimethoxystyryl-3-(phosphonatoacetamido)-4-methoxybenzylsulfone, disodium salt;

(E)-2,4,6-trimethoxystyryl-3-(methylcarbamoyl)-4-methoxybenzylsulfone;

(E)-2,4,6-trimethoxystyryl-3-(2,2-difluoromalonamido)-4-methoxybenzylsulfone;

(E)-2,4,6-trimethoxystyryl-3-(pentafluoropropionamido)-4-methoxybenzylsulfone;

(E)-2,4,6-trimethoxystyryl-3-(methyl-2,2-difluoromalonamido-4-methoxybenzylsulfone;

(E)-2,4,6-trimethoxystyryl-3-(2,2-difluoromalonamido)-4-methoxybenzylsulfone;

(E)-2,4,6-trimethoxystyryl-3-(dimethylamino-α,α-difluoroacetamido)-4-methoxybenzylsulfone; and (E)-2,4,6-trimethoxystyryl-3-(2,2,3,3,tetrafluorosuccinamido)-4-methoxybenzylsulfone.

According to a first embodiment of the invention of formula I, x is

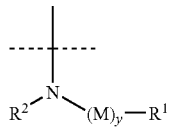

(i)

and y is 0; and R$^2$ is —H.

According to a sub-embodiment, there are provided compounds of the formula III, below:

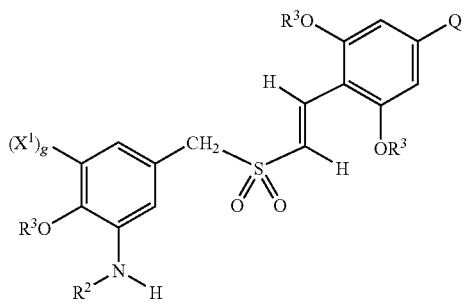

wherein:

g is 0 or 1;

each $R^2$ is independently selected from the group consisting of —H, —$(C_1-C_6)$alkyl, and aryl$(C_1-C_3)$alkyl, wherein —$R^2$ and -$(M)_y$-$R^1$ may optionally be linked covalently to form a 5-, 6- or 7-membered substituted or unsubstituted heterocycle;

each $R^3$ is independently selected from —$(C_1-C_6)$alkyl;

each $R^4$ is independently selected from the group consisting of —H, and —$(C_1-C_6)$alkyl;

Q is selected from the group consisting of —H, —$(C_1-C_6)$alkoxy, halogen, —$(C_1-C_6)$alkyl and —$NR^4_2$; and $X^1$ is selected from the group consisting of (i), (ii) and (iii) below:

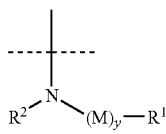

(i)

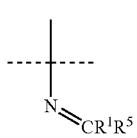

(ii)

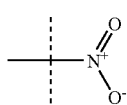

(iii)

wherein $X^1$ is optionally protected with one or more chemical protecting groups;

Suitable protecting groups will be stable to reactions designed to derivatize the 3-amino group of formula III. Subsequently, said protecting groups are optionally removed to regenerate the $X^1$.

In another sub-embodiment, there are provided compounds of the formula IIIa, below:

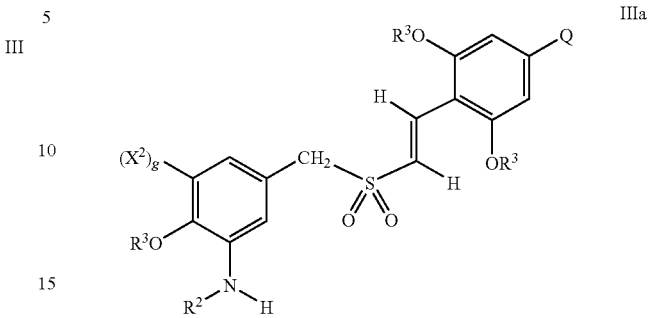

wherein $X^2$ is selected from the group consisting of —$NO_2$ and —$NH_2$, wherein said —$NH_2$ is optionally protected with a chemical protecting group.

The strategy for synthesizing compounds of formula I involves derivatization of a primary or secondary amino group at the 3-position of formula IIIa. Such derivatizations of the 3-amino group include, for example, reactions to form carboxamides, sulfonamides alkyl amines, nitrogen-containing heterocycles, imines, guanidines, ureas, amidines, and amino ketones.

The intermediate of formula IIIa also incorporates a nitro group or a protected amino group at the 5-position. In the synthetic strategy, this 5-substituent serves as a second, latent amino group. The use of this protecting group strategy allows for differential derivatization of these two amino groups, i.e., the 3-amino group of formula IIIa and the moiety at the 5-position which is inert to the conditions of the derivatization of the 3-amino group. Hence, the synthetic route involves first derivatizing the 3-amino group, followed by conversion of the 5-substituent to an amino group via either (a) deprotection, if $X^2$ is a protected amine, or (b) chemical reduction if $X^2$ is a nitro group. Hence, from a retrosynthetic viewpoint, the synthetic route allows for differential derivatization of two amino groups, one at the 5-position which is protected (either with a chemical protecting group, or by being in a nitro oxidation state) and thereby inert to the conditions of the derivatization of the 3-amino group. Suitable chemical protecting groups for the 5-position protected amine, include for example, benzyl, 2,4-dimethoxy-benzyl and benzyloxycarbonyl (CBZ). In a similar manner, when $X^2$ is —$NO_2$, the 3-amino group may be derivatized in the aforesaid manner. Subsequently the —$NO_2$ group may optionally be chemically reduced to the corresponding 5-amino group via a variety of procedures known to those skilled in the art.

Subsequently, the 5-amino group, generated by either reduction of a 5-nitro group or by removing a protecting group from a protected 5-amino compound, is optionally derivatized. Derivatization of the 5-amino group may be the same or different from the derivatization of the 3-amino group.

According to a sub-embodiment of the aforesaid compounds of formula IIIa, compounds are provided wherein Q is —$(C_1-C_6)$alkoxy.

According to another sub-embodiment of formula IIIa, Q is —$OCH_3$.

According to a further sub-embodiment of formula IIIa, $R^3$ is —$CH_3$. One such compound is (E)-2,4,6-trimethoxystyryl-4-methoxy-3-amino-benzylsulfone.

According to a second embodiment of the invention of formula I,
X is

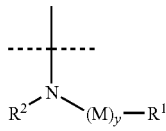

and $R^2$ is —H, y is 0, and
$R^1$ is selected from the group consisting of unsubstituted aryl, substituted aryl, substituted heterocyclic, unsubstituted heterocyclic, —$CO_2R^5$, —C(=O)$NR^4_2$, —$CHR^6R^7_1$, —C(=NH)—$NR^4_2$ and a monovalent peptidyl moiety with a molecular weight of less than 1000.

According to a third embodiment of the invention of formula I,
X is

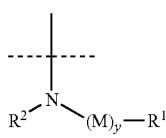

and y is 1; M is —$(CH_2)_a$—V—$(CH_2)_b$—; and V is —C(=O)—.

According to a sub-embodiment thereof, compounds of the formula IV, below and salts thereof, are provided:

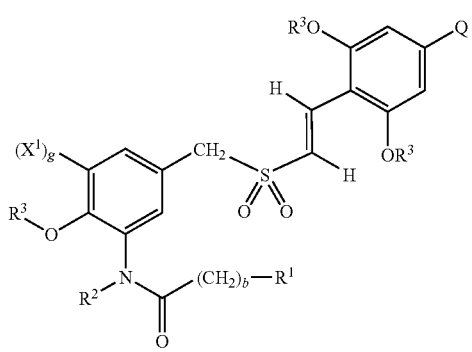

Preferred compounds of formula IV, include for example, the following compounds and salts thereof:
(E)-2,4,6-trimethoxystyryl-3-(carboxyacetamido)-4-methoxybenzylsulfone;
(E)-2,4,6-tnimethoxystyryl-3-(3,5-dinitrobenzamido)-4-methoxybenzylsulfone;
(E)-2,4,6-trimethoxystyryl-3-(3,5-diaminobenzamido)-4-methoxybenzylsulfone;
(E)-2,4,6-trimethoxystyryl-3-(chloroacetamido)-4-methoxybenzylsulfone;
(E)-2,4,6-trimethoxystyryl-3-[(4-methylpiperazinyl)acetamido]-4-methoxybenzylsulfone;
(E)-2,4,6-trimethoxystyryl-3-(benzamido)-4-methoxybenzylsulfone;
(E)-2,4,6-trimethoxystyryl-3-(4-nitrobenzamido)-4-methoxybenzylsulfone;
(E)-2,4,6-trimethoxystyryl-3-(4-aminobenzamido)-4-methoxybenzylsulfone;
(E)-2,4,6-trimethoxystyryl-3-(acetamido)-4-methoxybenzylsulfone;
(E)-2,4,6-trimethoxystyryl-3-(dimethylaminoacetamido)-4-methoxybenzylsulfone;
(E)-2,4,6-trimethoxystyryl-3-(hydroxyacetamido)-4-methoxy-enzylsulfone;
(E)-2,4,6-tnimethoxystyryl-3-(2-hydroxypropionamido)-4-methoxybenzylsulfone
(E)-2,4,6-trimethoxystyryl-3-(pyridinium-1-yl)acetamido-4-methoxybenzylsulfone;
(E)-2,4,6-trimethoxystyryl-3-(ethylmalonamido)-4-methoxy-benzylsulfone;
(E)-2,4,6-trimethoxystyryl-3-(glutaramido)-4-methoxybenzylsulfone
(E)-2,4,6-trimethoxystyryl-3-(methylsuccinamido)-4-methoxybenzylsulfone;
(E)-2,4,6-trimethoxystyryl-3-(succinamido)-4-methoxybenzylsulfone;
(E)-2,4,6-trimethoxystyryl-3-(3-chlorosuccinamido)-4-methoxybenzylsulfone; and
(E)-2,4,6-trimethoxystyryl-3-(aminoacetamido)-4-methoxybenzylsulfone;
or a salt of such a compound.

According to a fourth embodiment of the invention of formula I; X is

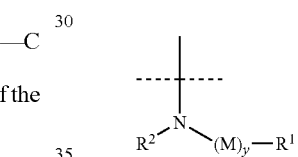

and y is 1; and M is -Z-.
According to a sub-embodiment thereof, compounds of formula V and salts thereof, are provided:

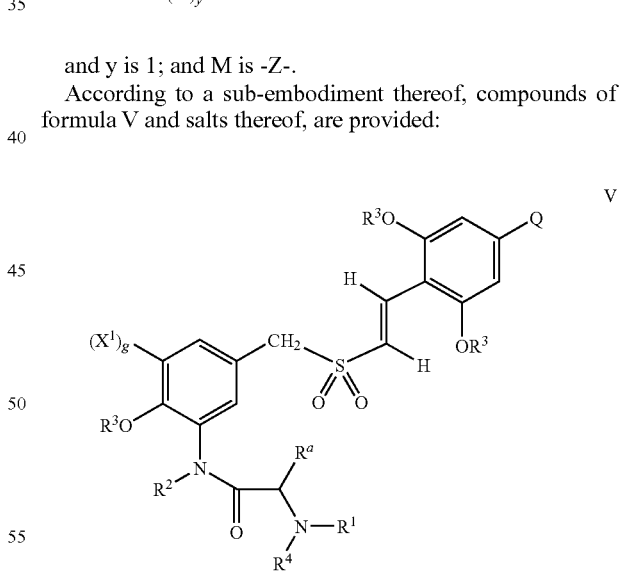

wherein:
each $R^a$ is independently selected from the group consisting of —H, —$CH_3$, —$(CH_2)_3$—NH—C($NH_2$)(=NH), —$CH_2$C(=O)$NH_2$, —$CH_2COOH$, —$CH_2SH$, —$(CH_2)_2$C(=O)—$NH_2$, —$(CH_2)_2COOH$, —$CH_2$(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$—(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

Heterocyclic rings formed by the combination of $R^a$ and $R^1$ include for example: pyrrolidine, hydroxy pyrrolidine, piperidine, homopiperidine and thiazolidine.

Preferred compounds of formula V, include for example the following compounds and salts thereof:

(E)-2,4,6-trimethoxystyryl-3-amino-4-methoxybenzylsulfone-L-lysineamide;

(E)-2,4,6-trimethoxystyryl-3-amino-4-methoxybenzylsulfone-L-serineamide; and (E)-2,4,6-trimethoxystyryl-3-amino-4-methoxybenzylsulfone-D-serineamide.

According to a fifth embodiment of the invention of formula I:

X is

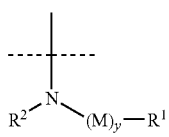

and y is 1; M is $-(CH_2)_a-V-(CH_2)_b-$; and V is $-SO_2-$.

According to a sub-embodiment thereof compounds of formula VI and salts thereof, are provided:

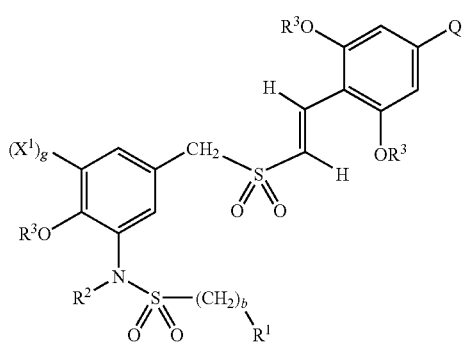

Compounds of formula VI, include for example the following compounds and salts thereof:

(E)-2,4,6-trimethoxystyryl-3-carboxymethylsulfamyl-4-methoxybenzylsulfone;

(E)-2,4,6-trimethoxystyryl-3-(4-methoxybenzenesulfamyl)-4-methoxybenzylsulfone;

(E)-2,4,6-trimethoxystyryl-3-(2,4-dinitrobenzenesulfamyl)-4-methoxybenzylsulfone; and (E)-2,4,6-trimethoxystyryl-3-(2,4-diaminobenzenesulfamyl)-4-methoxybenzylsulfone.

According to a sixth embodiment of the invention of formula I, X is

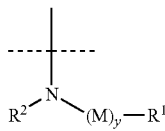

and y is 0 and $R^1$ is $-C(=NH)-NR^4_2$.

According to a sub-embodiment thereof compounds of formula VII, and salts thereof, are provided:

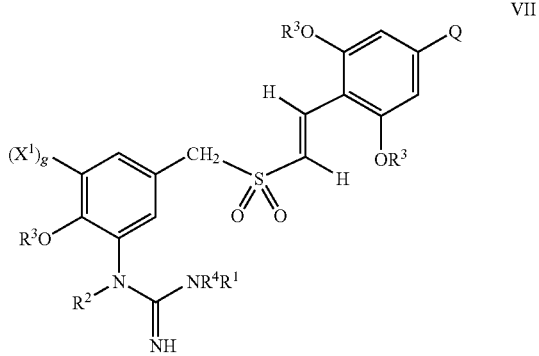

One such compound is (E)-2,4,6-trimethoxystyryl-3-guanidino-4-methoxybenzylsulfone, or a salt thereof.

According to a seventh embodiment of the invention of formula I, X is

and y is 1; and M is $-(C_1-C_6)$alkylene-.

According to one sub-embodiment thereof, compounds of the formula VIII, and salts thereof, are provided:

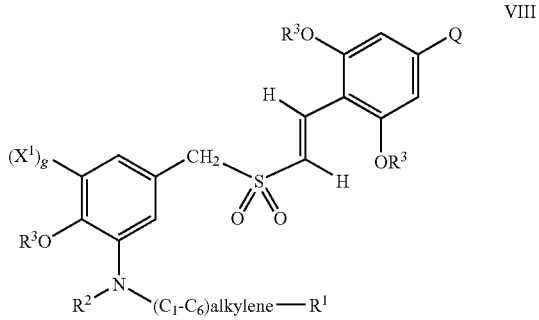

Exemplary compounds of formula VII include for example:

(E)-2,4,6-trimethoxystyryl-3-(N-methylamino)-4-methoxybenzylsulfone;

racemic-(E)-2,4,6-trimethoxystyryl-3-(1-carboxyethyl)amino-4-methoxybenzylsulfone;

D-(E)-2,4,6-trimethoxystyryl-3-(1-carboxyethyl)amino-4-methoxybenzylsulfone;

L-(E)-2,4,6-trimethoxystyryl-3-(1-carboxyethyl)amino-4-methoxybenzylsulfone; and (E)-2,4,6-trimethoxy-styryl-3-(carboxymethylamino)-4-methoxybenzylsulfone and salts thereof.

According to an eighth embodiment of the invention compounds of formula I, of the formula IX and salts thereof are provided:

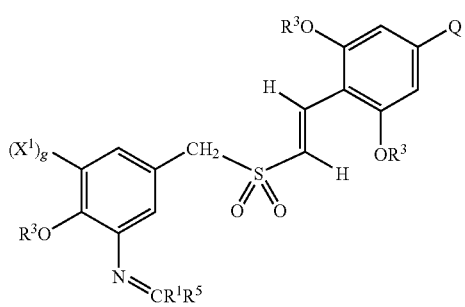

IX

One such compound is (E)-2,4,6-trimethoxystyryl-3-(4-nitrophenylimino)-4-methoxybenzylsulfone or a salt thereof.

According to a ninth embodiment of the invention of formula I, X is

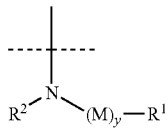

(i)

and y is 1; M is —(CH$_2$)$_a$—V—(CH$_2$)$_b$—; and V is —C(=O)NR$^4$—.

According to a sub-embodiment thereof, compounds of formula X and salts thereof are provided:

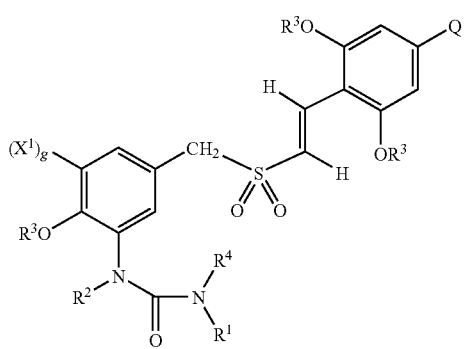

X

An exemplary compound of formula X is (E)-2,4,6-trimethoxystyryl-3-ureido-4-methoxybenzylsulfone, or a salt thereof.

According to a tenth embodiment of the invention of formula I, compounds of the formula II and salts thereof are provided:

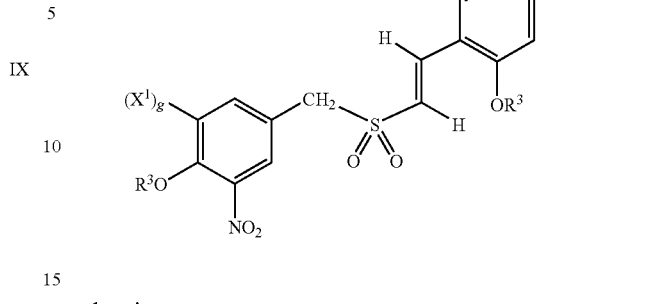

II wherein:
g is 0 or 1;
each R$^3$ is independently selected from —(C$_1$-C$_6$)alkyl;
each R$^4$ is independently selected from the group consisting of —H and —(C$_1$-C$_6$)alkyl;
Q is selected from the group consisting of —H, —(C$_1$-C$_6$)alkoxy, halogen, —(C$_1$-C$_6$)alkyl and —NR$^4$$_2$; and
X$^1$ is selected from the group consisting of (i), (ii) and (iii) below:

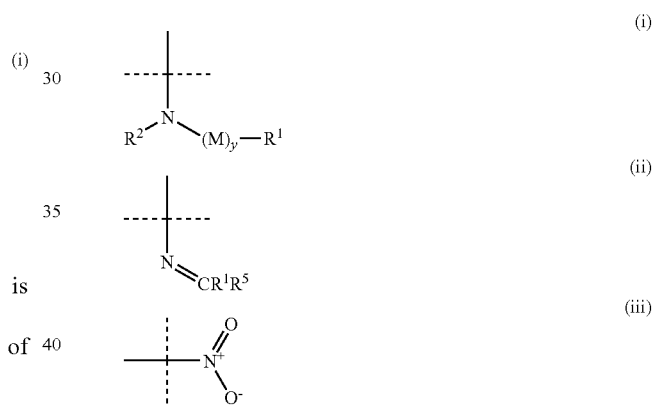

wherein X$^1$ is optionally protected with one or more chemical protecting groups;

Suitable protecting groups will be stable to reactions designed to derivatize the 3-amino group of formula III. Subsequently said protecting groups are optionally removed to regenerate the X$^1$.

In another sub-embodiment, thereof, there are provided compounds of the formula IIa, below:

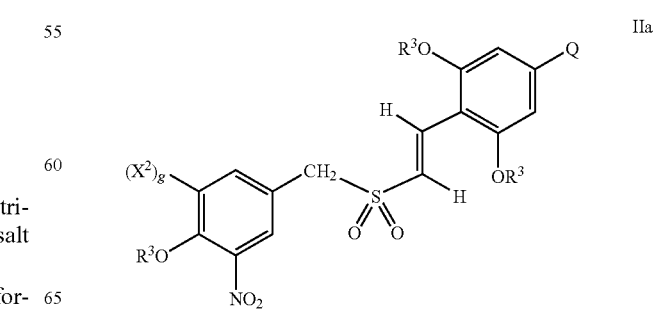

IIa wherein $X^2$ is selected from the group consisting of —$NO_2$ and —$NH_2$, optionally protected with a chemical protecting group.

One such compound of formula IIa is (E)-2,4,6trimethoxystyryl-4-methoxy-3-nitrobenzylsulfone; or a salt thereof.

According to an eleventh embodiment of the invention of formula I, X is

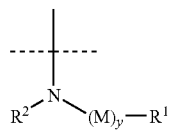

and y is 0; $R^1$ is —$CHR^6R^7$; $R^6$ is $CO_2R^5$ and $R^7$ is $R^a$;

According to a sub-embodiment thereof, compounds of formula XX and salts thereof are provided:

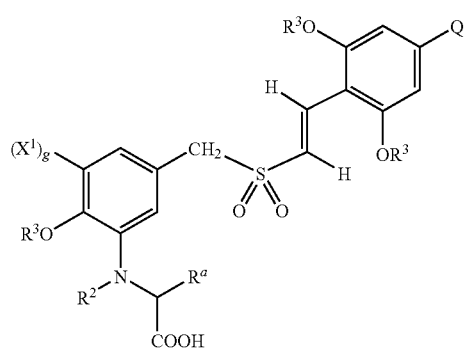

Exemplary compounds of formula XX are (E)-2,4,6-trimethoxystyryl-3-(1-carboxyethyl)amino-4-methoxybenzylsulfone; and (E)-2,4,6-trimethoxystyryl-3-carboxymethylamino-4-methoxybenzylsulfone; or salts thereof.

Preferred compounds are the sodium and potassium salts of (E)-2,4,6-trimethoxystyryl-3-carboxymethylamino-4-methoxybenzylsulfone, particularly the sodium salt.

According to a twelfth embodiment of the invention of formula I, X is

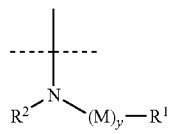

and y is 1; and M is —($C_1$-$C_6$)alkylene-;

According to a sub-embodiment thereof, compounds of formula XXI and salts thereof are provided:

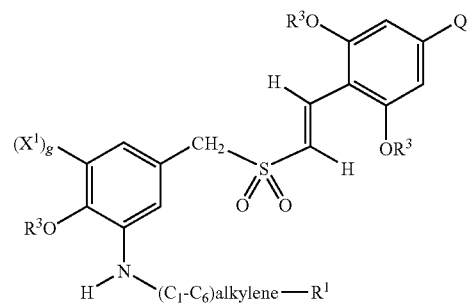

Exemplary compounds of formula XXI are:
(E)-2,4,6-trimethoxystyryl-3-(3-carboxypropylamino)-4-methoxybenzylsulfone;
(E)-2,4,6-trimethoxystyryl-3-(2-carboxyethylamino)-4-methoxybenzylsulfone;
or a salt of such a compound.

According to other embodiments of the invention, processes for preparing compounds according to formula I are provided. In one such embodiment, a process for preparing a compound of formula I is provided comprising (1) coupling a compound of formula IIIa or a salt thereof:

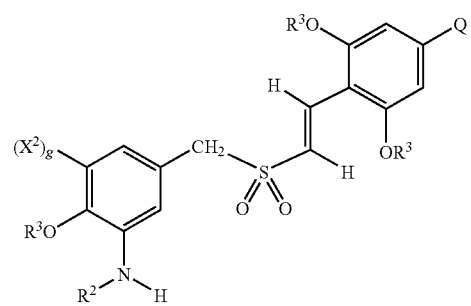

wherein $X^2$ is selected from the group consisting of —$NO_2$ and —$NH_2$, optionally protected with a chemical protecting group, with a compound of formula XI:

$R^1$-A          XI wherein one or more functional groups comprising $R^1$ are optionally protected by chemical protecting groups; and wherein A is a moiety containing an electrophilic reactive center, said moiety selected from the group consisting of:

(a) an alkyl moiety having a leaving group, e.g., a moiety such as a halide, a mesylate or a tosylate;

(b) an aryl halide moiety or aryl pseudo halide moiety.

(c) a carboxylic acid moiety activated with a leaving group, for example a carboxylic acid chloride moiety or a carboxylic acid anhydride moiety;

(d) a sulfonic acid moiety activated with a leaving group, for example a sulfonyl chloride moiety;

(e) a carbamic acid moiety activated with a leaving group, for example a carbamyl chloride moiety;

(f) a cyanate moiety, for example potassium cyanate;

(g) an aldehyde or ketone moiety, or a hydrate thereof or a ketal or acetal thereof;

(h) a carboxylic acid moiety or an amino acid moiety, wherein an amide coupling agent is employed in the reaction;

(i) a moiety that is the reaction product of the reaction of a substituted thiourea moiety and a 1-methyl- or 1-phenyl-2-halopyridinium salt, preferably 2-chloro-1-methyl pyridinium iodide, which iodide is also known as Mukaiyama's reagent;

to form a compound of formula Ia:

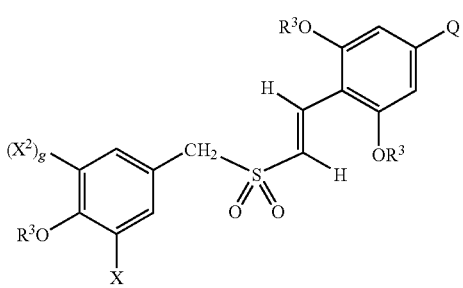

Ia (2) optionally:
(a) when —X² is —NH₂ protected with a protecting group, removing said protecting group from —X² to yield a compound of formula Ib; or
(b) when —X² is —NO₂, chemically reducing said —NO₂;
to form a compound of formula Ib:

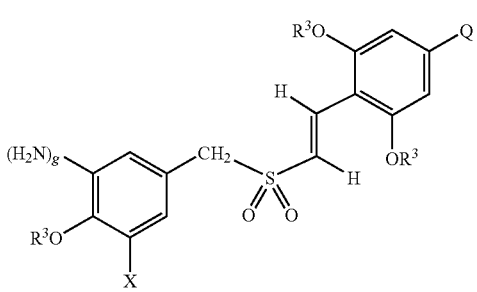

Ib (3) optionally coupling said compound of formula Ib or a salt thereof, with a compound of formula XI:

R¹-A                                                                 XI wherein one or more functional groups comprising R¹ are optionally protected by chemical protecting groups; and A is defined as above; and (4) optionally removing said protecting groups protecting functionalities comprising R¹ to form a compound of formula I:

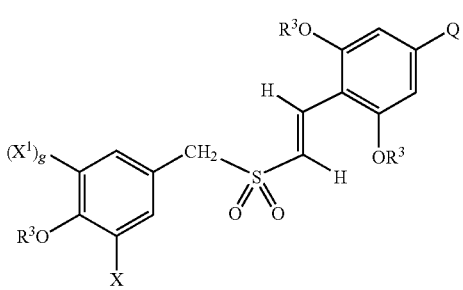

I or a salt thereof.

In the aforesaid process of coupling compounds of formula IIIa to compounds of formula XI, and the coupling of compounds of formula Ib to compounds of formula XI, the electrophile XI in the second coupling may be the same or different from that in the first coupling. Halides which may comprise a leaving group component of the electrophilic functionality A are preferably chloro, bromo or iodo. The term "pseudo halide" refers to a moiety which behaves like a halide in palladium or nickel-catalyzed amination reactions. Pseudo halide moieties include for example, triflates and mesylates.

Carboxylic acid moieties (h) include for example, amino acids bearing optional protecting groups on any alpha-amino functionality, sidechain amino functionality, alpha carboxylic acid functionality, sidechain carboxylic acid functionality or other sidechain functionality that requires a protecting group. Such amino acids may be naturally occurring amino acids or synthetic amino acids including amino acids of either R- or S-absolute configuration.

Additionally, in the aforesaid process of coupling compounds of formula IIIa to compounds of formula XI, and the coupling of compounds of formula Ib to compounds of formula XI, the term "protecting group" or "chemical protecting group" refers to a derivative of a chemical functional group which is employed to derivatize chemical functionalities which would otherwise be incompatible with the conditions of a desired reaction. The protecting group renders this functionality stable to the desired reaction conditions and may later be removed to regenerate the de-protected functionality. One example of the use of protecting groups is in the common reaction of the amino group of a first amino acid with the carboxyl group of a second amino acid to form an amide bond. However, since each reactant contains both an amino and a carboxylate functional group, the reaction between them is (1) nonspecific as to which amino group will react with which carboxyl group, and (2) subject to polymerization since the product of the reaction still contains both reactive moieties. A protecting group on the carboxylate of the first amino acid and a protecting group acid on the amino group of the second amino acid will serve to limit the reagents to the single desired reaction of the amino group of the first amino acid with the carboxylic acid of the second amino acid and yields a product which will not react further because both of the remaining reactive moieties are blocked by protecting groups which may be subsequently be removed.

Any chemical functionality that comprises R¹ may optionally be protected with a chemical protecting group if such a protecting group is useful in the synthesis of compounds of formula I. Appropriate protecting groups for functionalities comprising R¹, include for example, such moieties as tert-butoxy carbonyl (t-Boc) or 9-fluorenyl-methoxycarbonyl (Fmoc).

Additionally, in the aforesaid process of coupling compounds of formula IIIa to compounds of formula XI, and the optional coupling of compounds of formula Ib to compounds of formula XI, amide coupling reagents (h) are compounds used to couple unactivated carboxylic acids to amino groups, such as the anilino moiety of a compound of formula I wherein —X is NH₂ (i.e., wherein X is formula (i), y is 0, R¹ is —H and R² is —H). Such amide coupling reagents include for example, reagents such as diisopropyl carbodiimide and O-(7-azabenzotriazol-1-yl)-N,N,N',N'-tetramethyluronium hexafluorophosphate (HATU).

Following the aforesaid process of coupling compounds of formula IIIa to compounds of formula XI, and the optional coupling of compounds of formula Ib to compounds of formula XI, any protecting groups used in the synthesis of a compound of formula I are optionally removed.

According to a further embodiment of the invention, a process for preparing compounds according to formula IIIa is provided, comprising (1) chemically reducing a compound according to formula IIa; and

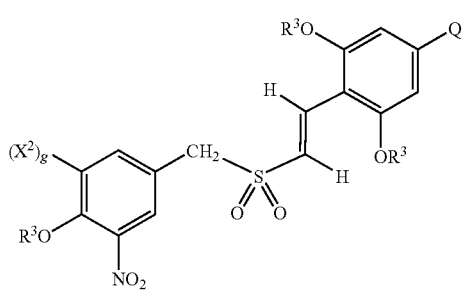

IIa (2) optionally alkylating the resulting aniline via any suitable amine alkytation;
to form a compound of formula IIIa;

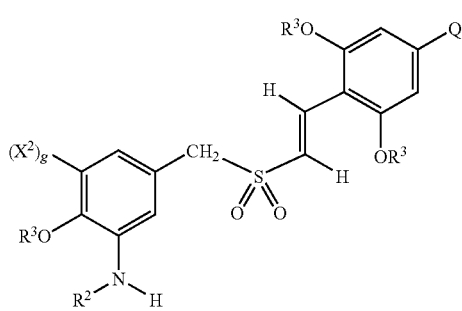

IIIa wherein:
g is 0 or 1;
each $R^3$ is independently selected from —$(C_1-C_6)$alkyl;
each $R^4$ is independently selected from the group consisting of —H, and —$(C_1-C_6)$alkyl;
Q is selected from the group consisting of —H, —$(C_1-C_6)$alkoxy, halogen, —$(C_1-C_6)$alkyl and —$NR^4{}_2$; and
$X^2$ is selected from the group consisting of $NO_2$ and —$NH_2$, optionally protected with a chemical protecting group.
or a salt of such a compound.

The term "chemically reducing" or "chemical reduction" refers to a chemical reaction wherein a reactant which is reduced has a net gain of electrons. In the aforesaid process, a —$NO_2$ functionality is reduced to an —$NH_2$ functionality. This reduction reaction may be effected by a variety of procedures familiar to one of ordinary skill in synthetic chemistry. Such procedures include for example: catalytic hydrogenation using a catalyst such as, for example, palladium or platinum and a hydrogen source, which may be for example, introduction of $H_2$ gas, or may be via a chemical generator of hydrogen such as hydrazine. Other procedures include for example, metal and metal salt reagents such as, for example, $Sn^\circ$, $Zn^\circ$, $Fe^\circ$ and $SnCl_2$. Other reagents that accomplish this type of chemical reduction include for example, sulfite reagents such as sodium hydrosulfite.

Suitable alkylations of an aniline nitrogen include:
(a) alkylation with an alkyl moiety having a leaving group, such as, for example an alkyl halide or an alkyl mesylate; or
(b) reductive amination, ie., reaction with an aldehyde or a ketone in the presence of a reducing agent such as sodium cyanoborohydride or sodium triacetoxy borohydride.

Compounds of formula IIa may be prepared by a process comprising condensing a compound of formula D

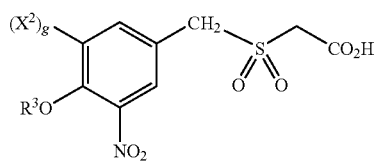

D with a compound of formula E

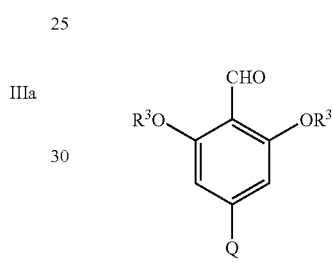

E to form a compound of formula IIa:

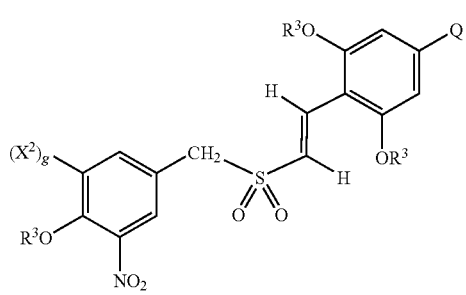

IIa wherein:
g is 0 or 1;
each $R^3$ is independently selected from —$(C_1-C_6)$alkyl;
each $R^4$ is independently selected from the group consisting of —H, and —$(C_1-C_6)$alkyl;
Q is selected from the group consisting of —H, —$(C_1-C_6)$alkoxy, halogen, —$(C_1-C_6)$alkyl and —$NR^4{}_2$; or a salt of such a compound; and
$X^2$ is selected from the group consisting of $NO_2$ and —$NH_2$, optionally protected with a chemical protecting group.

In another embodiment, a process for producing a compound of formula IV is provided. The process comprises:
(1) coupling a compound of formula IIIa

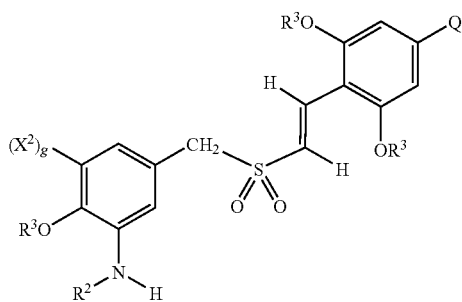

with a compound of formula XII $R^1\text{-}A^1$     XII wherein one or more functional groups comprising $R^1$ are optionally protected by chemical protecting groups; and
wherein $A^1$ is a carboxylic acid moiety with a leaving group;
to give a compound of formula IVa:

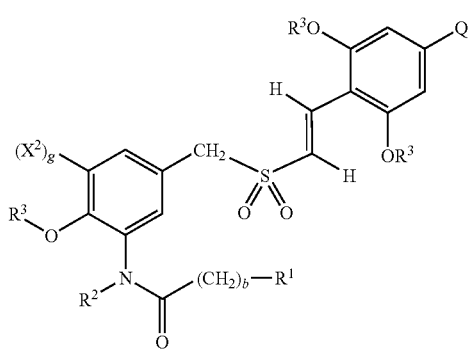

(2) optionally:
(a) when $—X^2$ is $—NH_2$ protected with a protecting group, removing said protecting group from $—X^2$ to yield a compound of formula IVb; or
(b) when $—X^2$ is $—NO_2$, chemically reducing said $—NO_2$ to $—NH_2$, to form a compound of formula IVb:

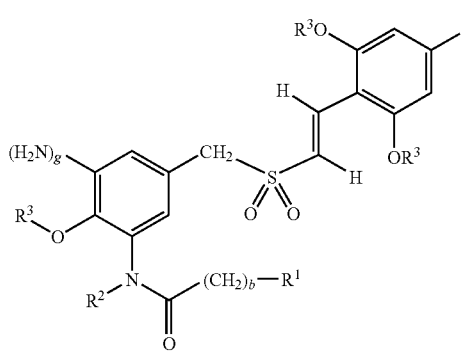

(3) optionally coupling said compound of formula IVb or a salt thereof with a compound of formula XI:

$R^1\text{-}A$     XI wherein one or more functional groups comprising $R^1$ are optionally protected by chemical protecting groups; and
wherein A is a moiety containing an electrophilic reactive center defined as above; and
(4) optionally removing said protecting groups protecting functionalities comprising $R^1$ to form a compound of formula IV, or a salt thereof:

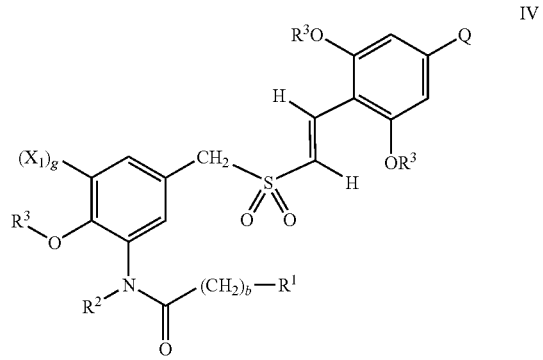

According to another embodiment of the invention, a process for producing a compound according to formula V is provided. The process comprises:
(1) coupling a compound of formula IIIa with
(a) a compound of formula XIII

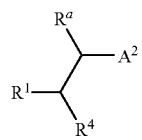

wherein one or more functional groups comprising $R^1$ are optionally protected by chemical protecting groups; and
wherein $A^2$ is a carboxylic acid moiety; and
(b) a coupling reagent such as diisopropylcarbodiimide;
to give a compound of Va:

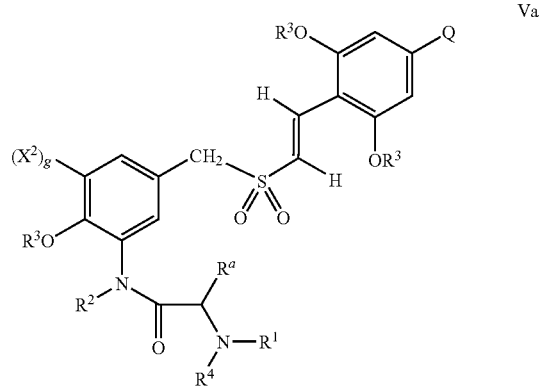

(2) optionally:
(a) when —X² is —NH₂ protected with a protecting group; removing said protecting group from —X² to yield a compound of formula Vb; or
(b) when —X² is —NO₂, chemically reducing said —NO₂ to —NH₂;
to form a compound of formula Vb:

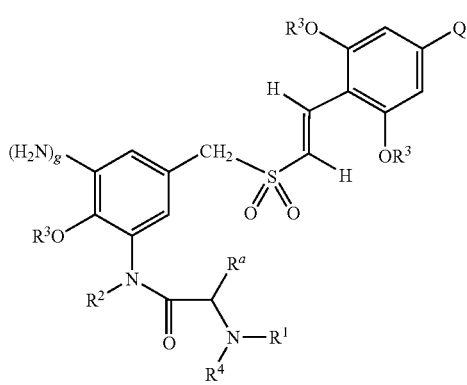
Vb (3) optionally coupling said compound of formula Vb or a salt thereof with a compound of formula XI:
wherein one or more functional groups comprising R¹ are optionally protected by chemical protecting groups; and
wherein A is a moiety containing an electrophilic reactive center as defined above; and
(4) optionally removing said protecting groups used in the synthesis such as tert-butoxy carbonyl (t-Boc) or 9-fluorenyl-methoxycarbonyl (Fmoc);
to form a compound of formula V, or a salt thereof:

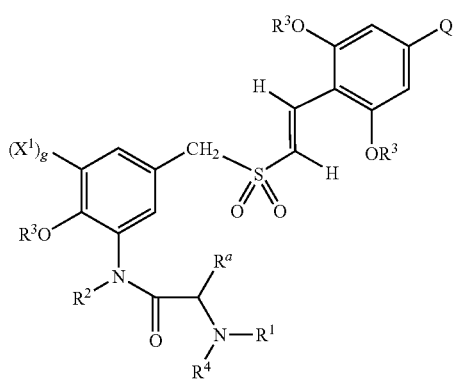
V

Amide coupling reagents used to couple unactivated carboxylic acid moieties to aromatic amino groups such as the 3-amino group of compounds of formula I, and amino groups associated with peptidic R¹ substituents, include for example, reagents such as diisopropyl carbodiimide (DIC) and O-(7-azabenzotriazol-1-yl)-N,N,N',N'-tetramethyluronium hexafluorophosphate (HATU).

In a further embodiment of the invention, a process for producing a compound according to formula VI is provided, comprising:

(1) coupling a compound of formula IIIa:

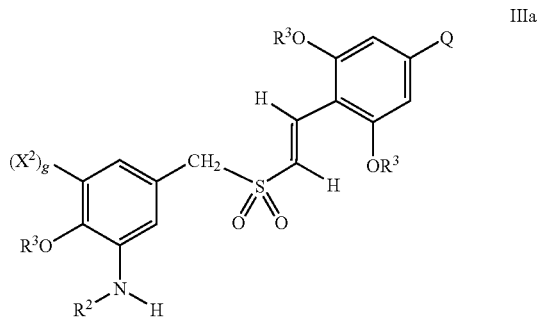
IIIa with a compound of formula XIV:

R¹-A³    XIV wherein one or more functional groups comprising R¹ are optionally protected by chemical protecting groups; and
wherein A³ is a sulfonyl chloride moiety;
to give a compound of VIa:

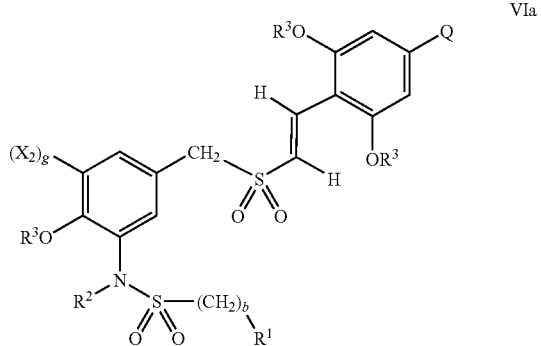
VIa (2) optionally:
(a) when X² is —NH₂ protected with a protecting group, removing said protecting group from —X² to yield a compound of formula VIb; or
(b) when —X² is —NO₂, chemically reducing said —NO₂ to —NH₂, to form a compound of formula VIb:

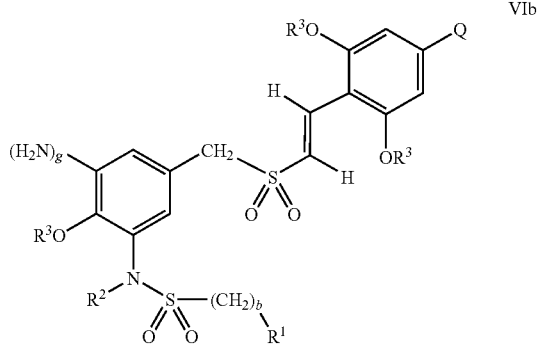
VIb (3) optionally coupling said compound of formula VIb or a salt thereof with a compound of formula XI:

R¹-A    XI wherein one or more functional groups comprising R¹ are optionally protected by chemical protecting groups; and
wherein A comprises a moiety containing an electrophilic reactive center as defined above; and (4) optionally removing said protecting groups to form a compound of formula VI, or a salt thereof:

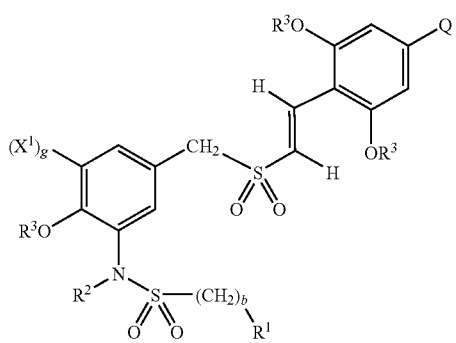

VI

In another embodiment of the invention, a process for producing a compound according to formula VII is provided, comprising:

(1) coupling a compound of formula IIIa

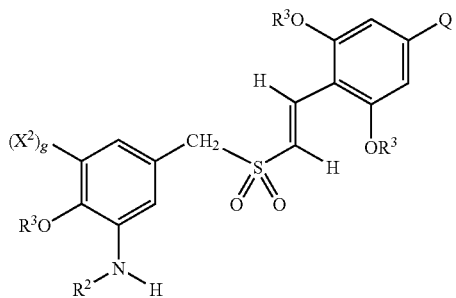

IIIa with a compound of formula XV:

R$^1$-A$^4$  XV wherein one or more functional groups comprising R$^1$ are optionally protected by chemical protecting groups; and wherein A$^4$ is a moiety which is a reactive intermediate produce of a substituted thiourea, such as N,N'-bis-(tert-butoxycarbonyl)thiourea and a 1-methyl- or 1-phenyl-2-halopyridinium salt, preferably 2-chloro-1-methyl pyridinium iodide;

to give a compound of VIIa:

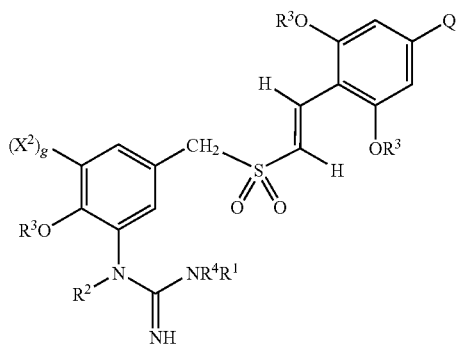

VIIa (2) optionally:
(a) when —X$^2$ is —NH$_2$ protected with a protecting group, removing said protecting group from —X$^2$ to yield a compound of formula VIIb; or (b) when —X$^2$ is —NO2, chemically reducing said —NO$_2$ to —NH$_2$ to form a compound of formula VIIb:

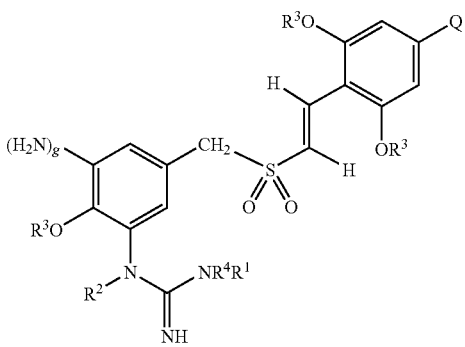

VIIb (3) optionally coupling said compound of formula VIIb or a salt thereof:
with a compound of formula XI:

R$^1$-A  XI wherein one or more functional groups comprising R$^1$ are optionally protected by chemical protecting groups; and wherein A comprises a moiety containing an electrophilic reactive center as defined above; and (4) optionally removing said protecting groups to form a compound of formula VII, or a salt thereof:

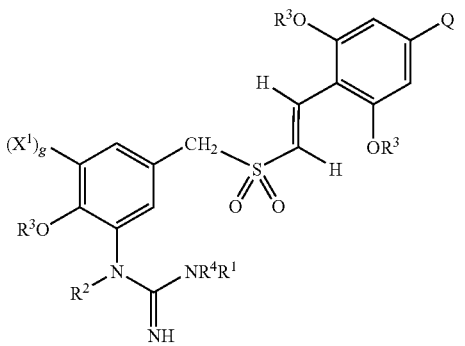

VII

In another embodiment of the invention, a process for producing a compound according to formula VII is provided, comprising (1) coupling a compound of formula IIIa:

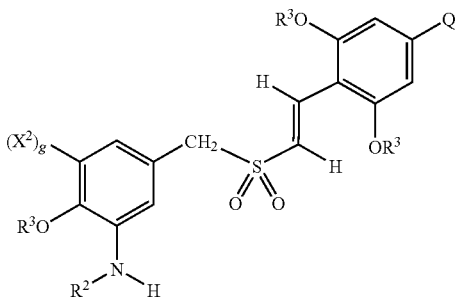

IIIa with a compound of formula XVI

R$^1$-A  XVI wherein one or more functional groups comprising R$^1$ are optionally protected by chemical protecting groups; and wherein A$^5$ is an alkyl moiety with a leaving group;

to give a compound of VIIIa:

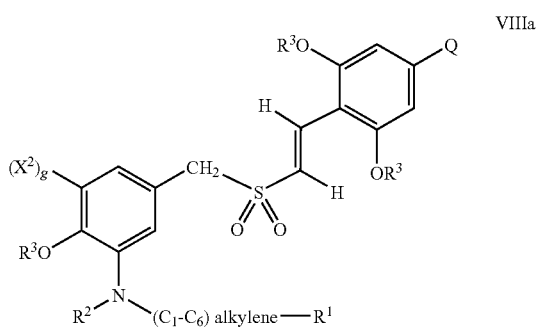

(2) optionally
(a) when —$X^2$ is —$NH_2$ protected with a protecting group, removing said protecting group from —$X^2$ to yield a compound of formula VIIIb; or
(b) when —$X^2$ is —$NO_2$, chemically reducing said —$NO_2$ to —$NH_2$, to form a compound of formula VIIIb:

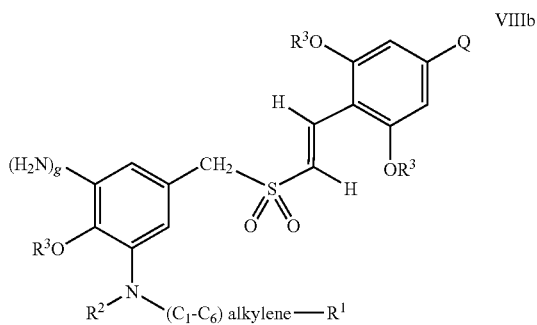

(3) optionally coupling said compound of formula VIIIb or a salt thereof:
with a compound of formula XI:

wherein one or more functional groups comprising $R^1$ are optionally protected by chemical protecting groups; and
wherein A comprises a moiety containing an electrophilic reactive center as defined above; and
(4) optionally removing said protecting groups to form a compound of formula VII, or a salt thereof:

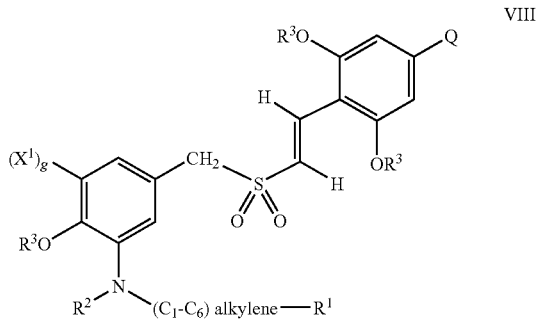

Appropriate leaving groups for alkyl moieties include for example, groups such as halides, mesylates or tosylates.

In a further embodiment of the invention, a process for producing a compound of formula IX is provided, comprising:

(1) coupling a compound of formula IIIa

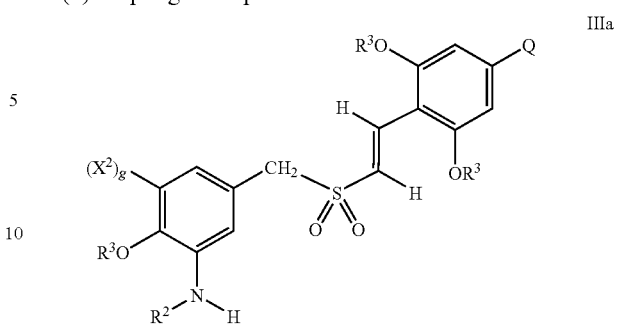

wherein $R^2$ is —H;
with a compound of formula XVII

wherein one or more functional groups comprising $R^1$ are optionally protected by chemical protecting groups; and
wherein $A^6$ is a moiety containing an aldehyde or ketone moiety, a hydrate thereof, or a ketal or acetal thereof;
to give a compound of IXa:

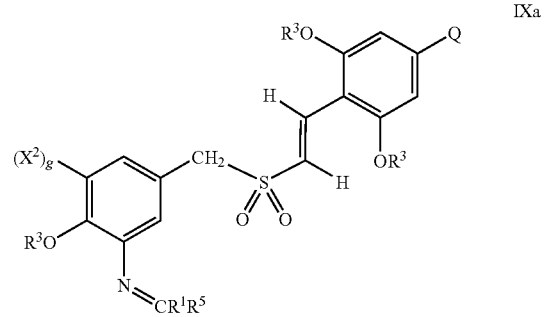

(2) optionally
(a) when —$X^2$ is —$NH_2$ protected with a protecting group, removing said protecting group from —$X^2$ to yield a compound of formula IXb; or
(b) when —$X^2$ is —$NO_2$, chemically reducing said —$NO_2$ to —$NH_2$, to form a compound of formula IXb:

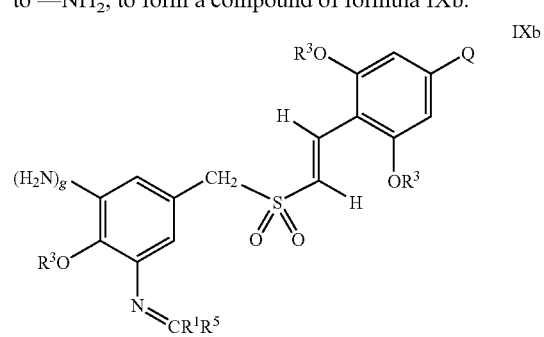

(3) optionally coupling said compound of formula IXb or a salt thereof:
with a compound of formula XI:

wherein one or more functional groups comprising $R^1$ are optionally protected by chemical protecting groups; and
wherein A comprises a moiety containing an electrophilic reactive center as defined above; and (4) optionally removing said protecting groups to form a compound of formula IX, or a salt thereof:

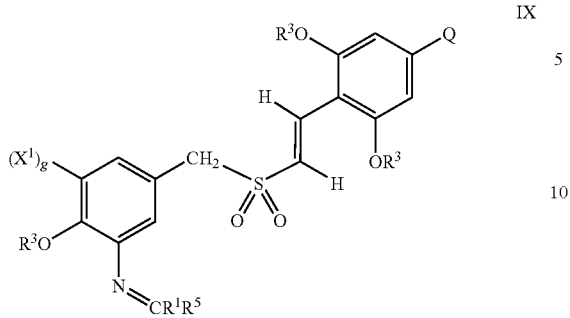

In another embodiment of the invention, a process for producing a compound of formula X is provided, comprising:

(1) coupling a compound of formula IIIa:

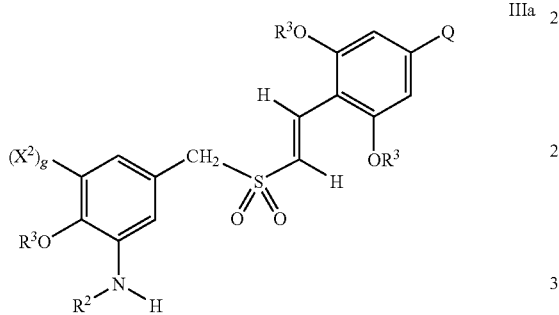

with a compound of formula XVIII

wherein one or more functional groups comprising $R^1$ are optionally protected by chemical protecting groups; and wherein (a) if A is a cyanate moiety, then $R^1$ is selected from the group consisting of —H, ($C_1$-C6) alkyl and aryl; and and $R^4$ is —H; and (b) if A is a carbamic acid moiety activated with a leaving group, then $R^1$ and $R^4$ of formula X are as defined above;

to give a compound of the formula Xa:

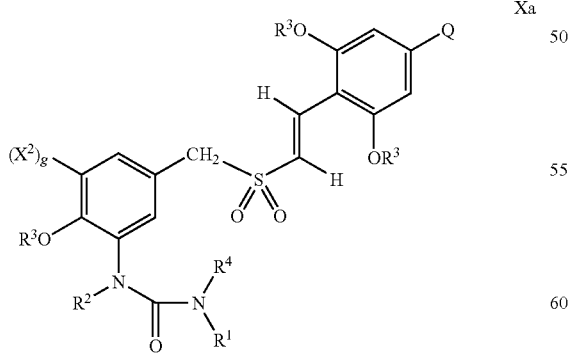

(2) optionally:

(a) when —$X^2$ is —$NH_2$ protected with a protecting group, removing said protecting group from —$X^2$ to yield a compound of formula Xb; or (b) when —$X^2$ is —$NO_2$, chemically reducing said —$NO_2$ to —$NH_2$, to form a compound of formula Xb:

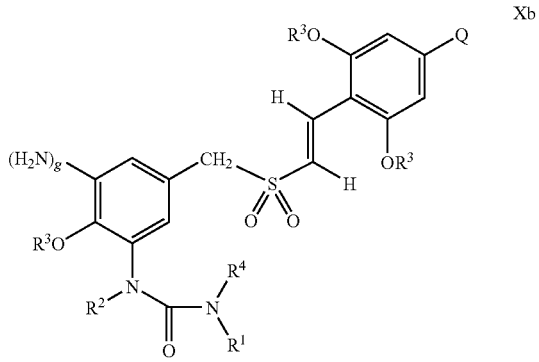

(3) optionally coupling said 5-$NH_2$ compound of formula Xb or a salt thereof:

with a compound of formula XI:

$R^1$-A      XI wherein one or more functional groups comprising $R^1$ are optionally protected by chemical protecting groups; and wherein A is a moiety containing an electrophilic reactive center as defined above; and (4) optionally removing said protecting groups to form a compound of formula X, or a salt thereof:

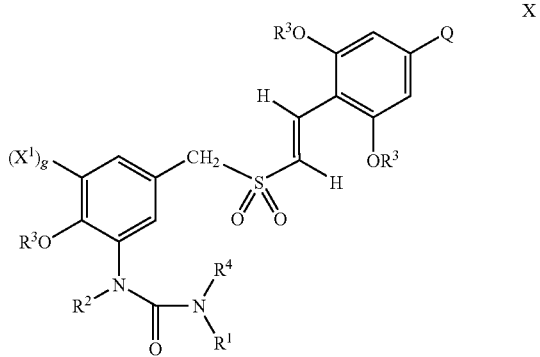

In another embodiment, a process for producing a compound of formula XX is provided:

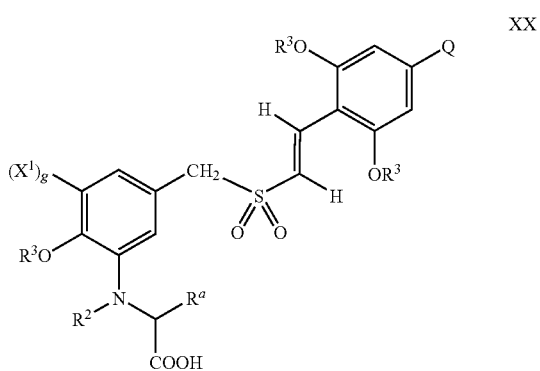

The process comprises:

(1) coupling a compound of formula IIIa:

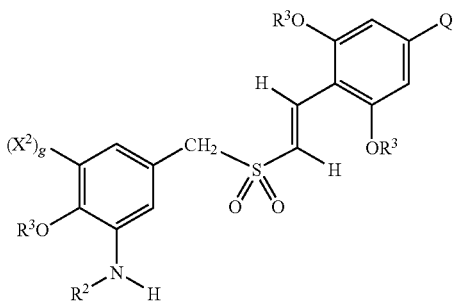

wherein:

g is 0 or 1;

each $R^3$ is independently selected from —$(C_1-C_6)$alkyl;

each $R^4$ is independently selected from the group consisting of —H, and —$(C_1-C_6)$alkyl;

Q is selected from the group consisting of —H, —$(C_1-C_6)$alkoxy, halogen, —$(C_1-C_6)$alkyl and —$NR^4{}_2$; and $X^2$ is selected from the group consisting of —$NO_2$ and —$NH_2$, optionally protected with a chemical protecting group;

or a salt of such a compound;

with a compound of formula XIX:

$$R^1\text{-}A^8 \qquad \text{XIX}$$

wherein:

$R^1$ is —$CHR^6R^7$;

$R^6$ is —$CO_2(C_1-C_6)$alkyl;

$R^7$ is $R^a$; and $A^8$ is a leaving group;

wherein one or more functional groups comprising $R^1$ are optionally protected by chemical protecting groups to form a compound of formula XXa:

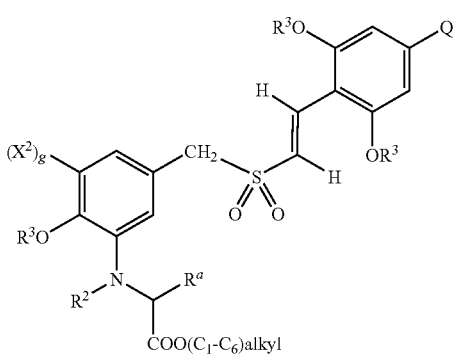

(2) optionally:

(a) when —$X^2$ is —$NH_2$ protected with a protecting group, removing said protecting group from —$X^2$ to yield a compound of formula XXb; or (b) when —$X^2$ is —$NO_2$, chemically reducing said —$NO_2$ to —$NH_2$;

to form a compound of formula XXb:

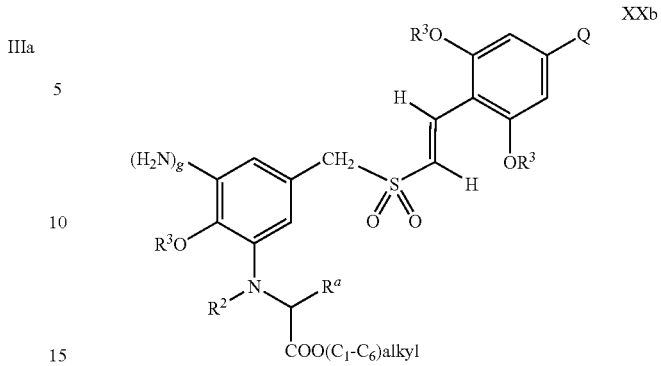

(3) optionally coupling said compound of formula XXb or a salt thereof:

with a compound of formula XI:

$$R^1\text{-}A \qquad \text{XI}$$

wherein one or more functional groups comprising $R^1$ are optionally protected by chemical protecting groups; and wherein A is a moiety containing an electrophilic reactive center as described above; and (4) optionally removing said protecting groups protecting functionalities comprising $R^1$ to form said compound of formula XXc;

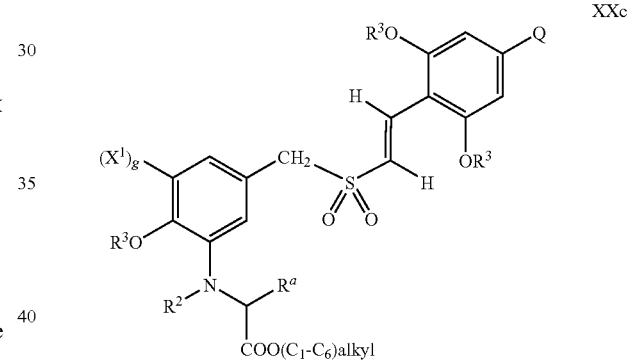

(5) reacting XXc with an aqueous base, preferably sodium hydroxide to yield a compound of formula XX as the carboxylic acid salt, preferably the sodium salt. The free acid of a compound of formula XX may be produced by either regenerating the free acid from the carboxylate salt via reaction with one equivalent of an acid such as aqueous HCl; or by performing the hydrolysis of step (5) by reacting intermediate XXc with an aqueous acid.

Appropriate leaving groups for alkyl moieties such as those in intermediate XIX include for example, groups such as halides, mesylates and tosylates.

In yet another embodiment of the invention, a conjugate of the formula I-L-Ab is provided wherein I is a compound of formula I; Ab is an antibody; and -L- is a single bond or a linking group covalently linking said compound of formula I to said antibody.

In a further embodiment of the invention, a conjugate of the formula III-L-Ab is provided wherein III is a compound of formula III; Ab is an antibody; and -L- is a single bond or a linking group covalently linking said compound of formula III to said antibody.

In a preferred sub-embodiment of the aforesaid conjugates of the formulae I-L-Ab and III-L-Ab, said antibody (Ab) is a monoclonal antibody or a monospecific polyclonal antibody.

In a more preferred sub-embodiment of the aforesaid conjugates of the formulae I-L-Ab and III-L-Ab, the aforesaid antibody (Ab) is a tumor-specific antibody.

In yet a further embodiment of the present invention, there is provided a compound of formula I derivatized as a substrate for a β-lactamase enzyme.

A pharmaceutical composition is also provided comprising a pharmaceutically acceptable carrier and one or more compounds of formula I above, or a pharmaceutically acceptable salt of such compound.

A pharmaceutical composition is additionally provided comprising a pharmaceutically acceptable carrier and at least one conjugate according to formula I-L-Ab or III-L-Ab.

According to another embodiment of the invention, a method of treating an individual for a proliferative disorder, particularly cancer, is provided, comprising administering to said individual an effective amount of a compound according to formula I, or a pharmaceutically acceptable salt of such compound, alone or in combination with a pharmaceutically acceptable carrier.

In another embodiment of the invention, a method of treating an individual for a proliferative disorder, particularly cancer, is provided, comprising administering to said individual an effective amount of at least one conjugate of the formula I-L-Ab or III-L-Ab.

In another embodiment of the invention, a method of inhibiting growth of tumor cells in an individual afflicted with cancer is provided comprising administering to said individual an effective amount of a compound according to formula I, or a pharmaceutically acceptable salt of such compound, alone or in combination with a pharmaceutically acceptable carrier.

In another embodiment of the invention, a method of inhibiting growth of tumor cells in an individual afflicted with cancer is provided comprising administering to said individual an effective amount of at least one conjugate of the formula I-L-Ab or III-L-Ab.

In another embodiment, a method of inducing apoptosis of cancer cells, more preferably tumor cells, in an individual afflicted with cancer is provided, comprising administering to said individual an effective amount of a compound according to formula I, or a pharmaceutically acceptable salt of such compound, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of at least one conjugate of the formula I-L-Ab or III-L-Ab, alone or in combination with a pharmaceutically acceptable carrier.

The styryl benzylsulfones are characterized by cis-trans isomerism resulting from the presence of a double bond. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p. 127-138. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher ranking groups are on opposite sides of the double bond, is designated E (for the German word "entgegen", which means "opposite"). The compounds of the present invention have the E configuration as shown below.

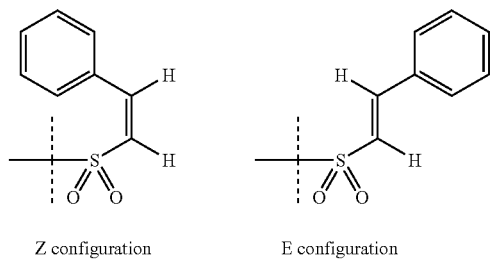

Z configuration      E configuration

The term "acyl" means a radical of the general formula —C(=O)—R, wherein —R is hydrogen, hydrocarbyl, amino or alkoxy. "Examples include for example, acetyl (—C(=O)CH$_3$), propionyl (—C(=O)CH$_2$CH$_3$), benzoyl (—C(=O)C$_6$H$_5$), phenylacetyl (—C(=O)CH$_2$C$_6$H$_5$), carboethoxy (—CO$_2$Et), and dimethylcarbamoyl (—C(=O)N(CH$_3$)$_2$).

The term "alkyl", by itself or as part of another substituent means, unless otherwise stated, a straight, branched or cyclic chain hydrocarbon radical, including di- and multi-radicals, having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "alkylene", by itself or as part of another substituent means, unless otherwise stated, a divalent straight, branched or cyclic chain hydrocarbon radical.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "alkenyl" employed alone or in combination with other terms, means, unless otherwise stated, a stable monounsaturated or di-unsaturated hydrocarbon radical straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

The term "amine" or "amino" refers to radicals of the general formula —NRR', wherein R and R' are independently selected from hydrogen or a hydrocarbyl radical, or wherein R and R' combined form a heterocyle. Examples of amino groups include: —NH$_2$, methyl amino, diethyl amino, anilino benzyl amino, piperidine, piperazine, and indoline.

The term "carbamyl" means the group —C(=O)NRR', wherein R and R' are independently selected from hydrogen or a hydrocarbyl radical, or wherein R and R' combined form a heterocyle. Examples of carbamyl groups include: —C(=O)NH$_2$ and —C(=O)N(CH$_3$)$_2$.

The term "carboxy($C_1$-$C_3$)alkoxy" means a radical in which the carboxy group —COOH is attached to a carbon of a straight or branched chain alkoxy group containing one to three carbon atoms. The radical thus contains up to four carbon atoms. Examples include: —O(CH$_2$)$_3$CO$_2$H and —O(CH$_2$)$_2$CO$_2$H.

The term "cycloalkyl" refers to ring-containing alkyl radicals;

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$S(=O)—CH$_3$. Up to two heteroatoms may be consecutive, such as, for example, —CH$_2$—NH—OCH$_3$.

The term "heteroalkenyl" by itself or in combination with another term means, unless otherwise stated, a stable straight or branched chain monounsaturated or di-unsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH'CH—CH2—SH.

The term "hydroxyalkyl" means an alkyl radical wherein one or more of the carbon atoms is substituted with hydroxy. Examples include —CH$_2$CH(OH)CH$_3$ and —CH$_2$CH$_2$OH.

The terms "halo" or "halogen" by themselves or as part of another substituent mean, unless otherwise stated, a fluorine, chlorine, bromine, or iodine atom.

The term "di(C$_1$-C$_6$)alkylamino(C$_2$-C$_6$)alkoxy" means (alkyl)$_2$N(CH$_2$)$_n$O— wherein the two alkyl chains connected to the nitrogen atom independently contain from one to six carbon atoms, preferably from one to three carbon atoms, and n is an integer from 2 to 6. Preferably, n is 2 or 3. Most preferably, n is 2, and the alkyl groups are methyl, that is, the group is the dimethylaminoethoxy group, (CH$_3$)$_2$NCH$_2$CH$_2$O—.

The term "uphosphonato" means the group —PO(OH)$_2$.

The term "sulfamyl" means the group —SO$_2$NRR', wherein R and R' are independently selected from hydrogen or a hydrocarbyl radical, or wherein R and R' combined form a heterocycle. Examples of sulfamyl groups include: —SO$_2$NH$_2$, —SO$_2$N(CH$_3$)$_2$ and —SO$_2$NH(C$_6$H$_5$).

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "aryl-(C$_1$-C$_3$)alkyl" means a radical wherein a one to three carbon alkylene chain is attached to an aryl group, e.g., —CH$_2$CH$_2$phenyl. Similarly, the term "heteroaryl-(C$_1$-C$_3$)alkyl" means a radical wherein a one to three carbon alkylene chain is attached to a heteroaryl group, e.g., "CH$_2$CH$_2$pyridyl. The term "substituted aryl-(C$_1$-C$_3$)alkyl" means an aryl-(C$_1$-C$_3$)alkyl radical in which the aryl group is substituted. The term "substituted heteroaryl-(C$_1$-C$_3$)alkyl" means a heteroaryl-(C$_1$-C$_3$)alkyl radical in which the heteroaryl group is substituted.

The term "arylene", by itself or as part of another substituent means, unless otherwise stated, a divalent aryl radical. Preferred are divalent phenyl radicals, particularly 1,4-divalent phenyl radicals.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character.

Examples of non-aromatic heterocycles include monocyclic groups such as: Aziridine, oxirane, thiamine, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: Indolyl, particularly 3-, 4-, 5-, 6- and 7-indolyl, indolinyl, quinolyl, tetrahydroquinolyl, isoquinolyl, particularly 1- and 5-isoquinolyl, tetrahydroisoquinolyl, cinnolinyl, quinoxalinyl, particularly 2- and 5-quinoxalinyl, quinazolinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative, not limiting.

The term "heteroarylene", by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from pyridine, piperazine, pyrimidine, pyrazine, furan, thiophene, pyrrole, thiazole, imidazole and oxazole.

The term "hydrocarbyl" refers to any moiety comprising only hydrogen and, carbon atoms.

The term 'substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

The term "antibody" is intended to encompass not only intact antigen-binding immunoglobulin molecules, but also to include antigen-binding fragments thereof such as Fab, Fab' and F(ab)$_2$ fragments, or any other fragment retaining the antigen-binding ability of an intact antibody.

The term "humanized antibody" refers to an antibody that has its complementary determining regions (CDR's) derived from a non-human species immunoglobulin, and the remainder of the antibody molecule derived from a human immunoglobulin.

The term "chimeric antibody" means an antibody comprising a variable region and a constant region derived from different species.

The term "humanized chimeric antibody" is meant a chimeric antibody in which at least the constant region is human-derived.

The term "monospecific polyclonal antibody" means an antibody preparation comprising multiple antibody species having specificity for a single antigen.

The term "effective amount" when used herein refers to the amount of a compound of formula I that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation.

The term "monovalent peptidyl moiety" refers to a peptide radical as a substituent on a molecule of formula I. Such a radical has a chemical structure that varies from the structure of the corresponding peptide in that the structural component of the peptide, i.e., an alpha amino group, a sidechain amino group, an alpha carboxyl group or a sidechain carboxyl group, will form a different functionality when bonded to the molecule of which it is to be a substituent. For example, when a peptide as shown below:

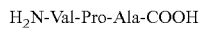
H$_2$N-Val-Pro-Ala-COOH is a substituent on a compound of formula I, and said peptide is coupled to a compound of formula I such that a carboxyl moiety of said peptide is coupled to a free amine moiety on formula I, there is a functional elimination of H$_2$O that results in the formation of an amide bond. As a practical result, the corresponding monovalent peptidyl substituent will be as shown to the left of the dotted line in the depiction below of the aforementioned peptide bonded to a compound of formula I:

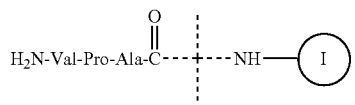

DETAILED DESCRIPTION OF THE INVENTION

Figure 1:
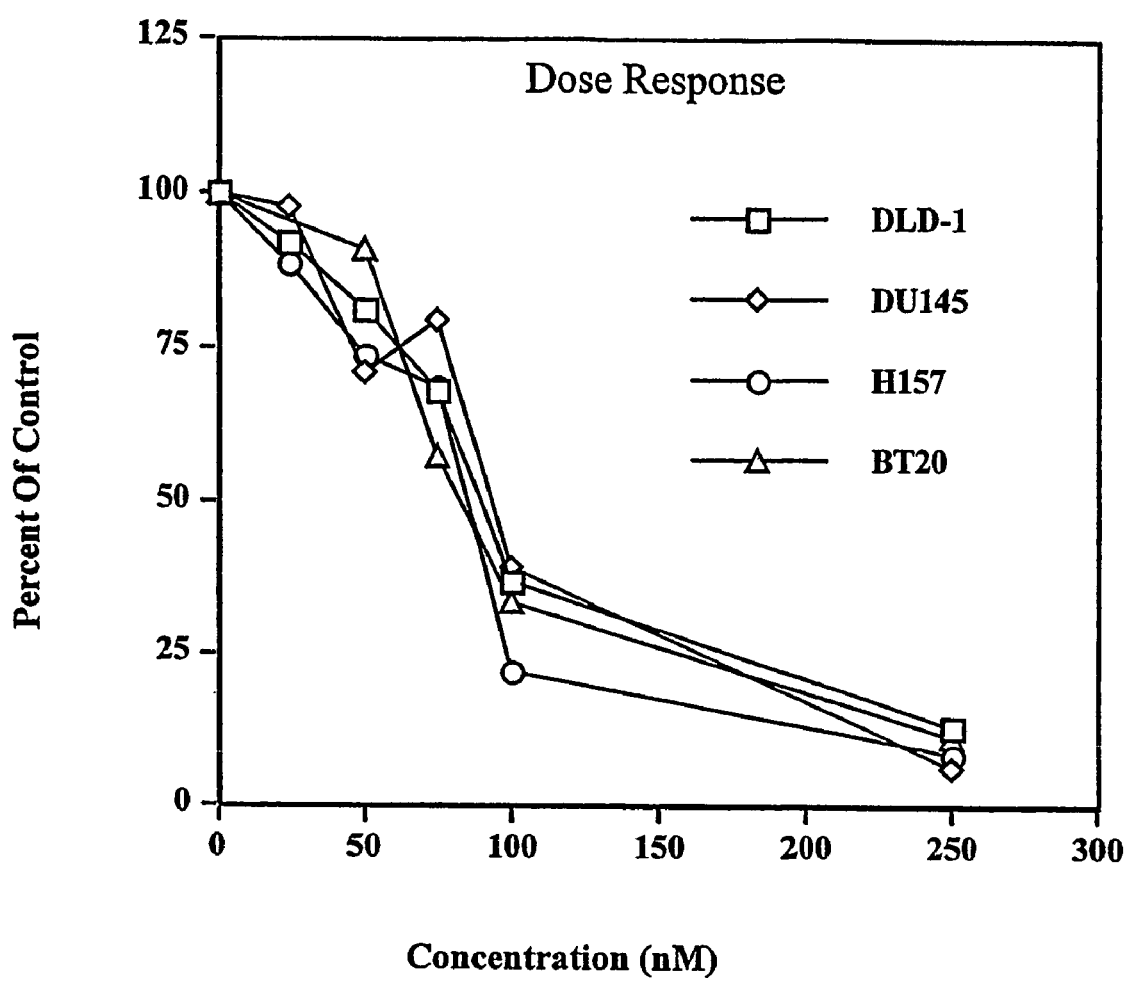
FIG. 1 shows the effect of (E)-2,4,6-trimethoxystyryl-3-(carboxymethylamino)-4-methoxybenzylsulfone on the growth of cells of the indicated tumor cell lines. Values are plotted as the percent of drug-treated cells remaining viable compared to DMSO-treated cells of the same type.

According to the present invention, certain substituted styryl benzylsulfone derivatives selectively kill various tumor cell types without killing normal cells.

Without wishing to be bound by any theory, it is believed that the compounds affect the MAPK signal transduction pathway, thereby affecting tumor cell growth and viability. This cell growth inhibition is associated with regulation of the ERK and JNK types of MAPK. Without wishing to be bound by any theory, the styryl sulfones of the present invention may block the phosphorylating capacity of ERK-2.

The compounds of the invention inhibit the proliferation of tumor cells by inducing cell death.

The compounds of the invention are believed effective against broad spectrum of cancer types of diverse histologic subtype and origin. Cancer types which may be treated by the present compounds include for example, those cancers listed and described in the National Cancer Institute's "CancerNet" at http://cancernet.nci.nih.gov/pdq/pdq_treatment.shtml, which is herein incorporated by reference in its entirety.

For example, the compounds of the invention may be used to kill primary or metastatic tumor or neoplastic cells in cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, and chronic myelocytic leukemia).

The present compounds may also be used to kill primary or metastatic tumor or neoplastic cells in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Furthermore, the present compounds are believed effective in treating cancers or tumors in any prognostic stage of development, as measured, for example, by the "Overall Stage Groupings" (also called "Roman Numeral") or the Tumor, Nodes, and Metastases (TNM) staging systems. Appropriate prognostic staging systems and stage descriptions for a given cancer are known in the art, for example as described in http://cancernet.nci.nih.govlpdq/pdq_treatment.shtml, supra. The compounds do not kill normal cells in concentrations at which tumor cells are killed.

The compounds are also believed useful in the treatment of non-cancer proliferative disorders. Non-cancer proliferative disorders are characterized by the uncontrolled growth of cells with a benign phenotype, meaning that the cells evade only the normal controls on growth, but cannot metastasize. Non-cancer proliferative disorders which may be treated with the present compounds include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Dupuytren's fibrosis, cirrhosis, atherosclerosis and vascular restenosis.

Treatment of this broad range of tumor cells with the styryl benzylsulfone compounds of the invention leads to inhibition of cell proliferation and induction of apoptotic cell death.

Tumor cells treated with the compounds of the invention accumulate in the G2/M phase of the cell cycle. As the cells exit the G2/M phase, they appear to undergo apoptosis. Treatment of normal cells with the styryl benzylsulfones does not result in apoptosis.

Methods of Preparation

The intermediate (E)-styryl-3-nitrobenzylsulfones of formula II of the present invention may be prepared by a Knoevenagel condensation of aromatic aldehydes with benzylsulfonyl acetic acids. These intermediate nitro derivatives of formula II may then be reduced to the corresponding aniline derivatives and subsequently alkylated at the aniline nitrogen to give the intermediate (E)-styryl-3-aminobenzylsulfones of formula III. Said aniline alkylation may be by alkylation techniques well known to one of ordinary skill in the art. For example, said aniline nitrogen may be alkylated by a $SN_2$ reaction with an alkyl moiety comprising a leaving group such as a halide, a tosylate or a mesylate. Examples of such reagents include for example, methyl iodide and benzyl bromide. Another method of alkylating an aniline nitrogen is via a reductive amination with an aldehyde or a ketone in the presence of an appropriate reducing agent. Suitable reducing agents for this reaction include for example sodium cyanoborohydride and sodium triacetoxy borohydride, which will, at a slightly acidic pH, selectively reduce an imine intermediate in the presence of said aldehyde or ketone starting material, yielding an alkylated product of formula III.

The Knoevenagel condensation is described by Reddy et al., *Acta. Chim. Hung.* 115:269-71 (1984); Reddy et al., *Sulfur Letters* 13:83-90 (1991); Reddy et al., *Synthesis* No. 4, 322-323 (1984); and Reddy et al., *Sulfur Letters* 7:43-48 (1987), the entire disclosures of which are incorporated herein by reference.

According to the Scheme 1 below, the benzyl thioacetic acid C is formed by the reaction of sodium thioglycollate and a benzyl halide B. The benzyl thioacetic acid C is then oxidized with 30% hydrogen peroxide to give a corresponding benzylsulfonyl acetic acid D. Condensation of the benzylsulfonyl acetic acid D with an aromatic aldehyde E via a Knoevenagel reaction in the presence of benzylamine and glacial acetic acid yields the desired (E)-styryl-3-nitrobenzylsulfone F. The (E)-styryl-3-nitrobenzylsulfone F is then reduced via either palladium catalyzed hydrogenation with hydrazine hydrate as the hydrogen source or with $Na_2S_2O_4$, and subsequently alkylated to give the desired (E)-styryl-3-aminobenzylsulfone IIIa.

Scheme 1:

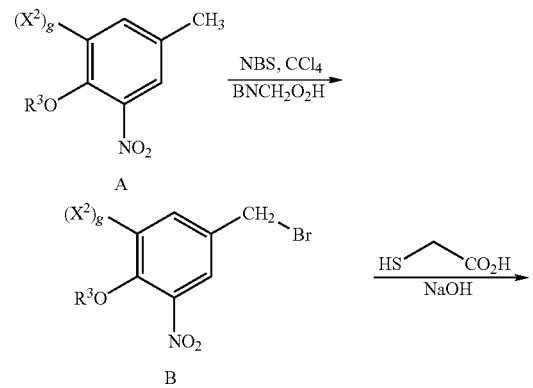

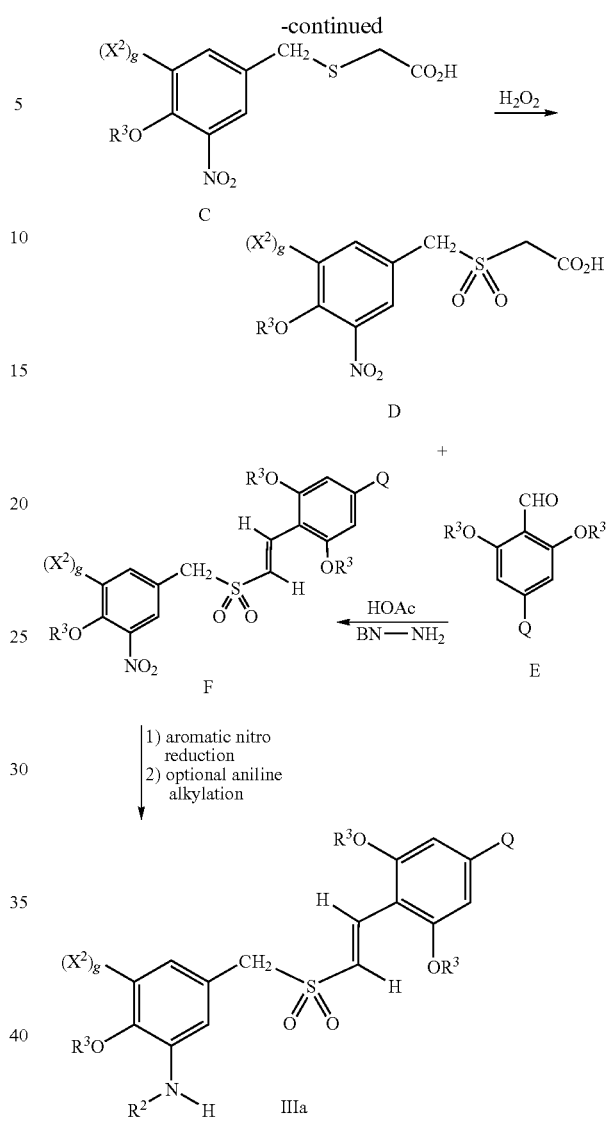

The following is a more detailed two-part synthesis procedure for preparing (E)-styryl benzylsulfone intermediates according to the above scheme.

General Procedure 1: Synthesis (E)-Styryl Benzylsulfones

Part A. To a solution of sodium hydroxide (8 g, 0.2 mol) in methanol (200 mL), thioglycollic acid (0.1 mol) is added slowly and the precipitate formed is dissolved by stirring the contents of the flask. Then an appropriately substituted benzyl halide (0.1 mol) is added stepwise and the reaction mixture is refluxed for 2-3 hours. The cooled contents are poured onto crushed ice and neutralized with dilute hydrochloric acid (200 mL). The resulting corresponding benzylthioacetic acid (0.1 mol) is subjected to oxidation with 30% hydrogen peroxide (0.12 mol) in glacial acetic acid (125 mL) by refluxing for 1 hour. The contents are cooled and poured onto crushed ice. The separated solid is recrystalized from hot water to give the corresponding pure benzylsulfonylacetic acid, D.

Part B. A mixture of the benzylsulfonyl acetic acid (10 mmol), an appropriately substituted aromatic aldehyde, E (10 mmol), and benzylamine (200 mL) in glacial acetic acid (12 mL) is refluxed for 2-3 hours. The contents are cooled and treated with cold ether (50 mL). Any product precipitated out is separated by filtration. The filtrate is diluted with more ether and washed successively with a saturated solution of sodium bicarbonate (20 mL), sodium bisulfite (20 mL), dilute hydrochloric acid (20 mL) and finally with water (35 mL). Evaporation of the dried ethereal layer yields styryl benzylsulfones as a solid material.

According to an alternative to Part A, the appropriate benzylsulfonylacetic acids may be generated by substituting a thioglycollate $HSCH_2COOR$ for thioglycollic acid, where R is an alkyl group, typically ($C_1$-$C_6$) alkyl. This leads to the formation of the alkylbenzylthioacetate intermediate (H),

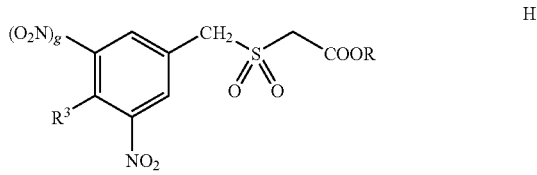

which is then converted to the corresponding benzyl thioacetic acid B by alkaline or acid hydrolysis.

The styryl benzyl-3-aminosubstituted sulfones of the present invention are prepared via several synthetic reactions from a common styryl benzyl-3-amino sulfone of formula IIIa. These reactions generally involve the coupling of the nucleophilic aniline nitrogen of compounds of formula IIIa with electrophilic moieties. For example, reaction with activated acids such as acid chlorides will yield amides of formula IV, as depicted in Scheme 2, below. Synthetic procedures for this type of coupling are provided in Examples 2, 5, 9 and 10 below.

Scheme 2:

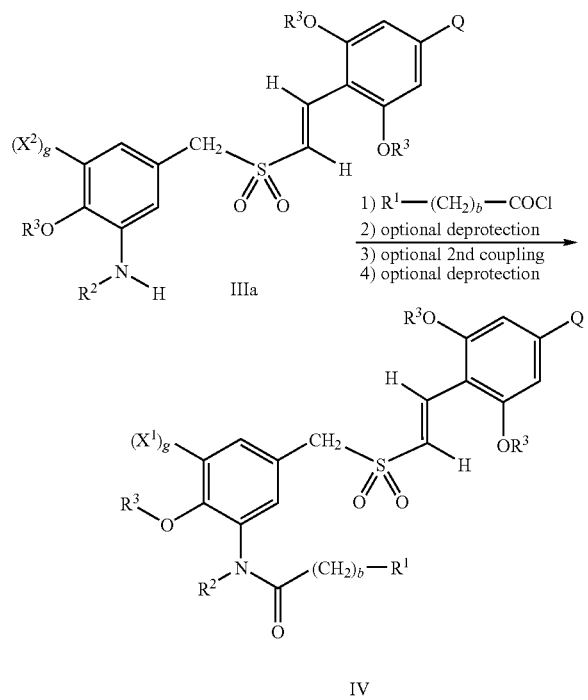

Additional carboxamide compounds of formula V may be prepared by coupling intermediates of formula IIIa with unactivated carboxylic acid moieties using a coupling agent such as diisopropyl carbodiimide, as depicted in Scheme 3, below. Detailed procedures for this type of coupling are provided in Examples 13, 14 and 15. In Scheme 3, $R^a$ is selected from: —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, —$CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2CH_3$; and includes compounds wherein $R^a$ and $R^1$ combine to form a 5- or 6-membered heterocyclic ring. Examples of heterocyclyl rings in this context include pyrrolidine, hydroxypyrrolidine, thiazolidine, piperidine and homopiperidine.

Scheme 3:

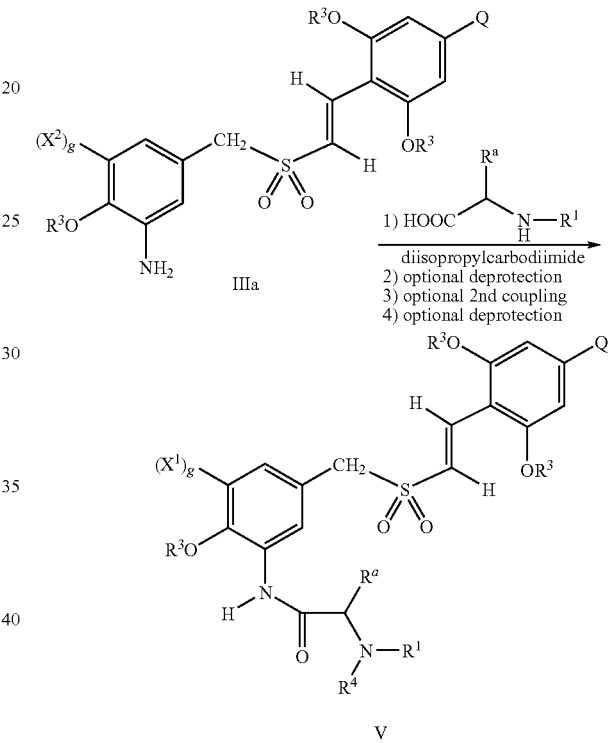

In a similar reaction, coupling of intermediates of formula IIIa with sulfonyl halides yields the corresponding sulfonamido compounds of formula VI, as shown in Scheme 4, below. A synthetic procedure for this type of coupling is provided in Example 1.

Scheme 4:

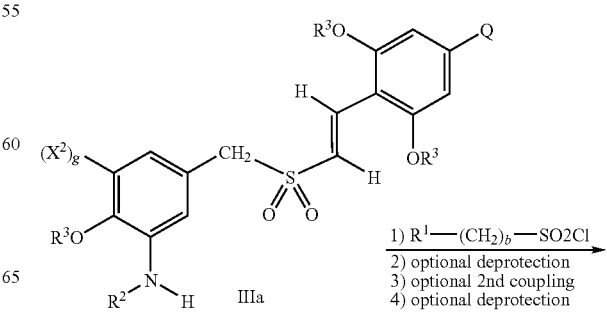

-continued

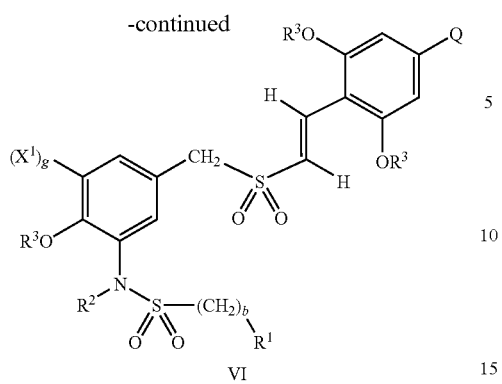

VI

Coupling of compounds of formula IIIa using 2-chloro-1-methylpyridinium iodide (Mukaiyama reagent) yields guanidine derivatives of formula VII, as shown in Scheme 5, below. A synthetic procedure for this coupling is provided in Example 3.

Scheme 5:

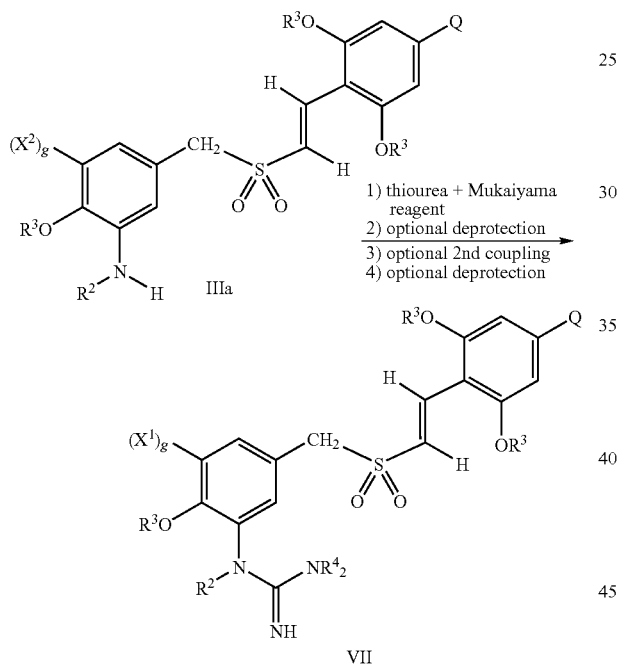

VII

The aniline nitrogen of formula IIIa may also be coupled with sp³ hybridized, alkyl halide moieties to form secondary or tertiary amines of general formula VIII, as depicted in Scheme 6, below. A synthetic procedure for this type of coupling is provided in Example 4.

Scheme 6:

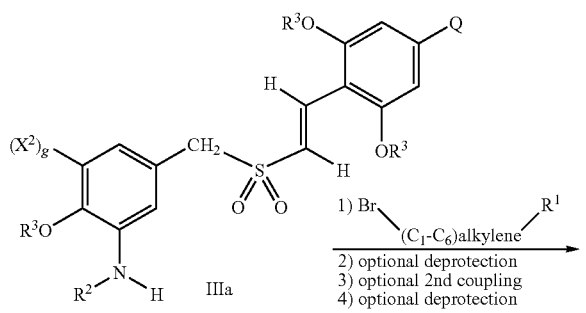

-continued

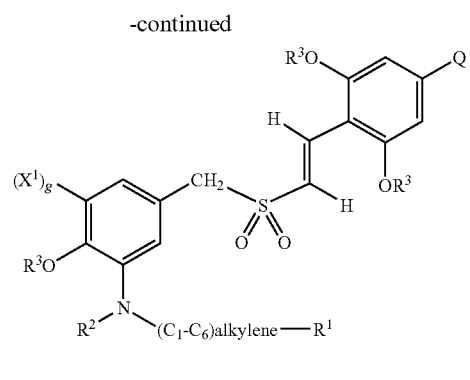

VIII

The aniline nitrogen of compounds of formula IIIa may also be coupled with aldehydes or ketones, or hydrates thereof, to form imines of formula IX as shown in Scheme 7, below. A synthetic procedure for this type of coupling is provided in Example 12.

Scheme 7:

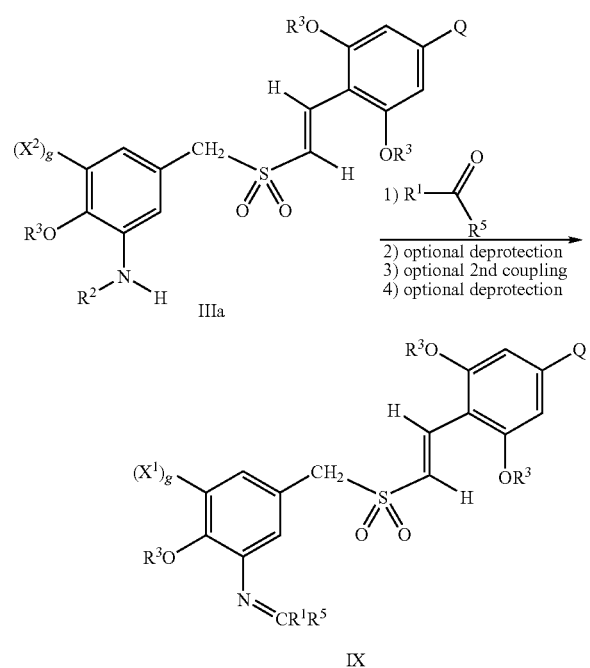

IX

The aniline nitrogen of compounds of formula IIIa can also be reacted to form the corresponding urea moieties of formula X. As depicted in Scheme 8, below, the unsubstituted urea may be formed by reaction of compounds of formula III with potassium cyanate. Ureas substituted at the distal nitrogen may be prepared as shown in Scheme 8, by reaction of compounds of formula IIIa with N-substituted carbamyl halides. In addition, reaction with substituted cyanate moieties will yield monosubstituted ureas. A synthetic procedure for this type of coupling is provided in Example 16.

Scheme 8:

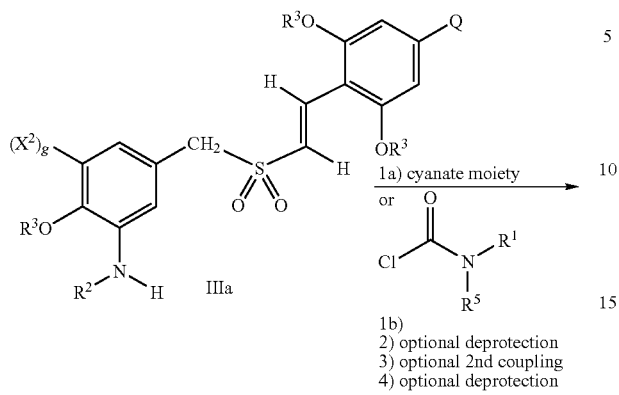

1a: R¹ = R⁵ = —H;
1b: R⁵ = —H or —(C₁-C₆)alkyl

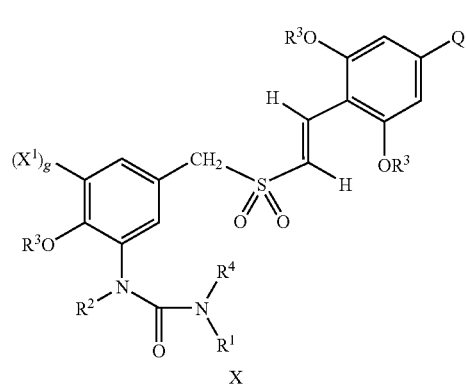

The aniline nitrogen of compounds of formula IIIa can also be reacted to form amino acid derivatives of formula XX, wherein the aniline nitrogen of IIIa is the alpha-amino moiety of an amino acid. As depicted in Scheme 9, below, these amino acid derivatives may be formed by reacting a compound of formula III with a carboxylic acid having a leaving group alpha to the carboxylate. For example; the starting carboxylate for the compound of Example 4 is methyl bromoacetate. Example 22 is another compound wherein the aniline nitrogen is derivatized as an amino acid (alanine).

Scheme 9:

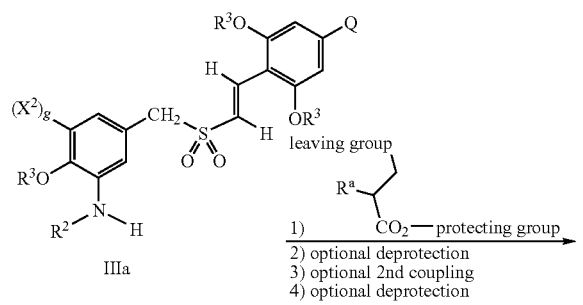

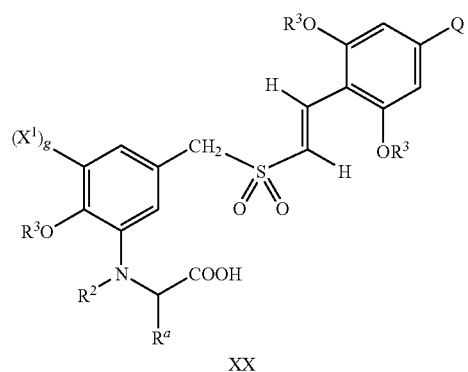

In one particular deprotection, the salt of carboxylic acid compounds of formula XX, preferably an alkali metal salt, more preferably a sodium salt is formed by hydrolysis of the carboxylic ester derivative in an aqueous base, as depicted in Scheme 10 below. This method is described in more detail in Example 4a.

Scheme 10:

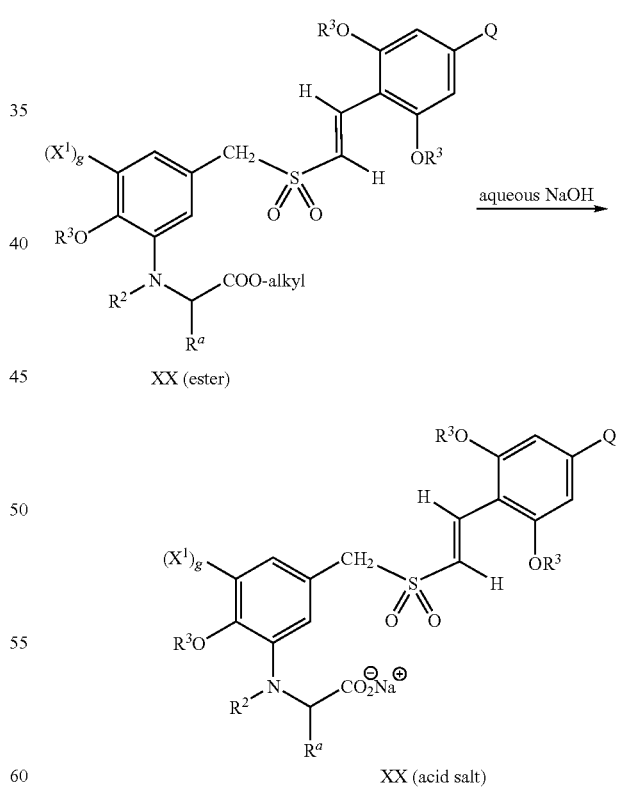

The styryl benzylsulfone compounds of the present invention may be derivatized with a chemical group to permit conjugation to a carrier molecule, for the purpose of raising antibodies to the styryl sulfones. Suitable derivatizing chemistries are well known to those skilled in the art. Preferably, the derivative comprises a carboxylic acid derivative. The carrier may comprise any molecule sufficiently large to be capable of generating an immune response in an appropriate host animal. One such preferred carrier is keyhole limpet haemocyanin (KLH). Additionally, $R^1$ structural components (such as peptidyl substituents) of compounds of the present invention can themselves provide antigenic activity sufficient to raise antibodies to the styryl sulfones.

Antibodies, preferably monoclonal antibodies and monospecific polyclonal antibodies, and most preferably tumor-specific antibodies may be covalently linked to compounds of the present invention. By "tumor-specific antibody" is meant, an antibody which specifically binds to a tumor antigen, e.g., an antigen on a tumor cell.

The covalent linker between a compound of formula I or formula III and an antibody may in its simplest form, comprise a single covalent bond connecting the compound of formula I to the antibody. More commonly the compound of formula I is attached to the antibody using a suitable bifunctional linking reagent. The term "bifunctional linking reagent" refers generally to a molecule that comprises two reactive moieties which are connected by a spacer element. The term "reactive moieties" in this context, refers to chemical functional groups capable of coupling with an antibody or a compound of formula I by reacting with functional groups on the antibody and the compound of formula I or of formula III.

An example of a covalent bond formed as a linker between a compound of formula I or formula III and an antibody is a disulfide bond formed by the oxidation of an antibody and a compound of formula I (or of formula III), wherein $R^1$ is a peptidyl moiety containing one or more cysteine amino acids. The cysteine residues can be oxidized to form disulfide links by dissolving 1 mg of the a suitable compound of formula I (or formula III) and 0.5 equivalents of the desired antibody in 1.5 ml of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified by HPLC.

Another example of a suitable covalent bond formed as a linker between a compound of formula I (or formula III) and an antibody is an amide bond formed by reacting an amino group on a compound of the invention (including a compound of formula III wherein X is $—NH_2$ (i.e., wherein X is formula (i), y is 0, $R^1$ is —H and $R^2$ is —H) as well as amino moieties on -M- bivalent connecting groups or on peptidyl $R^1$ substituents such as, for example, a lysine sidechain) with a carboxylic acid group which forms part of the primary structure of the antibody (Ab) (such as, for example a glutamic or aspartic amino acid residue). Alternatively, an amide bond could be formed if the reacting moieties were reversed, i.e., the compound of formula I could contain a carboxylic acid functionality and react with an amino functionality within the Ab structure.

Alternatively, a compound of formula I (or of formula III) and an antibody Ab may be covalently linked using a bifunctional linking reagent. In one such embodiment of the present invention, a compound of formula I (or formula III) wherein $R^1$ is a peptidyl moiety is coupled to an antibody using a bifunctional linking reagent. In another such embodiment a compound of formula I (or formula III) wherein X is $—NH_2$ (ie., X is formula (i), y is 0 and $R^1$ and. $R^2$ are both —H) is coupled to an antibody.

For example, adducts can be prepared by first preparing S—(—N-hexylsuccinimido)-modified derivatives of an antibody and of a compound of formula I, according to the method of Cheronis et al., *J Med. Chem.* 37: 348 (1994)(the entire disclosure of which is incorporated herein by reference). N-hexylmaleimide, a precursor for the modified antibody and compound of formula I, is prepared from N-(methoxycarbonyl)maleimide and N-hexylamine by mixing the two compounds in saturated $NaHCO_3$ at 0° C. according to the procedure of Bodanszky and Bodanszky, *The Practice of Peptide Synthesis;* Springer-Verlag, New York, pp. 29-31 (1984)(the entire disclosure of which is incorporated herein by reference). The product of the resulting reaction mixture is isolated by extraction into ethyl acetate, followed by washing with water, dried over $Na_2SO_4$, and is then concentrated in vacuo to produce N-hexylmaleimide as a light yellow oil. S—(N-Hexylsuccinimido)-modified antibody and formula I compound are then prepared from a cysteine-containing peptide and N-hexylmaleimide by mixing one part peptide with 1.5 parts N-hexylmaleimide in dimethylformamide (3.3 mL/mM peptide) followed by addition to 30 volumes of 0.1 M ammonium bicarbonate, pH 7.5. The S-alkylation reaction carried out in this manner is complete in 30 min. The resulting S-(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is a formula I compound wherein $R^1$ is a peptidyl moiety), may be prepared according to the method of Cheronis et al., supra from cysteine-substituted peptides. A mixture of one part bismaleimidohexane is made with two parts peptide monomer in dimethylformamide (3.3 mL/mM peptide) followed by addition to 0.1 ammonium bicarbonate, pH 7.5. The reaction mixture is stirred at room temperature and is usually completed within 30 min. The resulting bis-succinimidohexane peptide dimer is purified by preparative reverse-phase HPLC. After lyophilization the material is a fluffy, white powder.

Covalently linked adducts of the general formula I-L-Ab of the present invention, or of the formula III-L-Ab when coupling to a compound of formula III, may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4cinitrobenzene ("DFNB"), 4,4'-diisothiocyano-2,2'-disulfonic acid stilbene ("DIDS"), and bis-maleimidohexane ("BMH"). The linking reaction occurs randomly between the Ab and a compound of formula I having a peptidyl moiety as $R^1$.

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sutfo-SMPB"), bromoacetyl-p-aminobenzoyl-N-hydroxy-succinimidyl ester, iodoacetyl-N-hydroxysuccinimidyl ester, and the like.

For hetero-bifunctional linking, a compound of formula I (or a compound of formula III) is derivatized with, for example, the N-hydroxysuccinimidyl portion of the bifunctional reagent, and the resulting derivatized compound is purified by chromatography. Next, a suitable tumor-specific Mab is reacted with the second functional group of the bifunctional linking reagent, assuring a directed sequence of binding between components of the desired adduct Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the Mab or the formula I compound (or formula III compound) are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either a Mab or to a formula I compound wherein $R^1$ is a peptidyl moiety, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyeidyldithio)-propionate (SPDP), 2-iminothiolane (2-IT), 3-(4-carboxamidophenyidithio)propionthioimidate (CDPT), N-succinimidyl-acetylthioacetate (SATA), ethyl-S-acetyl-propionthioimidate (AMPT) and N-succinimidyl-3-(4carboxamidophenyldithio)propionate (SCDP). Procedures for preparation of immunoconjugates using these linkers is detailed in *Toxin-Targeted Design for Anticancer Therapy; II: Preparation and Biological Comparison of Different Chemically Uinked Gelonin-Antibody Conjugates* (Cattel, et al, *J. Pharm. Sci.*, 82:7, p 699-704, 1993), (the entire disclosure of which is incorporated herein by reference).

According to one embodiment of the invention the antibody comprises a tumor-specific antibody, more preferably a tumor-specific monoclonal antibody or a tumor-specific monospecific polyclonal antibody.

Monoclonal antibodies may be advantageously cleaved by proteolytic enzymes to generate fragments retaining the antigen-binding site. For example, proteolytic treatment of IgG antibodies with papain at neutral pH generates two identical so-called "Fab" fragments, each containing one intact light chain disulfide-bonded to a fragment of the heavy chain (Fd). Each Fab fragment contains one antigen-combining site. The remaining portion of the IgG molecule is a dimer known as "Fc". Similarly, pepsin cleavage at pH 4 results in the so-called $F(ab')_2$ fragment.

Methods for preparation of such fragments are known to those skilled in the art See, Goding, *Monoclonal Antibodies Principles and Practice,* Academic Press (1983), p. 119-123. Fragments of the anti-DBF-MAF monoclonal antibodies containing the antigen binding site, such as Fab and $F(ab')_2$ fragments, may be preferred in therapeutic applications, owing to their reduced immunogenicity. Such fragments are less immunogenic than the intact antibody, which contains the. immunogenic Fc portion.

The effects of sensitization in the therapeutic use of animal origin monoclonal antibodies in the treatment of human disease may be diminished by employing a hybrid molecule generated from the same Fab fragment, but a different Fc fragment, than contained in Mab's previously administered to the same subject. It is contemplated that such hybrid molecules formed from the monoclonal antibodies of the invention may be used in therapy. The effects of sensitization are further diminished by preparing animal/human chimeric antibodies, e.g., mouse/human chimeric antibodies, or humanized (ie. CDR-grafted) antibodies. Such monoclonal antibodies comprise a variable region, i.e., antigen binding region, and a constant region derived from different species.

Chimeric animal-human monoclonal antibodies may be prepared by conventional recombinant DNA and gene transfection techniques well known in the art The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci. USA* 81, 6851-6855, 1984, both chimeric heavy chain V region exon $(V_H)$-human heavy chain C region genes and chimeric mouse light chain V region exon $(V_K)$-human K light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642-646, 1984. Also see Tan et al., *J. Immunol.* 135, 3564-3567, 1985 for a description of high level expression from a human heavy chain promoter of a human-mouse chimeric K chain after transfection of mouse myeloma cells. As an alternative to combining genomic DNA, cDNA clones of the relevant V and C regions may be combined for production of chimeric antibodies, as described by Whitte et al., *Protein Eng.* 1, 499-505, 1987 and Liu et al., *Proc. Natl. Acad. Sci. USA* 84, 3439-3443, 1987.

For examples of the preparation of chimeric antibodies, see the following U.S. Pat. Nos. 5,292,867; 5,091;313; 5,204, 244; 5,202,238; and 5,169,939. The entire disclosures of these patents, and the publications mentioned in the preceding paragraph, are incorporated herein by reference. Any of these recombinant techniques are available for production of rodenvhuman chimeric anti-DBP-MAF monoclonal antibodies.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al, *Nature* 321, 522-525, 1986; Verhoeyen et al, *Science* 239, 1534-1536, 1988; Reichmann et al, 322, 323-327, 1988; Hale et al., *Lancet* 2, 1394-1399, 1988; Queen et al., *Proc. Nati. Acad. Sci. USA* 86, 10029-10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodentthuman antibodies of reduced human immunogeneicity.

Several such monoclonal antibodies, chimeric animal-human monoclonal antibodies, humanized antibodies and antigen-binding fragments thereof have been made available. Some examples include:

Satumomab Pendetide (by Cytogen, a murine Mab directed against TAG-72);

Igovomab (by CIS Bio, a murine Mab fragment Fab$_2$ directed against tumor-associated antigen CA 125);

Arcitumomab (by Immunomedics, a murine Mab fragment Fab directed against human carcinoembryonic antigen CEA);

Capromab Pentetate (by Cytogen, a murine Mab directed against tumor surface antigen PSMA);

Tecnemab KI (by Sorin, murine Mab fragments (Fab/Fab$_2$ mix) directed against HMW-MAA);

Nofetumomab (by Boehringer Ingelheim/NeoRx, murine Mab fragments. (Fab) directed against carcinoma-associated antigen);

Rituximab (by Genentech/IDEC Pharmaceuticals, a chimeric Mab directed against CD20 antigen on the surface of B lymphocytes);

Trastuzumab (by Genintech, a humanized antibody directed against human epidermal growth factor receptor 2 (HER 2));

Votumumab (by Organon Teknika, a human Mab directed against cytokeratin tumor-associated antigen);

Ontak (by Seragen/Ligand Pharmaceuticals, an IL-2-diphtheria toxin fusion protein that targets cells displaying a surface IL-2 receptor);

IMC-C225 (by lmclone, a chimerized monoclonal antibody that binds to EGFR);

LCG-Mab (by Cytoclonal Pharmaceutics Monoclonal antibody directed against lung cancer gene LCG)

ABX-EGF (by Abgenix, a fully human monoclonal antibody against the epidermal growth factor receptor (EGFr)); and Epratuzumab (by lmmunomedics, a humanized, anti-CD22 monoclonal antibody).

Hence, compounds of formula I can readily be covalently bonded to antibodies, preferably tumor-specific monoclonal antibodies (Mab) via a suitable bifunctional linker (-L-) to yield a conjugate of general formula, I-L-Ab. In addition, compounds of formula III can be covalently bonded to antibodies (Ab), preferably tumor-specFifc monoclonal antibodies (Mab) via a suitable bifunctional linker (-L-) to yield a conjugate of general formula, III-L-Ab. A general synthetic route for preparing compounds of the present invention of general formula I-L-Ab or of formula III-L-Ab, is depicted below in Scheme 11.

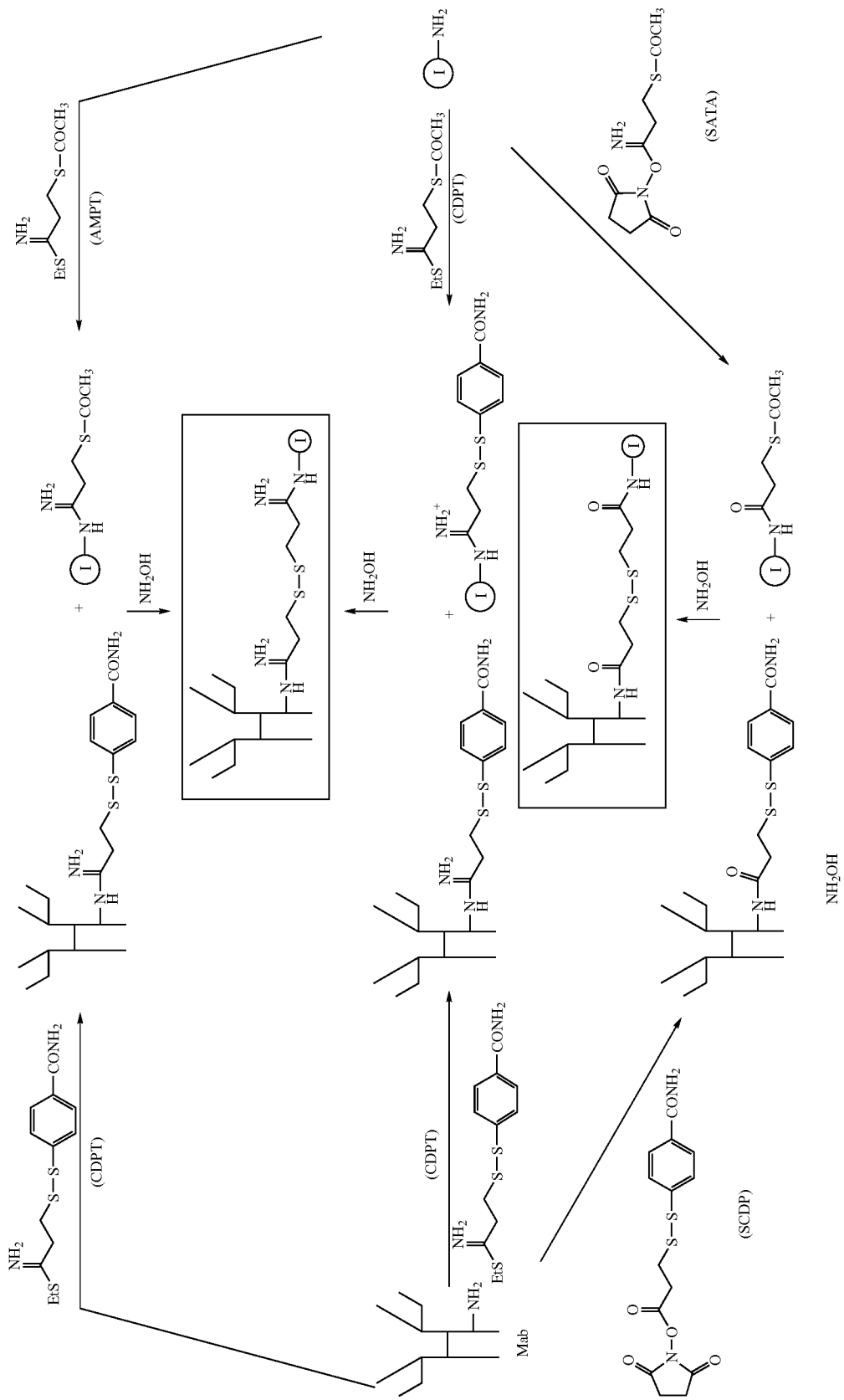
Scheme 11

In a variation of this strategy, antibody-directed enzyme prodrug therapy (ADEPT) comprises administration of tumor-specific monoclonal antibodies to localize not the drug itself, but rather, an enzyme such as a β-lactamase to the tumor site. Then, cytotoxic compound according to the present invention, is appropriately derivatized into a prodrug designed to be a substrate to the β-lactamase. The prodrug is administered to the patient and a compound of formula I is released only when the prodrug reaches the tumor site and is bound to the tumor-localized enzyme. In a preferred embodiment, the prodrug is less cytotoxic than the β-lactamase-released drug, such that the therapeutic index of the prodrug is substantially elevated over that of the free drug. This is because the enzyme-released cytotoxic drug is effectively localized to the tumor site where the free drug is released on exposure to the tumor-localized lactamase enzyme.

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonici stearic, alginic, beta-hydroxybutyric, salicylic, galactaric and galacturonic acid. Examples of pharmaceutically unacceptable acid addition salts include perchlorates and tetrafluoroborates.

Suitable pharmaceutically acceptable base addition salts of compounds of formula I include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. Examples of pharmaceutically unacceptable salts include lithium salts. All of these salts may be prepared by conventional means from the corresponding compound of formula I by reacting, for example, the appropriate acid or base with the compound of formula I.

It will be understood that when compounds of the present invention contain one or more chiral centers, the compounds may exist in, and may be isolated as pure enantiomeric or diastereomeric forms or as racemic mixtures. The present invention therefore includes any possible enanbomers, diastereomers, racemates or mixtures thereof of Formula I which are biologically active in the treatment of cancer or other proliferative disease states.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate, but do not escape normal position controls (i.e., have no metastatic potential). Such disorders include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocysfic disease (e.g., of the breast or uterus); sarcoidosis; Peyronie's fibrosis, Dupuytren's fibrosis, cirrhosis, atherosclerosis and vascular restenosis.

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical, sublingual or subcutaneous administration. Also contemplated within the scope of the invention is the instillation of drug in the body of the patient in a controlled formulation, with systemic or local release of the drug to occur at a later time. For example, the drug may be localized in a depot for controlled release to the circulation, or for release to a local site of tumor growth.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar soluions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include for example, sulfite, ascorbic acid, citric acid and its salts, and sodium EDTA. Suitable preservatives include for example, benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wefting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples. In each of the following examples, the substituted benzylsulfonyl acetic acid was made according to Part A of General Procedure 1: Synthesis (E)-Styryl Benzylsulfones, above. The styryl benzylsulfone compounds were recrystalized from 2-propanol and the purity was checked by thin layer chromatography.

Synthesis of (E)-24.6-Trimethoxystyryl-3-Amino-4-Methoxybenzyl Sulfone

Step 1: Preparation of 4-Methoxy-3-Nitro benzylbromide:

A solution of 4-methyl-2-nitroanisole (25 mmol), N-bromosuccinimide (25 mmol) and benzoyl peroxide (2.5 mmol) in carbon tetrachloride (100 mL) was heated at reflux for 18 h. The reaction mixture was then poured into water and solid separated was filtered. The aqueous layer was extracted with carbon tetrachloride (3×50 mL) and organic phase was separated and evaporated to give a solid product. The solid products were combined and recrystallized from ethyl acetate-hexane to give a crystalline product of 3-nitro-4-methoxy benzyl bromide. m.p. 110-112° C., yield 70-75%.

Step 2: Synthesis of 4-Methoxy-3-Nitrobenzylthioacetic acid:

To a cold solution of sodium hydroxide (9.75 g, 240 mmol) in methanol (200 mL), thioglycollic acid (11.25 g, 120 mmol) was added slowly over 30 minutes. Sodium thioglycollate precipitated was dissolved by stirring and warming up the solution. The solution was cooled to room temperature and 4-methoxy-3-nitrobenzyl chloride (30.0 g, 120 mmol) was added in portions to reduce the intensity of exothermic reaction. The reaction mixture was then refluxed for 4 hours, cooled and poured onto crushed ice (1 Kg) containing hydrochloric acid (50 mL). The precipitate formed was filtered, washed with ice cold water and dried under vacuum. (30.0 g, 95% yield) m.p. 130-132° C.

Step 3: Synthesis of 4-Methoxy-3-Nitrobenzylsulfonylacetic acid:

4-Methoxy-nitrobenzylthioacetic acid (10 g) was dissolved in glacial acetic acid (80 mL) and 30% hydrogen peroxide (20 mL) was added in one portion and the mixture was stirred at room temperature for 10 hours. The contents of the flask were cooled and poured on to crushed ice (500 g). A yellow precipitate formed, and was filtered, washed with cold water and dried (55% yield). Recrystallization from hot water yielded crystals of 4-methoxy-3-nitrobenzylsulfonyl acetic acid. m.p. 96-98° C.

Step 4: Synthesis of (E)-2,4,6-Trimethoxystyryl-4-Methoxy-3-Nitrobenzylsulfone:

A solution of 4-methoxy-3-nitrobenzyl sulfonylacetic acid (4.5 g, 15.5 mmol) in 30 mL of glacial acetic acid was treated with 2,4,6-trimethoxybenzaldehyde (3.05 g, 15.5 mmol) in the presence of catalytic amounts of benzylamine (0.6 mL). The reaction mixture was refluxed for 6 hours and acetic acid was removed under vacuum. The gummy material obtained was treated with 2-propanol to yield a solid product which was recrystallized from a mixture of acetic acid and 2-propanol. Yield 28%, m.p. 186-187° C.

Step 5: Reduction of (E)-2,4,6-Trimethoxystyryl-4-Methoxy-3-Nitrobenzylsulfone:

Method 1

Synthesis of (E)-2,4,6-Trimethoxystyryl-4-Methoxy-3-Aminobenzylsulfone:

A solution of (E)-2,4,6-trimethoxystyryl-4-methoxy-3-nitrobenzylsulfone (1.3 mmol) in acetone-water (10:5) was heated to 50° C. After 30 min, sodium hydrosulfite ($Na_2S_2O_4$) (26.3 mmol) was added slowly, and the mixture was heated at reflux (50° C., 1 h.), cooled to room temperature and water was added. The product was rinsed with $NaHCO_3$, and then isolated by extraction with ethyl acetate. The organic layer was dried over anhydrous $Na_2SO_4$. The solvent was removed under reduced pressure and the crude product was recrystallized from 2-propanol, m.p. 148-150° C.

The reduction of (E)-2,4,6-trimethoxystyryl-4-methoxy-3-nitrobenzylsulfone to (E)-2,4,6-trimethoxystyryl-4-methoxy-3-aminobenzylsulfone was also performed by the following method.

Reduction of (E)-2,4,6-Trimethoxystyryl-4-methoxy-3-nitrobenzylsulfone: Method 2:

5% Pd/C wet (10% by weight of the nitro compound) was charged into a flask. Pd/C was wetted with ethanol by slowly adding through the sides of the flask. The nitro compound (10 mmol) is added to the flask and then 20 volume equivalents of ethanol is added. The temperature of the flask was raised to 50-60° C. Then hydrazine hydrate (26 equivalents) is added over a period of 15-20 min. It is then refluxed for 5-6 hours. The completion of the reaction was monitored every hour by TLC. After completion of the reaction, Pd/C was filtered while the solution was hot and the filtrate was washed with 2 volumes of hot ethanol. The volume of ethanol was reduced to 50% by distilling under reduced pressure and 10 volumes of ice cold water was added. The solution was stirred for 30 min and the precipitated solid was filtered and dried under vacuum and recrystallized from 2-propanol to give 2,4,6-trimethoxystyryl-4-methoxy-3-aminobenzylsulfone, m.p. 148-150° C.

General Method A: Synthesis of (E)-2,4,6-Trimethoxystyryl-3-amino-substituted-4-methoxybenzylsulfone derivatives A solution of 1-chlorocarbonyl ester (10 mmol) and triethylamine (10 mmol) in dichloromethane (40 mL) was stirred for 10 min. at room temperature. (E)-2,4,6-trimethoxystyryl-3-amino-4-methoxybenzylsulfone (10 mmol) in dichloromethane (20 mL) was added dropwise. The resulting mixture was stirred at room temperature overnight. The organic layer was separated, washed with water and dried over anhydrous sodium sulfate. Volatiles were removed under vacuum to give the product ester in 80% yield.

The ester (1 g) was taken up in 4% aqueous sodium hydroxide (50 mL) and stirred at room temperature for 3 hours. Subsequently, concentrated hydrochloric acid was added dropwise until a solid precipitate formed. The precipitate was separated by filtration, washed with water and recrystallized from 2-propanol to give the desired product.

General Method B: Synthesis of (E)-2,4,6-Trimethoxystyryl-3-Aminosubstituted-4-Methoxybenzylsulfone Derivatives.

Sodium acetate (0.4 mol) was dissolved in methanol (200 mL). An alkyl halide (0.4 mol) was added and the resulting mixture was refluxed for 10 minutes. The mixture was cooled to room temperature and (E)-2,4,6-trimethoxystyryl-3-amino-4-methoxybenzylsulfone (0.1 mol) was added. The resulting mixture was heated to reflux for 1 hour. The reaction mixture was then concentrated the residue was poured to ice water. A solid precipitate formed. The precipitate was separated by filtration and recrystallized from ethanol to give the desired amino substituted ester.

The ester compound (0.1 mol) was taken up in ethanol (200 mL) and sodium hydroxide (20% aqueous solution, 200 mL) was added. The reaction mixture was refluxed for 2.5 hours. When the reaction was complete, the volatiles were removed under vacuum and the residue was acidified to pH 4 by addition of acetic acid. A solid precipitate formed which was separated by filtration. The filtered solid was recrystallized twice from acetone twice to give the desired (E)-2,4,6-trimethoxystyryl-3-substituted-4-methoxybenzyl sulfone.

EXAMPLE 1

(E)-2,4,6-Trimethoxystyryl-3-(carboxymethylsulfamyl)-4-methoxybenzylsulfone

A solution of (E)-2,4,6-trimethoxystyryl-3-amino-4-methoxybenzylsulfone (10 mmol) and triethylamine (10 mmol) in dichloromethane was stirred at room temperature for 15 min. To this, a solution of methyl chlorosulfonylacetate (10 mmol) was added drop wise and stirring was continued for three more hours. After completion of the reaction which was monitored by TLC water was added and stirred the solution for about 15 min. The organic layer was separated, dried and passed through a column to obtain 2,4,6-trimethoxystyryl-3-(methoxycarbonylmethanesufamyl)-4-methoxybenzylsulfone.

The ester (1 g) was made as an aqueous sodium hydroxide suspension and stirred vigorously for 3h at room temperature. Then the solution was brought to 0-5° C. and concentrated hydrochloric acid was added fill the pH of the solution attains 3. The white solid precipitated out, was filtered, dried and recrystallized to give (E)-2,4,6-trimethoxystyryl-3-carboxymethyl sulfamyl-4-methoxybenzylsulfone in 70% yield, m.p. 180-184° C. NMR (DMSO-d6) δ 3.88 (s, 3H), 3.92 (s, 6H), 4.4 (s, 2H), 6.0(s, 2H), 7.25(d, 1H vinylic), 7.11-7,36 (m, aromatic), 8.2 (s, 1H)

EXAMPLE 2

(E)-2,4,6-Trimethoxystyryl-3-(carboxyacetamido)-4-methoxybenzylsulfone

A solution of methyl-3-chloro-3-oxopropionate (10 mmol), and triethylamine (10 mmol) in dichloromethane (40 mL) was stirred in RB flask for 10 min. at room temperature and then 2,4,6-trimethoxystyryl-3-amino-4-methoxybenzylsulfone (10 mmol) in dichloromethane (20 mL) was added dropwise into the flask. The contents of the flask were stirred overnight and the organic layer was washed with water and dried over anhydrous sodium sulfate. Evaporation of dichloromethane under vacuum gave the ester in 80% yield, m.p. 190-193° C. The ester (1 g) was taken in a flask and 4% aqueous sodium hydroxide (50 mL) was added to the flask. The contents of the flask were stirred at room temperature for 3 h and conc. hydrochloric acid was added dropwise till a precipitate is formed. The precipitate was filtered, washed with water and recrystallized from.,2-propanol to give (E)-2,4,6-trimethoxystyryl-3-(carboxyacetamido)-4-methoxybenzylsulfone in 70% yield, m.p. 118-121° C. NMR (DMSO-d6) δ 3.78 (s, 3H), 3.82 (s, 6H), 3.86 (s, 3H), 4.2 (s, 2H), 6.1 (s, 2H), 7.1 (d, 1H vinylic), 7.15-7,26 (m, aromatic), 8.5 (s, 1H)

EXAMPLE 3

(E)-2,4,6-Trimethoxystyryl-3-(guanidino)-4-methoxybenzylsulfone

Step 1: Synthesis of 2,4,6-trimethoxystyryl-3-(di-tert-butoxyguanidino)-4-methoxybenzylsulfone:

To a solution of 2,4,6-trimethoxystyryl-4-methoxy-3-aminobenzylsulfone (10 mmol), N,N-bis(tert-butoxycarbonyl)thiourea (12 mmol) and triethylamine (22 mmol) in dichloromethane (10 mL), was added Mukaiyama reagent (2-chloro-1-methylpyridinium iodide) (12 mmol). The reaction mixture was stirred at 25° C. until the completion of the reaction as monitored by TLC. Upon the completion of the reaction, the solvent was evaporated and the residue was dissolved in diethyl ether (15 mL) and washed with water. The ethereal layer was dried over anhydrous sodium sulfate and evaporated in a rotary evaporator to give 2,4,6-trimethoxystyryl-3-(di-tert-butoxyguanidino)-4-methoxybenzylsulfone in 99% yield, m.p. 100-101° C.

Step 2: Synthesis of (E)-2,4.6-trimethoxystyryl-3-(quanidino)-4-methoxybenzylsulfone:

A solution of 2,4,6-trimethoxystyryl-3-(di-tert-butoxyguanidino)-4-methoxy benzyl sulfone (1 g) was dissolved in a 1:1 mixture of dichloromethane and trifluoroacetic acid. The reaction mixture was stirred for 3 h at room temperature and the solution was concentrated under vacuum. The residue was washed and concentrated several times with diethyl ether for complete removal of trifluoroacetic acid. The residue was given a final wash with water and solid obtained was subjected to column chromatography (silica gel 70-325 mesh) and eluted with ethyl acetate: petroleum ether to yield pure (E)-2,4,6-trimethoxystyryl-3-(guanidino)-4-methoxybenzylsulfone in 40%, m.p. 174-176° C. NMR (DMSO-d6) δ 3.75(s, 3H), 3.80(s, 6H), 3.84(s, 3H), 4.15(s, 2H), 6.08(s, 2H), 7.22(d, 1H vinylic), 7.15-7,26(m, aromatic).

EXAMPLE 4

(E)-2,4,6-Trimethoxystyryl-3-(carboxymethylamino)-4-methoxybenzylsulfone

To a stirred solution of methyl bromoacetate (5 mmol) and sodium acetate (5 mmol) in methanol (20 mL) was added 2,4,6-trimethoxy-3-amino-4-methoxybenzysulfone (1 mmol) and stirring was continued under reflux temperature for 12-15 h. The contents of the flask were cooled and poured onto the ice. The resultant ester obtained (85% yield) was filtered (m.p. 182-185° C.). The ester (1 g) was dissolved in ethanol (8 mL) and 4% aqueous sodium hydroxide (50 mL) and refluxed for 10 min to get a clear solution. The contents of the flask were then stirred at room temperature for 3 h and conc. hydrochloric acid was added dropwise until a precipitate formed. The precipitate was filtered, washed with water and recrystallized from 2-propanol to give (E)-2,4,6-trimethoxystyryl-3-(carboxymethylamino)-4-methoxybenzylsulfone in 80% yield, m.p. 128-131° C. NMR (DMSO-d6) δ 3.76(s, 3H), 3.80(s, 6H), 3.82(s, 3H), 4.23(s, 2H), 6.25(s, 2H), 7.06-7.09(d, 1H vinylic), 6.66-6.74(m, aromatic).

EXAMPLE 4a (E)-2,4,6-Trimethoxystyryl-3-carboxymethylamino-4-methoxybenzylsulfone, sodium salt The methyl ester, (E)-2,4,6-trimethoxystyryl-3-(carbomethoxymethylamino)-4-methoxybenzylsulfone (1 g) was dissolved in ethanol (8 mL) and 4% aqueous sodium hydroxide (50 mL) and refluxed for 10 min to get a clear solution. The contents of the flask were then stirred at room temperature for 3 hours and the reaction progress was monitored by TLC. When the hydrolysis was complete, the volatiles were removed under vacuum and the residue was purified by triturating with ethanol.

EXAMPLE 5

(E)-2,4,6-trimethoxystyryl-3-(3,5,-trinitrobenzamido)-4-methoxybenzylsulfone

To a solution of 3,5-dinitrobenzoyl chloride (10 mmol) in tetrahydrofuran (40 mL) was added drop wise a solution of 2,4,6-trimethoxystyryl-3-amino-4-methoxybenzylsulfone (10 mmol) in tetrahydrofuran. The solution was stirred overnight and the completion of the reaction was monitored by TLC. The solvent was removed and the residue was taken up in dichloromethane and washed with water. The organic layer was dried over anhydrous sodium sulfate and evaporated to give (E)-2,4,6-trimethoxystyryl-3-(3,5-dinitrobenzamido)-4-methoxybenzylsulfone in 80% yield (m.p. 277-279° C.). NMR (DMSO-d6) δ 3.80 (s, 3H), 3.82(s, 6H), 3.86(s, 3H), 4.35(s, 2H), 6.3(s, 2H), 7.15-9.1(m, aromatic+vinylic), 9.8(s, 1H).

EXAMPLE 6

(E)-2,4,6-trimethoxystyryl-3-(3,5,diaminobenzamido)-4-methoxybenzylsulfone

A solution of 2,4,6-trimethoxystyryl-3-(3,5-dinitrobenzamido)-4-methoxybenzylsulfone (example 5) (1.3 mmol) in acetone water (10:5) was heated to 50° C. After 30 min, sodiumhydrosulfite ($Na_2S_2O_4$) (26.3 mmol) was added slowly, and the mixture was heated at reflux (50° C., 1 h.), cooled to room temperature and water was added. The product was rinsed with $NaHCO_3$, and then isolated by extraction with ethyl acetate. The organic layer was dried over anhydrous $Na_2SO_4$. The solvent was removed under reduced pressure and the crude product was recrystallized from 2-propanol to yield pure (E)-2,4,6-trimethoxystyryl-3-(3,5, diaminobenzamido)-4-methoxybenzylsulfone. m.p. 208-210° C. NMR (DMSO-d6) δ 3.76(s, 3H), 3.80(s, 6H), 3.82(s, 3H), 4.4(s, 2H), 5.9(s, 1H), 6.2(s, 2H), 7.05-8.26(m, aromatic), 8.85(s, 1H).

EXAMPLE 7

(E)-2,4,6-Trimethoxystyryl-3-(chloroacetamido)-4-methoxybenzylsulfone

To a solution of 2,4,6trimethoxystyryl-3-amino-4-methoxybenzylsulfone (10 mmol) in toluene, chloroacetyl chloride (10 mmol) in dioxane (10 mL) was added and the solution was refluxed for 2 h. The solution was cooled and the solvent was removed in a rotary evaporator to give 2,4,6-trimethoxystyryl-3-chloroacetamido-4-methoxybenzylsulfone in 88% yield. M.p. 163-165° C. NMR (DMSO-d6) δ 3.83(s, 3H), 3.84(s, 6H), 3.85(s, 3H), 4.14(s, 2H), 4.22(s, 2H) 6.08 (s, 2H), 7.11-7.20(d, 1H vinylic), 6.90-8.33(m, aromatic), 8.89(s, 1H).

EXAMPLE 8

(E)-2,4,6-Trimethoxystyryl-3-(4-methylpiperazinyl)]acetamido-4-methoxybenzylsulfone A solution of 2,4,6-trimethoxystyryl-3-(chloroacetamido)-4-methoxybenzyl sulfone (example 7) (10 mmol), N-methylpiperazine (10 mmol) and potassium carbonate (10 mmol) in dimethylformamide (20 mL) was refluxed for 5 h at 80° C. The reaction mixture was cooled to room temperature, and water was added. The solution was then extracted with ethyl acetate and organic layer was washed with water, brine and dried over sodium sulfate. Evaporation of the solvent in a rotary evaporator gave (E)-2,4,6-trimethoxystyryl-3-[(4-methylpiperazinyl)acetamido]-4-methoxybenzylsulfone in 87% yield. m.p. 176-178° C.

EXAMPLE 9

(E)-2,4,6-Trimethoxystyryl-3-(benzamido)-4-methoxybenzylsulfone

To a solution of benzoyl chloride (10 mmol) in tetrahydrofuran (40 mL) was added dropwise a solution of 2,4,6-trimethoxystyryl-3-amino-4-methoxybenzylsulfone (10 mmol) in tetrahydrofuran. The solution was stirred overnight and the completion of the reaction was monitored by TLC. The solvent was removed and the residue was taken up in dichloromethane and washed with water. The organic layer was dried over anhydrous sodium sulfate and evaporated to give (E)-2,4,6-trimethoxystyryl-3-benzamido-4-methoxybenzylsulfone in 76% yield. m.p. 163-166° C. NMR (DMSO-d6) δ 3.82(s, 3H), 3.83(s, 6H), 3.86(s, 3H), 4.2(s, 2H), 6.14(s, 2H), 7.10-7.18(d,1 H vinylic), 7.00-7.86(m, aromatic), 8.90 (s,1 H).

EXAMPLE 10

(E)-2,4,6-Trimethoxystyryl-3-(4-nitrobenzamido)-4-methoxybenzylsulfone

To a solution of 4-nitrobenzoyl chloride (10 mmol) in tetrahydrofuran (40 mL) was added dropwise a solution of 2,4,6-trimethoxystyryl-3-amino-4-methoxybenzylsulfone (10 mmol) in tetrahydrofuran. The solution was stirred overnight and the completion of the reaction was monitored by TLC. The solvent was removed and the residue was taken in dichloromethane and washed with water. The organic layer was dried over anhydrous sodium sulfate and evaporated to give (E)-2,4,6-trimethoxystyryl-3-(4-nitrobenzamido)-4-methoxybenzylsulfone in 72% yield. m.p. 206-208° C. NMR (DMSO-d6) δ 3.80(s, 3H), 3.81(s, 6H), 3.83(s, 3H), 4.18(s, 2H), 6.08(s, 2H), 7.14-7.23(d, 1H vinylic), 6.97-7.86(m, aromatic), 9.05(s, 1H).

EXAMPLE 11

(E)-2,4,6-Trimethoxystyryl-3-(4-aminobenzamido)-4-methoxybenzylsulfone

A solution of 2,4,6-trimethoxystyryl-3-(4-nitrobenzamido)-4-methoxybenzylsulfone (example 10) (1.3 mmol) in acetone water (10:5) was heated to 50° C. After 30 min, sodiumhydrosulfite (Na₂S₂O₄) (26.3 mmol) was added slowly, and the mixture was heated at reflux (50° C., 1 h.), cooled to room temperature and water was added. The product was rinsed with NaHCO₃, and then isolated by extraction with ethyl acetate. The organic layer was dried over anhydrous Na₂SO₄. The solvent was removed under reduced pressure and the crude product was recrystallized from 2-propanol to give pure (E)-2,4,6-Trimethoxystyryl-3-(4-aminobenzamido)-4-methoxybenzylsulfone. m.p. 137-140° C. NMR (DMSO-d6) δ 3.82 (s, 3H), 3.83(s, 6H), 3.86(s, 3H), 4.22(s, 2H), 6.14(s, 2H), 6.80-8.16(m, aromatic), 8.60 (s, 1H).

EXAMPLE 12

(E)-2,4,6-Trimethoxystyryl-(4-nitrophenylimino)-4-methoxybenzylsulfone

To a solution of 2,4,6-trimethoxystyryl-3-amino-4-methoxybenzylsulfone (10 mmol) in methanol (40 mL) is added 4-nitrobenzaldehyde (10 mmol). The solution is refluxed with vigorous stirring for 5 h. The reaction mixture is cooled, diluted with water and the aqueous mixture is then extracted twice with dichloromethane and organic layer is dried over anhydrous magnesium sulfate. The dried organic solution is evaporated and the residue is recrystallized to give (E)-2,4,6-trimethoxystyryl-3-(4-nitrophenylimino)-4-methoxybenzylsulfone.

EXAMPLE 12a (Alternate Procedure): (E)-2,4,6-Trimethoxystyryl-3-(4-nitrophenylimino)-4-methoxybenzylsulfone To a solution of 2,4,6trimethoxystyryl-3-amino-4-methoxybenzylsufone (10 mmol) in toluene (40 mL) is added 4-nitrobenzaldehyde (10 mmol). Toluenesulfonic acid (20 mg, 0.1 mmol) is added as an acid catalyst. The solution is stirred vigorously for 3 h at reflux. The reaction is equip ped with a Dean-Stark trap to remove water as it is formed. The mixture is then concentrated under reduced pressure and purified by recrystallization to give the desired (E)-2,4,6-trimethoxystyryl-3-(4-nitrophenylimino)-4-methoxy-benzylsulfone.

EXAMPLE 13

(E)-2,4,6-Trimethoxystyryl-3-amino-4-methoxybenzylsulfone-L-lysineamide

Step 1: (EY-2.4.6-Trimethoxystyryl-3-amino-4-methoxybenz lsulfone-L-di-Fmoc-lysineamide:

A solution of 2,4,6-trimethoxystyryl-3-amino-4-methoxybenzylsulfone (1 mmol), di-Fmoc-lysine (1.5 mmol), hydroxybenzotriazole (HOBT) (1.5 mmol) and 1,3-disopropylcarbodiimide (1.5 mmol) in dimethylformamide (DMF) (8 mL) was taken up in a reaction vessel. The reaction vessel was connected to a manual shaker and was shaken at room temperature for 5 h. Ethyl acetate (20 mL) was then added to the solution and any precipitated material was removed by filtration. The solution was dried under vacuum and the residue was treated with ethanol (20 mL) to give (E)-2,4,6-trimethoxystyryl-3-amino-4-methoxybenzylsulfone-L-di-Fmoc-lysineamide as a light yellow solid in 95% yield.

Step 2: (E)-2,4,6-Trimethoxystyryl-3-amino-methoxybenzylsulfone-L-lysineamide:

To a stirred solution of (E)-2,4,6trimethoxystyryl-3-amino-4-methoxy-benzyl-sulfone-L-di-Fmoc-lysineamide (500 mg) dichloromethane (10 mL), was added piperidine (2 mL) and stirring was continued for 2 h. The solvent was removed under vacuum and the residue was dissolved in dichloromethane and loaded on a silica-gel column. The compound was eluted with 1:1 dichloromethane and ethyl acetate. The solvent was removed in a rotary evaporator to give pure (E)-2,4,6-trimethoxystyryl-3-amino-4-methoxybenzylsulfone-L-lysineamide in 65% yield. m.p. 114-116° C.

EXAMPLE 14

(E)-2,4,6-Trimethoxystyryl-3-amino-4-methoxybenzylsulfone-L-serineamide

Step 1: (E)-2,4,6-Tnimethoxystyryl-3-amino-4-methoxybenzylsulfone-L-Fmoc-serineamide:

A solution of 2,4,6-trimethoxystyryl-3-amino-4-methoxybenzylsulfone (1 mmol), Fmoc-Ser-OH (1.5 mmol), hydroxybenzotriazole (1.5 mmol) and 1,3-diisopropylcarbodiimide (1.5 mmol) in dimethylformamide (8 mL) was taken up in a reaction vessel. The reaction vessel was connected to a manual shaker and was shaken at room temperature for 5 h. Ethyl acetate (20 mL) was then added to the solution and any precipitated material was removed by filtration. The solution was dried under vacuum and the residue was treated with ethanol (20 mL) to give (E)-2,4,6-trimethoxystyryl-3-amino-4-methoxybenzylsulfone-L-Fmoc-serineamide in 88% yield.

Step 2: (E)-2.4.6-Trimethoxystyryl-3-amino-4-methoxybenzylsulfone-L-serineamide:

To a stirred solution of (E)-2,4,6-trimethoxystyryl-3-amino-4-methoxy-benzyl-sulfone-L-Fmoc-serineamide (500 mg) in dichloromethane (10 mL), was added piperidine (2 mL) and stirring was continued for 2 h. The solvent was removed under vacuum and the residue was dissolved in dichloromethane and loaded on a silica-gel column. The compound was eluted with 1:1 dichloromethane and ethyl acetate. The solvent was removed in a rotary evaporator to give pure (E)-2,4,6-trimethoxystyryl-3-amino-4-methoxybenzylsulfone-L-serineamide in 52% yield. M,p. 132-136° C.

EXAMPLE 15

(E)-2,4,6-Trimethoxystyryl-3-amino-4-methoxybenzylsulfone-D-serineamide

Step 1: (E)-2.4.6-Trimethoxystyryl-3-amino-4-methoxybenzylsulfone-D-Fmoc-serineamide:

A solution of 2,4,6-trimethoxystyryl-3-amino-4-methoxybenzylsulfone (1 mmol), Fmoc-D-Serine (1.5 mmol), HOBT (1.5 mmol) and 1,3-diisopropylcarbodiimide (1.5 mmol) in DMF (8 mL) was taken up in a reaction vessel. The reaction vessel was connected to a manual shaker and was shaken at room temperature for 5 h. Ethyl acetate (20 mL) was then added to the solution and any precipitated material was removed by filtration. The solution was dried under vacuum and the residue was treated with ethanol (20 mL) to give (E)-2,4,6-trimethoxystyryl-3-amino-4-methoxybenzylsulfone-DrFmoc-serineamide in 90% yield.

Step 2: (E)-2,4,6-Trimethoxystyryl-3-amino-4-methoxybenzylsulfone-D-serineamide:

To a stirred solution of (E)-2,4,6-trimethoxystyryl-3-amino-4-methoxybenzylsulfone-D-Fmoc-serineamide (500 mg) in dichloromethane (10 mL), was added piperidine (2 mL), and stirring was continued for 2 h. The solvent was removed under vacuum and the residue was dissolved in dichloromethane and loaded on a silica-gel column. The compound was eluted with 1:1 dichloromethane and ethyl acetate. The solvent was removed in a rotary. evaporator to give pure (E)-2,4,6-trimethoxystyryl-3-amino-4-methoxybenzylsulfone-D-serineamide in 68% yield. m.p. 139-142° C.

EXAMPLE 16

(E)-2,4,6-Trimethoxystyryl-3-(ureido)-4-methoxybenzylsulfone

To a solution of 2,4,6-trimethoxystyryl-3-amino-4-methoxybenzylsulfone (1 mmol) in glacial acetic acid (10 mL), is added an aqueous solution of potassium cyanate (1 mmol in 2 mL of de-ionized water). The reaction mixture is stirred for 3 h at room temperature. The reaction mixture was then poured into de-ionized water (100 mL) and extracted with ethyl acetate 3 times. The combined organic layer was then washed with sodium bicarbonate to neutralize acetic acid and then with brine. The organic layer was then dried over anhydrous magnesium sulfate and the solvent was removed under vacuum to yield a precipitate which is purified by column chromatography to yield (E)-2,4,6-Teimethoxystyryl-3-(ureido)-4-methoxybenzylsulfone. m.p. 218-220° C. NMR (DMSO-d6) δ 3.80(s, 3H), 3.82(s, 6H), 3.84(s, 3H), 4.28(s, 2H), 6.18(s, 2H), 7.31-7.34(d, 1H vinylic), 7.15-8.26 (m, aromatic), 8.68(s, 1H).

EXAMPLE 17

(E)-2,4,6-Trimethoxystyryl-3-(N-methylamino)-4-methoxybenzylsulfone

To a stirred solution of sodium acetate (5 mmol) and 2,4,6-trimethoxy-3-amino-4-methoxybenzysulfone (Immol) in methanol (20 mL), was added methyl iodide (1.5 mmol) and stirring was continued at reflux temperature for 12-15 h. The contents of the flask were cooled and poured into the ice water. The white product which separated out was filtered, washed with chloroform and dried under vacuum to give (E)-2,4,6-trimethoxystyryl-3-(N-methylamino)-4-methoxybenzylsulfone in 35% yield. m.p. 133-136° C. NMR (DMSO-d6) δ 3.45(d, 3H), 3.98(s, 3H), 4.01(s, 6H), 4.15(s, 3H), 4.68(s, 2H), 6.45(s, 2H), 7.29-7.34(d, 1H vinylic), 7.64-7.95 (m, aromatic).

EXAMPLE 18

(E)-2,4,6-Trimethoxystyryl-3-(acetamido)-4-methoxybenzylsulfone

To a solution of acetyl chloride (10 mmol) in tetrahydrofuran (40 mL) was added dropwise a solution of 2,4,6-trimethoxystyryl-3-amino-4-methoxybenzylsulfone (10 mmol) in tetrahydrofuran. The solution was stirred overnight and the completion of the reaction was monitored by TLC. The solvent was removed and the residue was taken up in dichloromethane and washed with water. The organic layer was dried over anhydrous sodium sulfate and evaporated to give (E)-2,4,6-trimethoxystyryl-3-(acetamido)-4-methoxybenzylsulfone in 68% yield. M.p. 220-223° C. NMR (DMSO-d6) δ 2.02(s, 2H), 3.84(s, 3H), 3.86(s, 6H), 3.88(s, 3H), 4.22 (s, 2H), 6.08(s, 2H), 7.09-7.12(d, 1H vinylic), 6.88-7.86(m, aromatic), 8.35(s, 1H).

EXAMPLE 19

(E)-2,4,6-Trimethoxystyryl-3-(2,4-dinitrobenzene-sulfamyl)-4-methoxybenzylsulfone To a stirred solution of 2,4-dinitrobenzenesulfonyl chloride (10 mmol) and pyridine (10 mmol) in dichloromethane (30 mL) was added 2,4,6-trimethoxystyryl-3-amino-4-methoxybenzylsulfone (10 mmol) and stirring was continued at room temperature for 12-14 hours. The completion of the reaction was monitored by TLC. After the completion of the reaction, the mixture was diluted with water and organic layer separated was washed with dilute hydrochloric acid and brine. The solution was dried over anhydrous sodium sulfate. Evaporation of the organic layer under vacuum yielded (E)-2,4,6-trimethoxystyryl-3-(2,4-dinitrobenzenesulfamyl)-4-methoxybenzylsulfone in 80%. m.p. 206-208° C. NMR (DMSO-d6) δ 2.02(s, 2H), 3.81(s, 3H), 3.84(s, 9H), 4.38(s, 2H), 6.26(s, 2H), 7.05-7.08(d, 1H vinylic), 6.91-8.84 (m, aromatic), 10.27 (s, 1H).

EXAMPLE 20

(E)-2,4,6-Trimethoxystyryl-3-(2,4-diaminobenzene-sulfamyl)-4-methoxybenzylsulfone A solution of (E)-2,4,6-trimethoxystyryl-3-(2,4-dinitrobenzene-sulfamyl)-4-methoxybenzylsulfone (1.5 mmol) in acetone water (10:5) was heated to 50° C. After 30 min, sodiumhydrosulfite (Na$_2$S$_2$O$_4$) (30.3 mmol) was added slowly, and the mixture was heated to reflux (50° C., 1 h.), cooled to room temperature and water was added. The product was rinsed with NaHCO$_3$, and then isolated by extraction with ethyl acetate. The organic layer was dried over anhydrous Na$_2$SO$_4$. The solvent was removed under reduced pressure and the crude product was recrystallized from 2-propanol to yield pure (E)-2,4,6-trimethoxystyryl-3-(2,4-diaminobenzenesulfamyl)-4-methoxybenzylsulfone. m.p. 118-126° C. NMR (DMSO-d6) δ 3.72(s, 3H), 3.81(s, 6H), 3.84(s, 3H), 4.22(s, 2H), 6.27(s, 2H), 6.69-7.58(m, aromatic), 8.78(s, 1 H).

EXAMPLE 21

(E)-2,4,6-trimethoxystyryl-3-(dimethylaminoacetamido)-4-methoxybenzylsulfone

To a solution of dimethylaminoacetyl chloride (10 mmol) in tetrahydrofuran (40 mL) is added dropwise a solution of 2,4,6-trimethoxystyryl-3-amino-4-methoxybenzylsulfone (10 mmol) in tetrahydrofuran. The solution is stirred overnight and the reaction progress is monitored by TLC. The solvent is removed and the residue is taken up in dichloromethane and washed with water. The organic layer is dried over anhydrous sodium sulfate and evaporated to give the desired amide product.

EXAMPLE 22

(E)-2,4,6-trimethoxystyryl-3-[(1-carboxyethyl)amino]-4-methoxybenzylsulfone

A solution of methyl-2-bromopropionate (40 mmol) and (E)-2,4,6-trimethoxy styryl-3-amino-4-methoxybenzylsulfone (10 mmol) was reacted according to General Method B. The product obtained was purified by recrystallization from acetone. (m.p. 176-180° C.)

EXAMPLE 23

(E)-2,4,6-trimethoxystytyl-3-[4-(4-methylpiperazin-1-yl)-benzamido]-4-methoxybenzylsulfone To a solution of 4-(4-methylpiperazin-1-yl)benzoyl chloride (10 mmol) in tetrahydrofuran (40 mL) is added dropwise a solution of 2,4,6-trimethoxystyryl-3-amino-4-methoxybenzylsulfone (10 mmol) in tetrahydrofuran. The solution is stirred overnight and the reaction progress is monitored by TLC. The solvent is removed and the residue is taken up in dichloromethane and washed with water. The organic layer is dried over anhydrous sodium sulfate and evaporated to give the desired amide product.

EXAMPLE 24

(E)-2,4,6-trimethoxystyryl-3-(hydroxyacetamido)-4-methoxybenzylsulfone

A solution of (E)-2,4,6-trimethoxystyryl-3-(acetoxyacetamido)-4-methoxy benzylsulfone (10 mmol) was hydrolyzed in 50% ethanol containing potassium carbonate (70 mmol) to give (E)-2,4,6-trimethoxystyryl-3-(hydroxyacetamido)-4-methoxybenzylsulfone in 87.4% yield. (m.p. 174-1 76° C.)

EXAMPLE 25

(E)-2,4,6-trimethoxystyryl-3-(pyridinium-1-yl)acetamido-4-methoxybenzylsulfone

A solution of pyridine (100 mmol) and (E)-2,4,6-trimethoxystyryl-3-chloroacetamido-4-methoxy benzylsulfone (1 mmol) was heated to reflux. A solid precipitate formed and was separated by filtration. The recovered material was purified by recrystallization to yield 68.5% of the desired product. (m.p. 132-134° C.)

EXAMPLE 26

(E)-2,4,6-trimethoxystyryl-3-(acetoxyacetamido)-4-methoxybenzylsulfone

A solution of acetoxyacetyl chloride (10 mmol) and (E)-2,4,6-trimethoxystyryl-3-amino-4-methoxy benzylsulfone (10 mmol) was reacted according to General Method A. The product obtained was purified column chromatography to give a 90% yield of the desired product. (m.p. 192-1 94° C.)

EXAMPLE 27

(E)-2,4,6-Trimethoxcystyryl-3-(2-hydroxypropionamido)-4-methoxy benzylsulfone

A solution of (E)-2,4,6-trimethoxystyryl-3-(2-acetoxypropionamido)-4-methoxybenzylsulfone (10 mmol) was hydrolyzed with potassium carbonate (70 mmol) in 1:1 ethanol/water (25 mL) to give (E)-2,4,6-trimethoxystyryl-3-(2-hydroxy-2-methylacetamido)-4-methoxy benzylsulfone. (m.p. 174-1 76° C.)

EXAMPLE 28

(E)-2,4,6-trimethoxystyryl-3-triethylammoniumacetamido)-4-methoxybenzylsulfone

A solution of triethylamine (100 mmol) and (E)-2,4,6-trimethoxystyryl-3-(chloroacetamido)-4-methoxybenzylsulfone (1 mmol) was heated to reflux. A solid precipitate formed and was separated by filtration. The solid was purified by recrystallization to yield 52.5% of the desired product. (m.p. 172-174° C.)

EXAMPLE 29

(E)-2,4,6-trimethoxystyryl-3-[tri-(2-hydroxyethyl)ammonium]-acetamido-4-methoxybenzylsulfone A solution of triethanolamine (100 mmol) and (E)-2,4,6-trimethoxystyryl-3-(chloroacetamido)-4-methoxybenzylsulfone (1 mmol) was heated to reflux. A solid precipitate formed and was separated by filtration. The solid was purified by recrystallization to yield the desired product.

EXAMPLE 30

(E)-2,4,6-trimethoxystyryl-3-(2-methyl-2-hydroxypropionamido)-4-methoxybenzylsulfone A solution of (E)-2,4,6-trimethoxystyryl-3-(2-methyl-2-hydroxypropionamido))-4-methoxy benzylsulfone (10 mmol) was hydrolyzed in one-to-one water/ethanol containing potassium carbonate (70 mmol). The desired product was isolated in 95.2% yield. (m.p. 198-199° C.)

EXAMPLE 31

(E)-2,4,6-trimethoxystyryl-3-(2-methyl-2-acetoxypropionamido)-4-methoxybenzylsulfone A solution of 1-chlorocarbonyl-1-methylethyl acetate (10 mmol) and (E)-2,4,6-trimethoxystyryl-3-amino-4-methoxybenzylsulfone (10 mmol) was reacted according to General Method A. The crude product obtained was purified by column chromatography to yield the desired product in 98% yield. (m.p. 148-150° C.)

EXAMPLE 32

(E)-2,4,6-trimethoxystyryl-3-(trifluoroacetamido)-4-methoxybenzylsulfone

A solution of trifluoroacetic anhydride (20 mmol) and (E)-2,4,6-trimethoxystyryl-3-amino-4-methoxy benzylsulfone (10 mmol) in dry dichloromethane (25 mL) was stirred for 2 hours at room temperature and excess of trifluoroacetic anhydride was removed under vacuum and the product obtained was purified by washing with diethyl ether, yield 98%, m.p. 179-180° C.

EXAMPLE 33

(E)-2,4,6-trimethoxystyryl-3-(trifluoromethanesulfonamido)-4-methoxybenzylsulfone A solution of trifluoromethanesulfonyl chloride (10 mmol) and (E)-2,4,6-trimethoxystyryl-3-amino-4-methoxybenzylsulfone (10 mmol) was reacted according to General Method A. The product obtained was purified by column chromatography to give the desired product in 59.9% yield. (m.p. 144-46° C.)

EXAMPLE 34

(E)-2,4,6-trimethoxystyryl-3-(succinamido)-4-methoxybenzylsulfone

A solution of succinic anhydride (20 mmol) and (E)-2,4,6-trimethoxystyryl-3-amino-4-methoxybenzylsulfone (10 mmol) in dry dichloromethane (25 mL) was stirred for 2 hours at room temperature. The reaction was monitored by TLC. When the reaction was complete, the excess succinic anhydride was removed under vacuum and the residue obtained was purified by washing with diethyl ether to yield the desired product in 98% yield. (m.p. 196-198° C.)

EXAMPLE 35

(E)-2,4,6-trimethoxystyryl-3-(3-chlorosuccinamido)-4-methoxybenzylsulfone

A solution of succinyl chloride (15 mmol) and (E)2,4,6-trimethoxystyryl-3-amino-4-methoxybenzylsulfone (10 mmol) was reacted according to General Method A. The product obtained was purified by recrystallization.

EXAMPLE 36

(E)-2,4,6-trimethoxystyryl-3-[3-(3-carboxypropanoyloxy)-acetamido]-4-methoxybenzylsulfone A solution of succinic anhydride (20 mmol) and (E)-2,4,6-trimethoxystyryl-3-(hydroxyacetamido)-4-methoxybenzylsulfone (10 mmol) in dry dichloromethane (25 mL) is stirred for 2 hours at room temperature. The reaction is monitored by TLC. When the reaction is complete, the excess succinic anhydride is removed under vacuum and the remaining residue is purified by triturafion with diethyl ether.

EXAMPLE 37

(E)-2,4,6-trimethoxystyryl-3-(glutaramido)-4-methoxybenzylsulfone

A solution of glutaric anhydride (20 mmol) and (E)2,4,6-trimethoxystyryl-3-amino-4-methoxybenzylsulfone (10 mmol) in dry dichloromethane (25 mL) is stirred for 2 hours at room temperature. The reaction is monitored by TLC. When the reaction is complete, the excess glutaric anhydride is removed under vacuum and the residue obtained is purified by trituration with diethyl ether to yield the desired product.

EXAMPLE 38

(E)-2,4,6-trimethoxystyryl-3-(phosphonatoacetamido)-4-methoxybenzylsulfone, disodium salt A solution of (E)-2,4,6-trimethoxystyryl-3-(hydroxyacetamido)-4-methoxy benzylsulfone was treated with 2,2,2-(trichloroethyl)phosphate in the presence of 4-dimethylaminopyridine (DMAP) and triethylamine. The intermediate trichloroethyl (Troc) protected ester was deprotected by treating with Zn/Cu in presence of pentadione. The free acid thus liberated was treated with sodium methoxide in methanol to produce the desired product in 46% yield. (m.p. >325° C.)

EXAMPLE 39

(E)-2,4,6-trimethoxystyryl-3-(3-carboxypropylamino)-4-methoxybenzylsulfone

A solution of methyl-4-bromobutyrate (40 mmol) and (E)-2,4,6-trimethoxystyryl-3-amino-4-methoxybenzylsulfone (10 mmol) was reacted according to General Method B. The product obtained was purified by recrystallization from acetone. (m.p. 86-88° C.)

EXAMPLE 40

(E)-2,4,6-trimethoxystyryl-3-(2-carboxyethylamino)-4-methoxybenzylsulfone

A solution of methyl-3-bromopropionate(40 mmol) and (E)-2,4,6-trimethoxystyryl-3-amino-4-methoxybenzylsulfone (10 mmol) was reacted according to General Method B. The product obtained was purified by recrystallization from acetone. (m.p. 156-158° C.)

EXAMPLE 41

(E)-2,4,6-trimethoxystyryl-3-(methoxycarbonylamino)-4-methoxybenzylsulfone

A solution of methylchloroformate (10 mmol) and (E)-2,4,6-trimethoxystyryl-3-amino-4-methoxyberzylsulfone (10 mmol) was reacted according to General Method A. The product obtained was purified by recrystallization from 2-propanol. (yield 51%, m.p. 188-191° C.)

EXAMPLE 42

(E)-2,4,6-trimethoxystyryl-3-(4-methoxybenzenesulfamyl)-4-methoxybenzylsulfone

A solution of 4-methoxybenzenesulfonyl chloride (10 mmol) and (E)-2,4,6-trimethoxystyryl-3-amino-4-methoxybenzylsulfone (10 mmol) was reacted according to General Method A. The product obtained was purified by recrystallization from 2-propanol. (yield 66.6%, m.p. 181-183° C.)

EXAMPLE 43

(E)-2,4,6-trimethoxystyryl-3(2-acetoxypropionamido)-4-methoxybenzylsulfone

A solution of 2-acetoxypropionyl chloride (10 mmol) and (E)-2,4,6-trimethoxystyryl-3-amino-4-methoxybenzylsulfone (10 mmol) was reacted according to General Method A. The product obtained was purified by column chromatography to give the desired product in 68.2% yield. (m.p. 179-180° C.)

EXAMPLE 44

(E)-2,4,6-trimethoxystyryl-3-(methylsuccinamido)-4-methoxybenzylsulfone

A solution of methyl-4-chloro-4-oxobutyrate (10 mmol) and (E)-2,4,6-trimethoxystyryl-3-aminomethoxybenzylsulfone (10 mmol) was reacted according to General Method A. The product obtained was purified by column chromatography to give the desired product in 74.4% yield. (m.p. 180-182° C.)

EXAMPLE 45

(E)-2,4,6-trimethoxystyryl-3-(ethylmalonamido)-4-methoxybenzylsulfone

A solution of ethylmalonylchloride (10 mmol) and (E)-2,4,6-trimethoxystyryl-3-amino-4-methoxybenzylsulfone (10 mmol) was reacted according to General Method A. The product obtained was purified by column chromatography to give the desired product.

EXAMPLE 46

(E)-2,4,6-trimethoxystyryl-3-(pentafluoropropiona-mido)-4-methoxybenzylsulfone

A solution of pentafluoropropionic anhydride (20 mmol) and (E)-2,4,6-trimethoxystyryl-3-amino-4-methoxybenzylsulfone (10 mmol) were stirred in dry dichloromethane (25 mL) was stirred for 2 hours at room temperature. The reaction was monitored by TLC. When the reaction was complete, the excess pentafluoropropionic anhydride was removed under vacuum. The resulting residue was purified by washing with diethyl ether to give the desired product in 98.9% yield. (m.p. 179-180° C.)

EXAMPLE 47

(E)-2,4,6-trimethoxystyryl-3-(methyl-2,2-difluoro-malonamido)-4-methoxybenzylsulfone A solution of methyl chlorodifluoroacetate (40 mmol) and (E)-2,4,6-trimethoxy styryl-3-amino-4-methoxybenzylsulfone (10 mmol) was reacted according to General Method B. The product obtained was purified by column chromatography to give the desired product in 52% yield. (m.p. 166-168° C.)

EXAMPLE 48

(E)-2,4,6-Trimethoxystyryl-3-(2,2,3,3,tetrafluorosuc-cinamido)-4-methoxybenzylsulfone A solution of tetrafluorosuccinic anhydride (20 mmol) and (E)-2,4,6-trimethoxystyryl-3-amino-4-methoxybenzylsulfone (10 mmol) in dry dichloromethane (25 mL) was stirred for 2 hours at room temperature. The reaction was monitored by TLC. When the reaction was complete, the excess tetrafluorosuccinic anhydride was removed under vacuum and the residue obtained was purified by washing with diethyl ether to give the desired product in 96.3% yield. (m.p. 156-158° C.)

EXAMPLE 49

(E)-2,4,6-Trimethoxy-styryl-3-aminoacetamido)-4-methoxybenzylsulfone, hydrochloride To a solution of (E)-2,4,6-trimethoxystyryl-3-amino-4-methoxybenzylsulfone (10 mmol) and t-Boc glycine in dichloromethane (25 mL) was added dicyclohexylcarbodiimide (DCC) (11 mmol) and 4-dimethylaminopyridine (DMAP) (catalytic amount). The resulting mixture was stirred at room temperature for 24 hours. The intermediate t-Boc protected compound was purified by column chromatography on a silica column. The t-Boc protecting group was subsequently removed by stirring the intermediate compound at room temperature in in a solution of 4M hydrochloric acid/dichloromethane. The precipitated salt was collected by filtration and purified by triturafion with diethyl ether. (yield 96%, m.p. >280° C.).

EXAMPLE 50

(E)-2,4,6-trimethoxystyryl-3-(2,2-difluoromalona-mido)-4-methoxybenzylsulfone

A solution of (E)-2,4,6-trimethoxystyryl-3-(methyl-2,2-difluoromalonamido)-4-methoxybenzylsulfone (10 mmol) is hydrolyzed with potassium carbonate (70 mmol) in 1:1 ethanol/water (25 mL) to give the corresponding carboxylic acid.

EXAMPLE 51

(E)-2,4,6-trimethoxystyryl-3-(dimethylamino-α,α-difluoroacetamido)-4-methoxybenzylsulfone To a solution of dimethylamino-α,α-difluoroacetyl chloride (10 mmol) in tetrahydrofuran (40 mL) is added dropwise a solution of 2,4,6-trimethoxystyryl-3-amino-4-methoxybenzyisulfone (10 mmol) in tetrahydrofuran. The solution is stirred overnight and the reaction progress is monitored by TLC. The solvent is removed and the residue is taken up in dichloromethane and washed with water. The organic layer is dried over anhydrous sodium sulfate and evaporated to give the desired amide product.

The example compounds, along with their structural formulae are listed in Table 1 below.

TABLE 1

| Compound | Structure | Name |
|---|---|---|
| 1 | 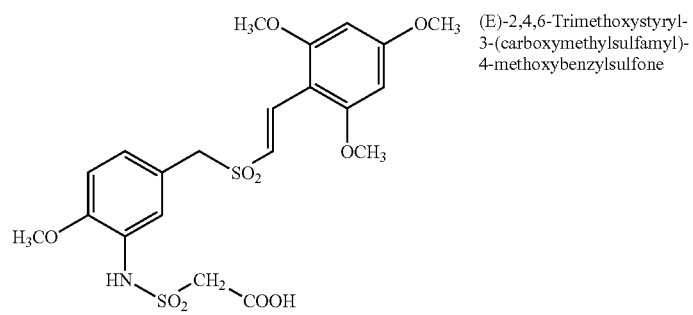 | (E)-2,4,6-Trimethoxystyryl-3-(carboxymethylsulfamyl)-4-methoxybenzylsulfone |

TABLE 1-continued

| Compound | Structure | Name |
|---|---|---|
| 2 | 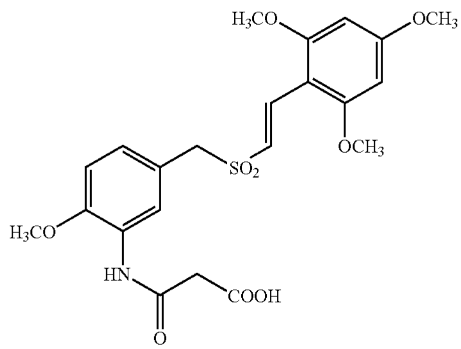 | (E)-2,4,6-Trimethoxystyryl-3-(carboxyacetamido)-4-methoxybenzylsulfone |
| 3 | 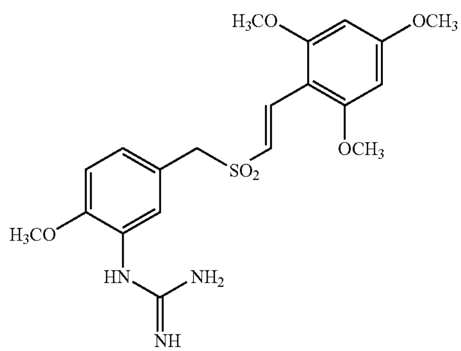 | (E)-2,4,6-Trimethoxystyryl-3-(guanidino)-4-methoxy-benzylsulfone |
| 4 | 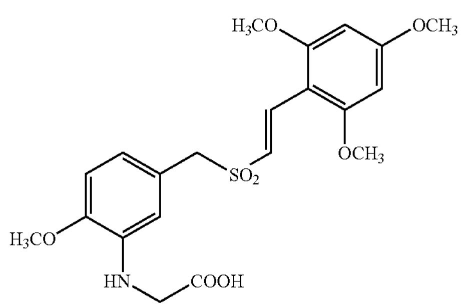 | (E)-2,4,6-Trimethoxystyryl-3-(carboxymethylamino)-4-methoxybenzylsulfone |
| 5 | 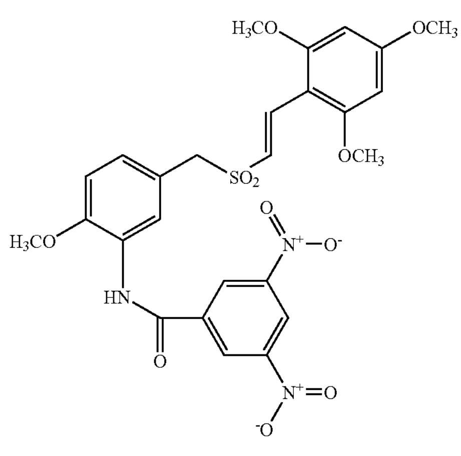 | (E)-2,4,6-trimethoxystyryl-3-(3,5-dinitrobenzamido)-4-methoxybenzylsulfone |

TABLE 1-continued

| Compound | Structure | Name |
| --- | --- | --- |
| 6 | 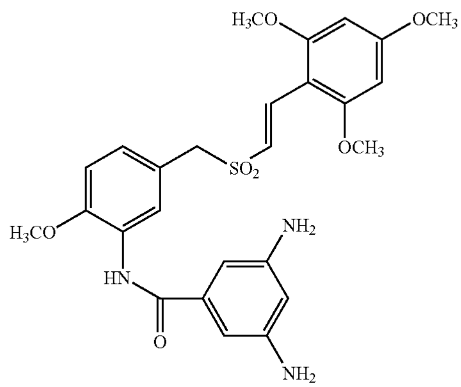 | (E)-2,4,6-trimethoxystyryl-3-(3,5,diamino-benzamido)-4-methoxybenzylsulfone |
| 7 | 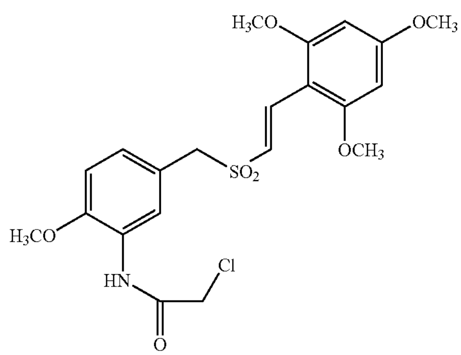 | (E)-2,4,6-Trimethoxystyryl-3-(chloroacetamido)-4-methoxybenzylsulfone |
| 8 | 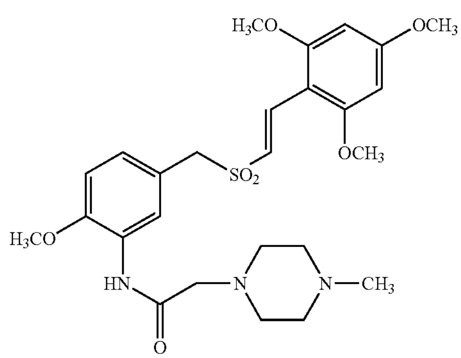 | (E)-2,4,6-Trimethoxystyryl-3[(4-methylpiperazinyl)-acetamido]-4-methoxy-benzylsulfone |
| 9 | 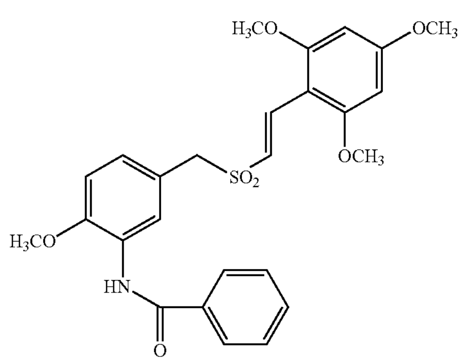 | (E)-2,4,6-Trimethoxystyryl-3-benzamido-4-methoxy-benzylsulfone |

TABLE 1-continued

| Compound | Structure | Name |
|---|---|---|
| 10 | 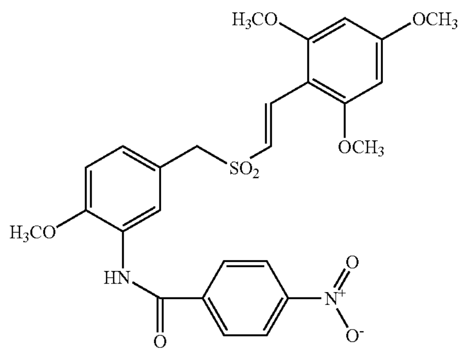 | (E)-2,4,6-Trimethoxystyryl-3-(4-nitrobenzamido)-4-methoxybenzylsulfone |
| 11 | 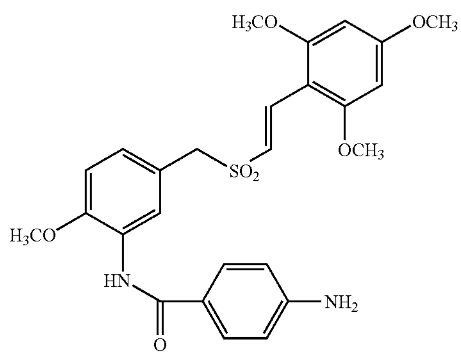 | (E)-2,4,6-Trimethoxystyryl-3-(4-aminobenzamido)-4-methoxybenzylsulfone |
| 12 | 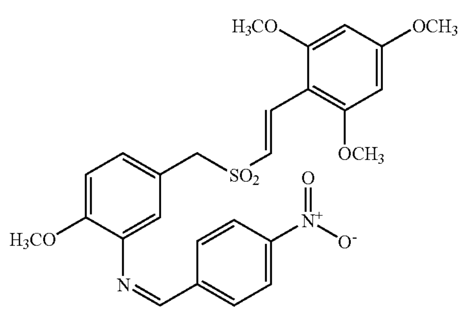 | (E)-2,4,6-Trimethoxystyryl-3-(4-nitrophenylimino)-4-methoxybenzylsulfone |
| 13 | 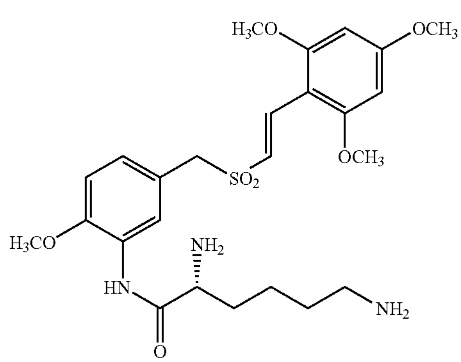 | (E)-2,4,6-Trimethoxystyryl-3-amino-4-methoxybenzyl-sulfone-L-lysineamide |

TABLE 1-continued

| Compound | Structure | Name |
|---|---|---|
| 14 | 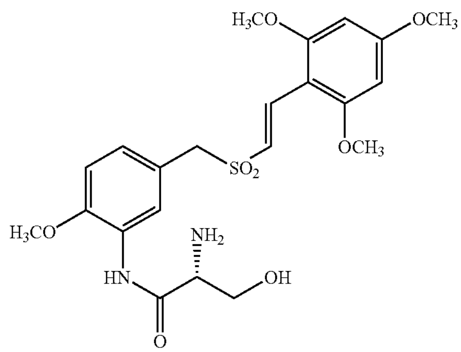 | (E)-2,4,6-Trimethoxystyryl-3-amino-4-methoxybenzyl-sulfone-L-serineamide |
| 15 | 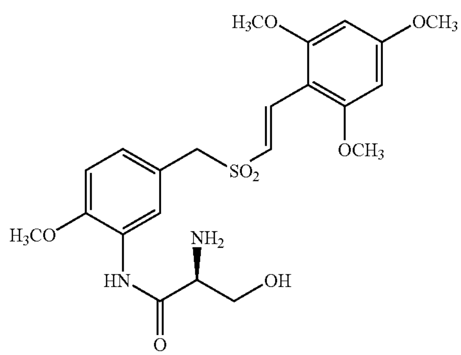 | (E)-2,4,6-Trimethoxystyryl-3-amino-4-methoxybenzyl-sulfone-D-serineamide |
| 16 | 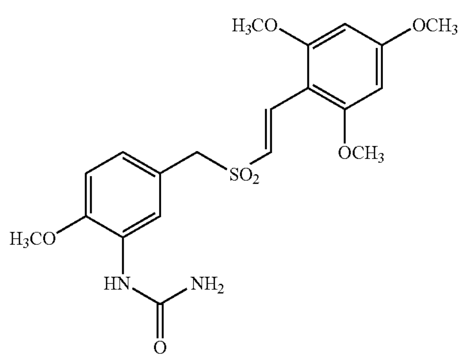 | (E)-2,4,6-Trimethoxystyryl-3-ureido-4-methoxybenzyl-sulfone |
| 17 | 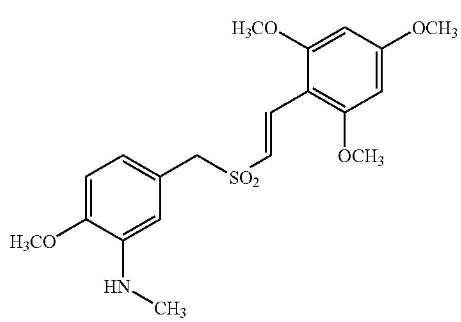 | (E)-2,4,6-Trimethoxystyryl-3-(N-methylamino)-4-methoxybenzylsulfone |

TABLE 1-continued

| Compound | Structure | Name |
|---|---|---|
| 18 | 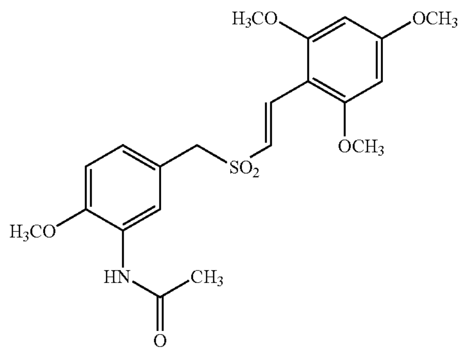 | (E)-2,4,6-Trimethoxystyryl-3-(acetamido)-4-methoxybenzylsulfone |
| 19 | 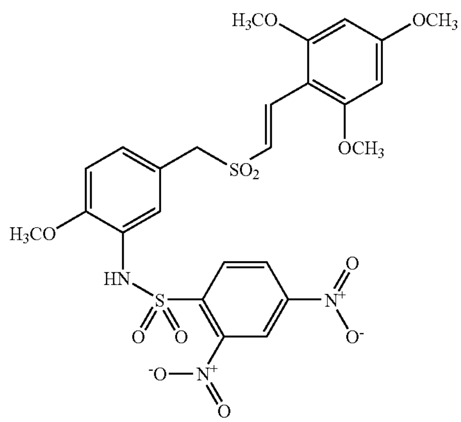 | (E)-2,4,6-Trimethoxystyryl-3-(2,4,-dinitrobenzenesulfamyl)-4-methoxybenzylsulfone |
| 20 | 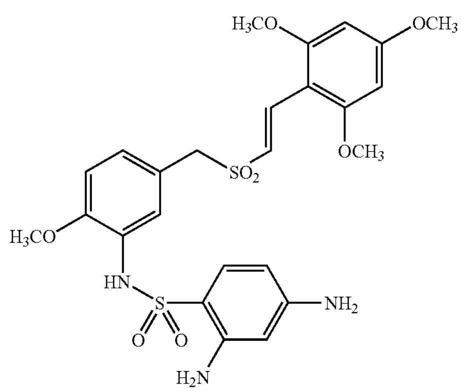 | (E)-2,4,6-Trimethoxystyryl-3-(2,4-diaminobenzenesulfamyl)-4-methoxybenzylsulfone |
| 21 | 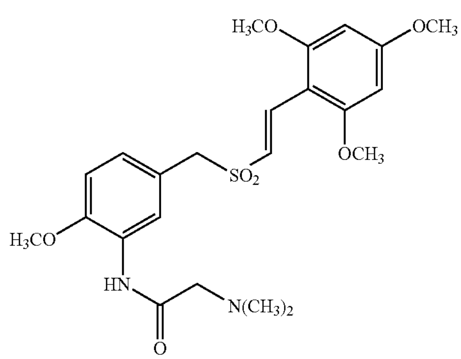 | (E)-2,4,6-trimethoxystyryl-3-(dimethylaminoacetamido)-4-methoxybenzylsulfone |

TABLE 1-continued

| Compound | Structure | Name |
|---|---|---|
| 22 | 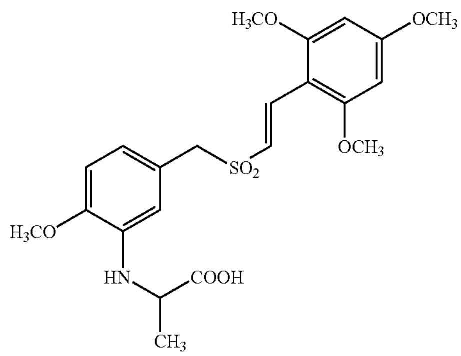 | (E)-2,4,6-trimethoxystyryl-3-(1-carboxyethyl)amino-4-methoxybenzylsulfone |
| 23 | 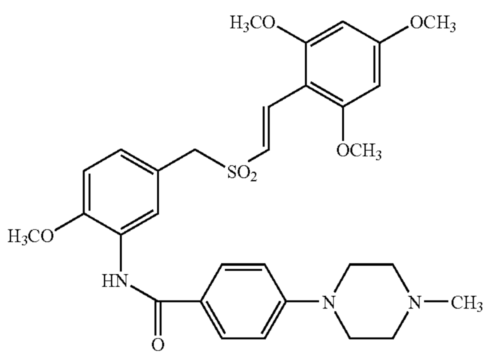 | (E)-2,4,6-trimethoxystyryl-3-[4-(4-methylpiperazin-1-yl)-benzamido]-4-methoxy-benzylsulfone |
| 24 | 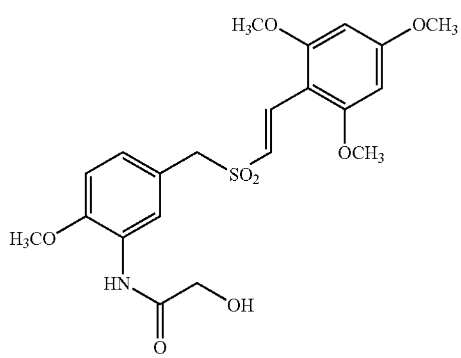 | (E)-2,4,6-trimethoxystyryl-3-(hydroxyacetamido)-4-methoxybenzylsulfone |
| 25 | 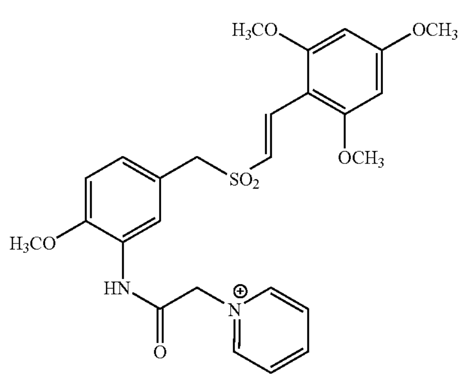 | (E)-2,4,6-trimethoxystyryl-3-[(pyridinium-1-yl)-acetamido]-4-methoxy-benzylsulfone |

TABLE 1-continued

| Compound | Structure | Name |
|---|---|---|
| 26 | 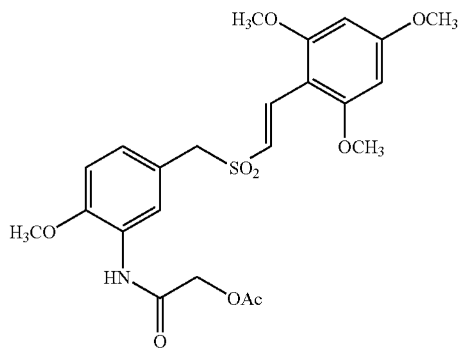 | (E)-2,4,6-trimethoxystyryl-3-(acetoxyacetamido)-4-methoxybenzylsulfone |
| 27 | 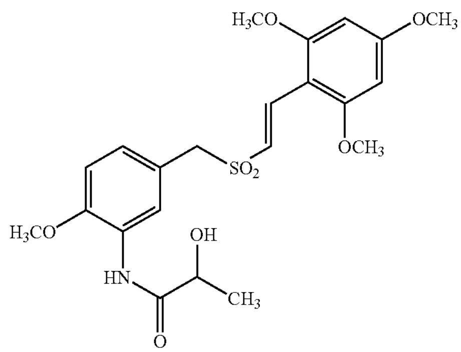 | (E)-2,4,6-Trimethoxystyryl-3-(2-hydroxypropionamido)-4-methoxybenzylsulfone |
| 28 | 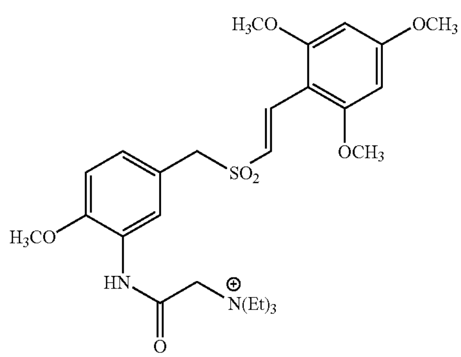 | (E)-2,4,6-trimethoxystyryl-3-(triethylammonium-acetamido)-4-methoxy-benzylsulfone |
| 29 | 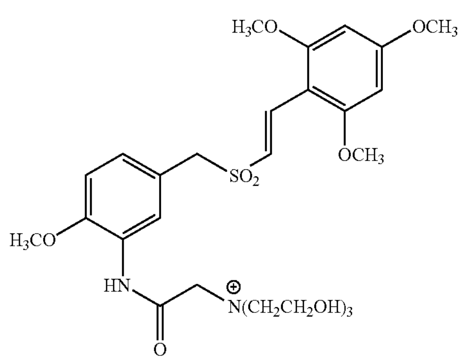 | (E)-2,4,6-trimethoxystyryl-3-[tri-(2-hydroxyethyl)-ammoniumacetamido]-4-methoxybenzylsulfone |

TABLE 1-continued

| Compound | Structure | Name |
|---|---|---|
| 30 | 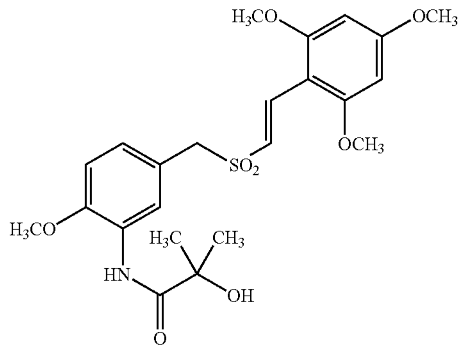 | (E)-2,4,6-trimethoxystyryl-3-(2-methyl-2-hydroxy-propionamido)-4-methoxy-benzylsulfone |
| 31 | 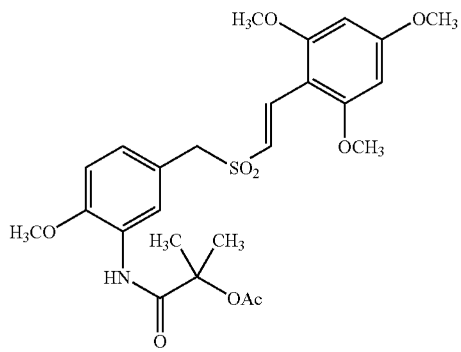 | (E)-2,4,6-trimethoxystyryl-3-(2-methyl-2-acetoxypropion-amido)-4-methoxybenzyl-sulfone |
| 32 | 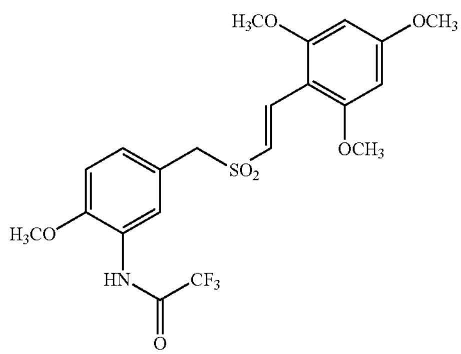 | (E)-2,4,6-trimethoxystyryl-3-(trifluoroacetamido)-4-methoxybenzylsulfone |
| 33 | 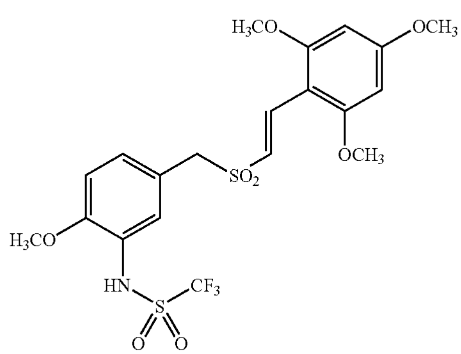 | (E)-2,4,6-trimethoxystyryl-3-(trifluoromethanesulfon-amido)-4-methoxybenzyl-sulfone |

TABLE 1-continued

| Compound | Structure | Name |
|---|---|---|
| 34 | 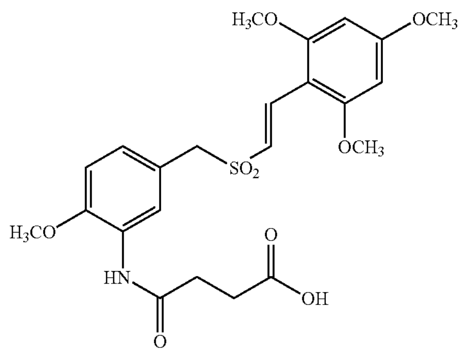 | (E)-2,4,6-trimethoxystyryl-3-(succinamido)-4-methoxy-benzylsulfone |
| 35 | 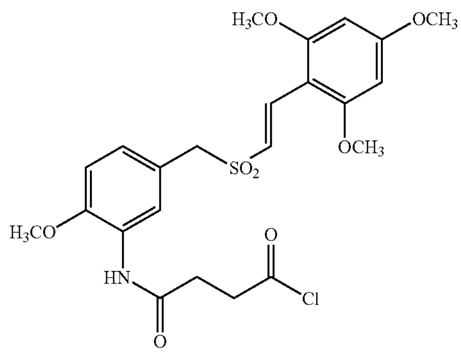 | (E)-2,4,6-trimethoxystyryl-3-(chlorosuccinamido)-4-methoxybenzylsulfone |
| 36 | 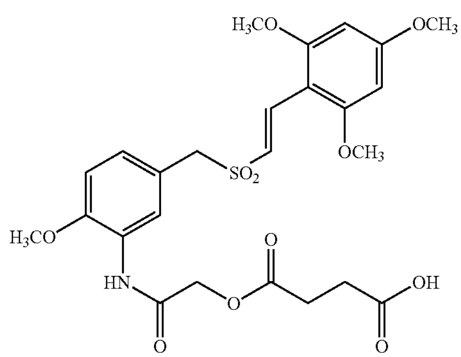 | (E)-2,4,6-trimethoxystyryl-3-(3-((3-carboxypropanoyl-oxy)acetamido)-4-methoxy-benzylsulfone |
| 37 | 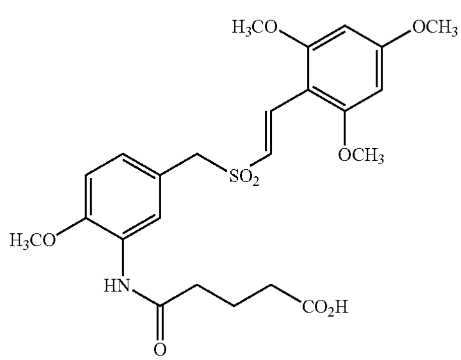 | (E)-2,4,6-trimethoxystyryl-3-(3-glutaramido)-4-methoxybenzylsulfone |

TABLE 1-continued

| Compound | Structure | Name |
|---|---|---|
| 38 | 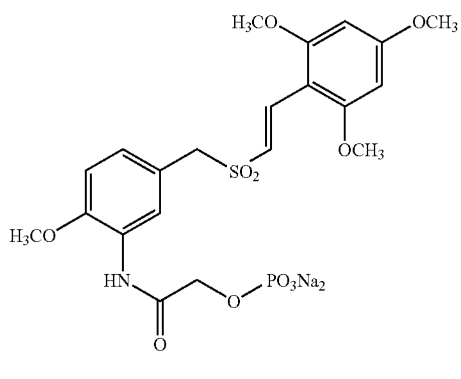 | (E)-2,4,6-trimethoxystyryl-3-(phosphonatoacetamido)-4-methoxybenzylsulfone, disodium salt |
| 39 | 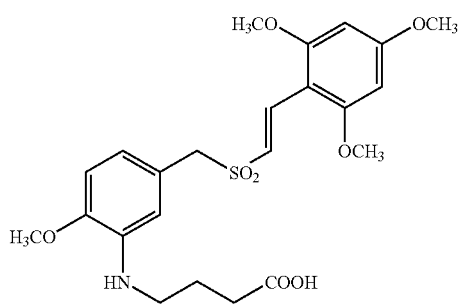 | (E)-2,4,6-trimethoxystyryl-3-(3-carboxypropylamino)-4-methoxybenzylsulfone: |
| 40 | 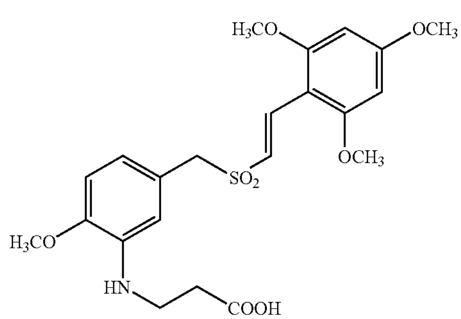 | (E)-2,4,6-trimethoxystyryl-3-(2-carboxyethylamino)-4-methoxybenzylsulfone |
| 41 | 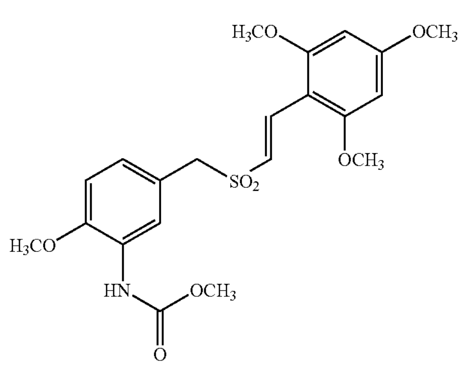 | (E)-2,4,6-trimethoxystyryl-3-(methoxycarbonylamino)-4-methoxybenzylsulfone |

TABLE 1-continued

| Compound | Structure | Name |
|---|---|---|
| 42 | 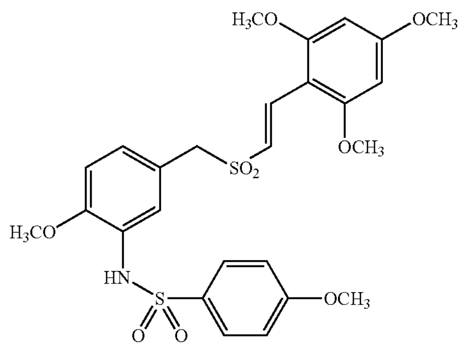 | (E)-2,4,6-Trimethoxystyryl-3-(4-methoxybenzene-sulfamyl)-4-methoxybenzyl-sulfone |
| 43 | 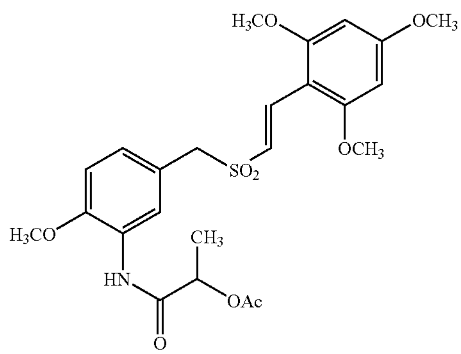 | (E)-2,4,6-trimethoxystyryl-3-(2-acetoxypropionamido)-4-methoxybenzylsulfone |
| 44 | 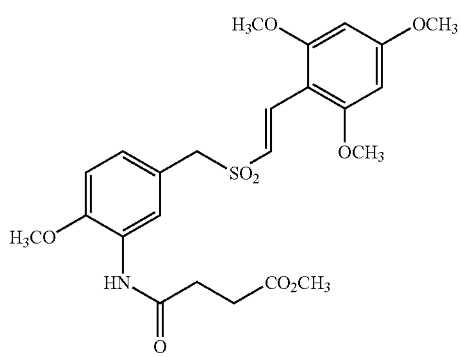 | (E)-2,4,6-trimethoxystyryl-3-(methylsuccinamido)-4-methoxybenzylsulfone |
| 45 | 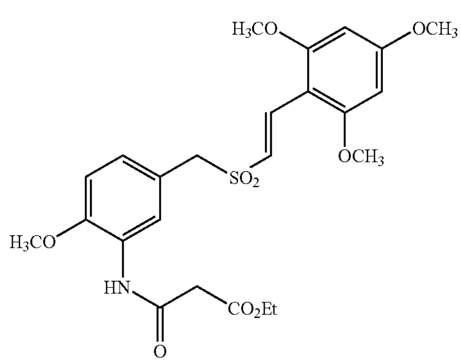 | (E)-2,4,6-trimethoxystyryl-3-(ethylmalonamido)-4-methoxybenzylsulfone |

TABLE 1-continued

| Compound | Structure | Name |
|---|---|---|
| 46 | 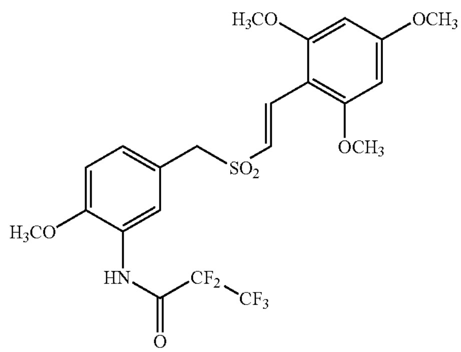 | (E)-2,4,6-Trimethoxystyryl-3-(pentafluoropropionamido)-4-methoxybenzylsulfone |
| 47 | 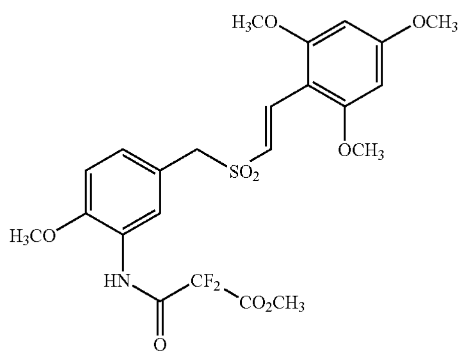 | (E)-2,4,6-trimethoxystyryl-3-(methyl-2,2-difluoro-malonamido)-4-methoxy-benzylsulfone |
| 48 | 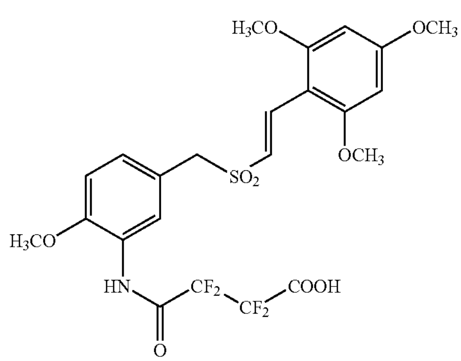 | (E)-2,4,6-Trimethoxystyryl-3-(2,2,3,3,tetrafluoro-succinamido)-4-methoxy-benzylsulfone |

TABLE 1-continued

| Compound | Structure | Name |
|---|---|---|
| 49 | 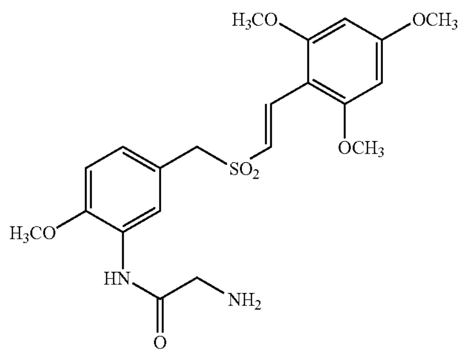 | (E)-2,4,6-Trimethoxystyryl-3-(aminoacetamido)-4-methoxybenzylsulfone |
| 50 | 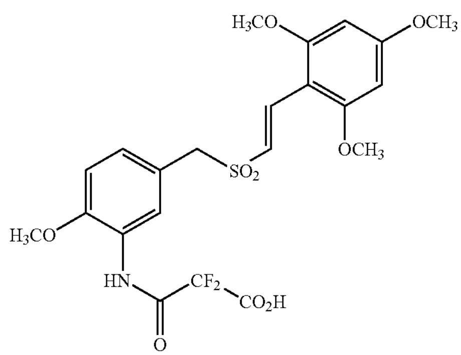 | (E)-2,4,6-trimethoxystyryl-3-(2,2-difluoro-malonamido)-4-methoxy-benzylsulfone |
| 51 | 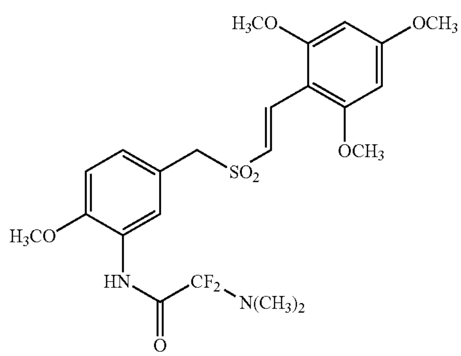 | (E)-2,4,6-trimethoxystyryl-3-(dimethylamino-α,α-difluoroacetamido)-4-methoxybenzylsulfone |

EXAMPLE 51

The Effect of Compounds on Tumor Cell Lines

A. Cells.

The effect is determined of certain compounds of the invention on the growth of normal fibroblasts (NIH/3T3 and HFL) and on cells of the following cell lines: prostate carcinoma cell line DU-145; colorectal carcinoma cell line DLD-1; non-small cell lung carcinoma cell line H157; and breast adenocarcinoma cell line BT-20. BT-20 is an estrogen-unresponsive cell line. NIH/3T3 and HFL are normal murine and human fibroblasts, respectively. BT-20, DLD-1 and H157 were grown in Dulbecco's modified Eagle's medium (DMEM) containing 10% fetal bovine serum supplemented with penicillin and streptomycin. DU145 was cultured in RPMI with 10% fetal bovine serum containing penicillin and streptomycin. NIH3T3 and HFL cells were grown in DMEM containing 10% calf serum supplemented with penicillin and streptomycin. Cells were plated at density levels of $1.0 \times 10^5$ cells per well in six-well plates. Cell cultures were maintained at 37° C. in a humidified atmosphere of 5% $CO_2$.

Biological data generated in the above described assays is listed in Table 2, below. A (+) in the Table indicates that the compound demonstrated an $IC_{50}$ of less than 10 micromolar.

B. Treatment with Styryl Benzylsulfone and Viability Assay

Cells were treated with compounds of the invention at various concentrations. Cell viability was determined after 96 hours by the Trypan blue exclusion method. Each compound tested displayed an IC50 of or below 20 μM under the conditions of the assay. See Table 2. Normal cells HFL and NIH 3T3 treated with the same compound displayed 5% growth inhibition but no appreciable cell death.

TABLE 2

Examples and Biological Activity.

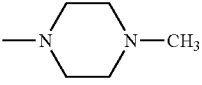

| Ex. | M | R¹ | R² | DU-145 | BT-20 | DLD-1 | H157 |
|---|---|---|---|---|---|---|---|
| 1 | —SO$_2$CH$_2$— | —C(=O)OH | —H | + | + | + | + |
| 2 | —C(=O)CH$_2$— | —C(=O)OH | —H | + | + | + | + |
| 3 | — | —C(=NH)NH$_2$ | —H | + | + | + | + |
| 4 | —CH$_2$— | —C(=O)OH | —H | + | + | + | + |
| 5 | —C(=O)NH— | -3,5(NO$_2$)$_2$C$_6$H$_3$ | —H | + | + | + | + |
| 6 | —C(=O)NH— | 3,5(NH$_2$)$_2$C$_6$H$_3$ | —H | + | + | + | + |
| 7 | —C(=O)— | —CH$_2$Cl | —H | + | + | + | + |
| 8 | —C(=O)CH$_2$— | 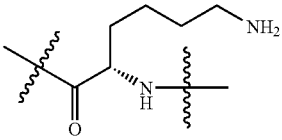 | —H | + | + | + | + |
| 9 | —C(=O)— | —C$_6$H$_5$ | —H | + | + | + | + |
| 10 | —C(=O)— | 4-NO$_2$—C$_6$H$_5$ | —H | + | + | + | + |
| 12 | =CH—C$_6$H$_4$—NO$_2$ | | —H | ND | ND | ND | ND |
| 13 | 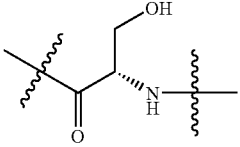 | —H | —H | + | + | + | + |
| 14 | 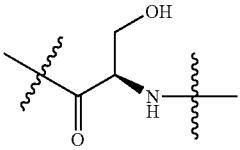 | —H | —H | + | + | + | + |
| 15 | 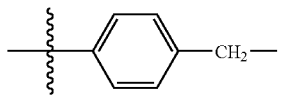 | —H | —H | + | + | + | + |
| 16 | —C(=O)NH— | —H | —H | + | + | + | + |
| 17 | —CH$_2$— | —H | —H | + | + | + | + |
| 18 | —C(=O)— | CH$_3$ | —H | + | + | + | + |
| 19 | —SO$_2$— | 3,5(NO$_2$)$_2$C$_6$H$_3$— | —H | + | + | + | + |
| 20 | —SO$_2$— | 3,5(NH$_2$)$_2$C$_6$H$_3$— | —H | + | + | + | + |
| 21 | —C(=O)— | (CH$_3$)$_2$NCH$_2$— | —H | + | + | + | + |
| 22 | — | HO$_2$CCH(CH$_3$)— | —H | + | + | + | + |
| 23 | 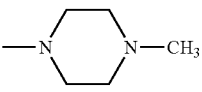 | 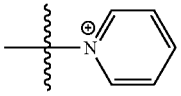 | —H | + | + | + | + |
| 24 | —C(=O)— | —CH$_2$OH | —H | + | + | + | + |
| 25 | —C(=O)CH$_2$— |  | —H | + | + | + | + |

TABLE 2-continued

Examples and Biological Activity.

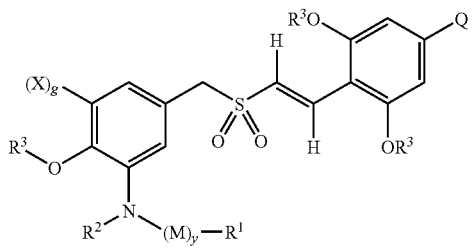

| Ex. | M | R$^1$ | R$^2$ | DU-145 | BT-20 | DLD-1 | H157 |
|---|---|---|---|---|---|---|---|
| 26 | —C(=O)CH$_2$— | —OC(=O)CH$_3$ | —H | + | + | + | + |
| 27 | —C(=O)— | —CH(CH$_3$)OH | —H | + | + | + | + |
| 28 | —C(=O)CH$_2$— | —N(C$_2$H$_5$)$_3$$^+$ | —H | + | + | + | + |
| 29 | —C(=O)CH$_2$— | —N(C$_2$H$_4$OH)$_3$$^+$ | —H | + | + | + | + |
| 30 | —C(=O)— | —(CH$_3$)$_2$OH | —H | + | + | + | + |
| 31 | —C(=O)— | —C(CH$_3$)$_2$OAc | —H | + | + | + | + |
| 32 | —C(=O)— | —CF$_3$ | —H | + | + | + | + |
| 33 | —SO$_2$— | —CF$_3$ | —H | + | + | + | + |
| 34 | —C(=O)(CH$_2$)$_2$— | —C(=O)OH | —H | + | + | + | + |
| 35 | —C(=O)(CH$_2$)$_2$— | —C(=O)Cl | —H | + | + | + | + |
| 36 | —C(=O)CH$_2$— | O-succinate | —H | + | + | + | + |
| 37 | —C(=O)(CH$_2$)$_3$— | COOH | —H | + | + | + | + |
| 38 | —C(=O)CH$_2$— | —OPO$_3$Na$_2$ | —H | + | + | + | + |
| 39 | —(CH$_2$)$_3$— | —COOH | —H | + | + | + | + |
| 40 | —(CH$_2$)$_2$— | —COOH | —H | + | + | + | + |
| 41 | —C(=O)— | —OCH$_3$ | —H | + | + | + | + |
| 42 | —SO$_2$— | 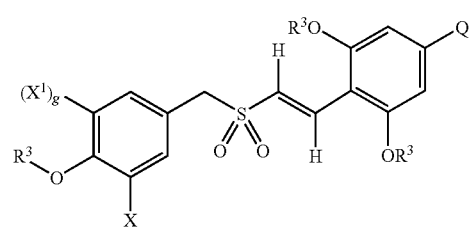 | —H | + | + | + | + |
| 43 | —C(=O)— | —C(CH$_3$)$_2$CO$_2$CH$_3$ | —H | + | + | + | + |
| 44 | —(CH$_2$)$_2$— | —COOCH$_3$ | —H | + | + | + | + |
| 45 | —C(=O)CH$_2$— | —COOCH$_2$CH$_3$ | —H | ND | ND | ND | ND |
| 46 | —C(=O)— | —C$_2$F$_5$ | —H | + | + | + | + |
| 47 | —C(=O)CF$_2$— | —COOCH$_3$ | —H | + | + | + | + |
| 48 | —C(=O)C$_2$F$_4$— | —COOH | —H | + | + | + | + |
| 49 | —C(=O)CH$_2$— | —NH$_2$ | —H | + | + | + | + |
| 50 | —C(=O)— | —CF$_2$CO$_2$H | —H | ND | ND | ND | ND |
| 51 | —C(=O)— | —CF$_2$N(CH$_3$)$_2$ | —H | ND | ND | ND | ND |

DU-145: Prostate cancer cell line
BT-20: Breast Cancer cell line
+ IC$_{50}$ below 10 micromolar
DLD-1: Colorectal cell line
H-157: Non-small cell lung carcinoma cell
ND: IC$_{50}$ Not determined FIG. 1 depicts the dose response curves for the treatment of DLD-1, DU145, H157 and BT20 cells with (E)-2,4,6-Trimethoxystyryl-3-carboxymethylamino-4-methoxybenzylsulfone (Example 4). In this protocol, tumor cells were plated at a cell density of 1.0×10$^5$ cells in 6 well dishes. 24 hours after plating, (E)-2,4,6-trimethoxystyryl-3-carboxymethylamino-4-methoxybenzylsulfone (Example 4) was added to each well at the five indicated concentrations. The number of viable cells remaining after 96 hours of treatment was determined using hemacytometer following trypan blue staining. The number of variable cells has been plotted as the percent of Vehicle treated (control) cells.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound of formula I:

wherein:

X is selected from the group consisting of (i) and (ii) below:

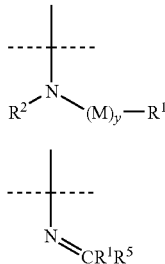

(i)

(ii)

$X^1$ is selected from the group consisting of (i), (ii) and (iii) below:

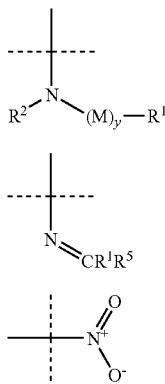

(i)

(ii)

(iii)

g is 0 or 1;

each M is a bivalent connecting group independently selected from the group consisting of —($C_1$-$C_6$)alkylene-, —$(CH_2)_a$—V—$(CH_2)_b$—, —$(CH_2)_d$—W—$(CH_2)_e$— and -Z-;

each y is independently selected from the group consisting of 0 and 1;

each V is independently selected from, the group consisting of arylene, heteroarylene, —C(=O)—, —C(=S)—, —S(=O)—, —$SO_2$—, —C(=O)O—; —C(=O)($C_1$-$C_6$)perfluoroalkylene-, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

-Z- is

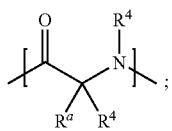

wherein the absolute stereochemistry of -Z- is D or L or a mixture of D and L;

each $R^a$ is independently selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

each $R^1$ is independently selected from the group consisting of unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$, —($C_1$-$C_6$)perfluoroalkyl, —$CF_2Cl$, —P(=O)($OR^4$)$_2$, —OP(=O)($OR^4$)$_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —($C_1$-$C_6$)alkyl, and aryl($C_1$-$C_3$)alkyl, wherein —$R^2$ and -(M)$_y$-$R^1$ may optionally be linked covalently to form a 5-, 6- or 7-membered substituted or unsubstituted heterocycle;

each $R^3$ is independently selected from —($C_1$-$C_6$)alkyl;

each $R^4$ is independently selected from the group consisting of —H, and —($C_1$-$C_6$)alkyl;

each $R^5$ is independently selected from the group consisting of —H, —($C_1$-$C_6$)alkyl and —($C_1$-$C_6$)acyl;

each $R^6$ is independently selected from the group consisting of —($C_1$-$C_6$)alkyl, —$CO_2R^5$, —C(=O)$R^7$, —$OR^5$, —OC(=O)($CH_2$)$_2CO_2R^5$, —$SR^4$, guanidine, —$NR^4_2$, —$NR^4_3{}^+$, —$N^+(CH_2CH_2OR^5)_3$, phenyl, substituted phenyl, heterocyclic, substituted heterocyclic and halogen;

each $R^7$ is independently selected from the group consisting of —$R^a$, halogen, —$NR^4_2$, and heterocycles containing two nitrogen atoms; and Q is selected from the group consisting of —H, —($C_1$-$C_6$) alkoxy, halogen, —($C_1$-$C_6$)alkyl and —$NR^4_2$;

wherein the substituents for the substituted aryl and substituted heterocyclic groups comprising or included within $R^1$, $R^2$, $R^a$, $R^6$ and $R^7$, are independently selected from the group consisting of halogen, ($C_1$-$C_6$)alkyl, —$NO_2$, —C≡N, —$CO_2R^5$, —C(=O)O($C_1$-$C_3$)alkyl, —$OR^5$, —($C_2$-$C_6$)alkylene-OH, phosphonato, —$NR^4_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$;

provided:

(1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)$NR^4$ or —$SO_2NR^4$, and b is 0, then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —$NR^4$—, —S— or —O—, and e is 0,
then said peptidyl moiety is coupled to M through the carboxy terminus of the peptidyl moiety or through a sidechain carboxyl group to form a carboxamide, carbothioic acid ester or carboxylic ester respectively;
or a salt of such a compound.

2. A compound according to claim 1 wherein:
each V is independently selected from the group consisting of

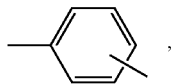

—C(=O)—, —C(=S)—, —S(=O)—, —SO$_2$—, —C(=O)O—; —C(=O)(C$_1$-C$_6$)perfluoroalkylene-, —C(=O)NR$^4$—, —C(=S)NR$^4$— and —SO$_2$NR$^4$—;
or a salt of such a compound.

3. A compound according to claim 1 wherein:
each V is independently selected from the group consisting of

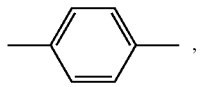

—C(=O)—, —C(=S)—, —S(=O)—, —SO$_2$—, —C(=O)O—; —C(=O)(C$_1$-C$_6$)perfluoroalkylene-, —C(=O)NR$^4$—, —C(=S)NR$^4$— and —SO$_2$NR$^4$—;
or a salt of such a compound.

4. A compound according to claim 1 selected from the group consisting of:
(E)-2,4,6-trimethoxystyryl-3-[4-(4-methylpiperazin-1-yl)benzamido]-4-methoxybenzylsulfone;
(E)-2,4,6-trimethoxystyryl-3-(acetoxyacetamido)-4-methoxybenzylsulfone;
(E)-2,4,6-trimethoxystyryl-3-(triethylammoniumacetamido)-4-methoxybenzylsulfone;
(E)-2,4,6-trimethoxystyryl-3-[tri-(2-hydroxyethylammonium)acetamido]-4-methoxybenzylsulfone;
(E)-2,4,6-trimethoxystyryl-3-(2-methyl-2-hydroxypropionamido)-4-methoxybenzylsulfone;
(E)-2,4,6-trimethoxystyryl-3-(2-methyl-2-acetoxypropionamido)-4-methoxybenzylsulfone;
(E)-2,4,6-trimethoxystyryl-3-(2-acetoxypropionamido)-4-methoxybenzylsulfone;
(E)-2,4,6-trimethoxystyryl-3-(trifluoroacetamido)-4-methoxybenzylsulfone;
(E)-2,4,6-trimethoxystyryl-3-(trifluoromethanesulfonamido)-4-methoxybenzylsulfone;
(E)-2,4,6-trimethoxystyryl-3-[3-(3-carboxypropanoyloxy)acetamido]-4-methoxybenzylsulfone;
(E)-2,4,6-trimethoxystyryl-3-(diethylphosphonatoacetamido)-4-methoxybenzylsulfone;
(E)-2,4,6-trimethoxystyryl-3-(phosphonatoacetamido)-4-methoxybenzylsulfone, disodium salt;
(E)-2,4,6-trimethoxystyryl-3-(methoxycarbonylamino)-4-methoxybenzylsulfone;
(E)-2,4,6-trimethoxystyryl-3-(pentafluoropropionamido)-4-methoxybenzylsulfone;
(E)-2,4,6-trimethoxystyryl-3-[(methyl-(2,2difluoro)malonamido]-4-methoxybenzylsulfone;
(E)-2,4,6-trimethoxystyryl-3-(2,2-difluoro-malonamido)-4-methoxybenzylsulfone;
(E)-2,4,6-trimethoxystyryl-3-(dimethylamino-α,α-difluoroacetamido)-4-methoxybenzylsulfone;
and (E)-2,4,6-trimethoxystyryl-3-(2,2,3,3-tetrafluoroethylsuccinamido)-4-methoxybenzylsulfone;
or a salt of such a compound.

5. A compound according to claim 1 wherein:
each V is independently selected from the group consisting of —C(=O)—, —C(=S)—, —S(=O)—, —SO$_2$—; —C(=O)NR$^4$—, —C(=S)NR$^4$— and —SO$_2$NR$^4$—;
-Z- is

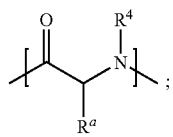

wherein the absolute stereochemistry of -Z- is either D or L;
each $R^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;
each $R^1$ is independently selected from the group consisting, of unsubstituted aryl, substituted aryl, substituted heterocyclic, unsubstituted heterocyclic, —CO$_2$R$^5$, —C(=O)NR$^4$$_2$, —CHR$^6$R$^7$, —C(=NH)—NR$^4$$_2$, and a monovalent peptidyl moiety with a molecular weight of less than 1000; provided that when y is 0 and $R^1$ is —CO$_2$R$^5$, $R^5$ is not —H;
each $R^6$ is independently selected from the group consisting of —(C$_1$-C$_6$)alkyl, —CO$_2$R$^5$, —C(=O)R$^7$, —OH, —SR$^4$, —(C$_1$-C$_3$)alkoxy, —(C$_1$-C$_3$)alkylthio, guanidino, —NR$^4$$_2$, phenyl, substituted phenyl, heterocyclic, substituted heterocyclic and halogen; and
each $R^7$ is independently selected from the group consisting of —H, halogen, —(C$_1$-C$_6$)alkyl, —NR$^4$$_2$ and heterocycles containing two nitrogen atoms;
wherein the substituents for the substituted aryl and substituted heterocyclic groups comprising or included within $R^1$, $R^a$, $R^6$ and $R^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O (C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
or a salt of such a compound.

6. A compound according to claim 5 wherein:
X is

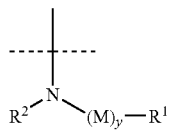

(i)

y is 0; and $R^2$ is —H;
or a salt of such a compound.

7. A compound according to claim 5, wherein:
$R^2$ is —H and y is 0;
g is 0; and
$R^1$ is selected from the group consisting of unsubstituted aryl, substituted aryl, substituted heterocyclic, unsubstituted heterocyclic, —$CO_2R^5$, —C(=O)$NR^4{}_2$, —$CHR^6R^7$, —C(=NH)—$NR^4{}_2$ and a monovalent peptidyl moiety with a molecular weight of less than 1000; provided that when y is 0 and $R^1$ is —$CO_2R^5$, $R^5$ is not —H;
or a salt of such a compound.

8. A compound according to claim 5, wherein:
X is

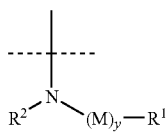

(i)

y is 1;
M is —$(CH_2)_a$—V—$(CH_2)_b$—;
V is —C(=O)—;
or a salt of such a compound.

9. A compound according to claim 8, having the formula IV:

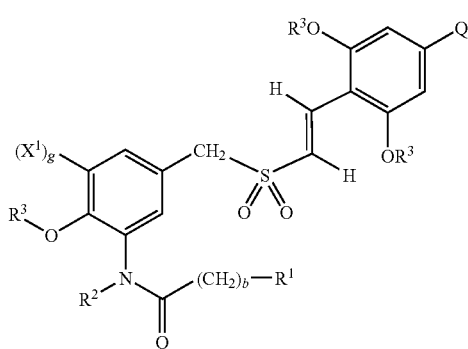

IV wherein:
$X^1$ is selected from the group consisting of (i), (ii) and (iii) below:

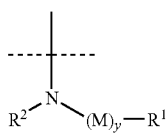

(i)

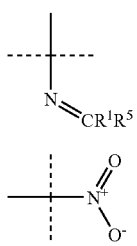

(ii)

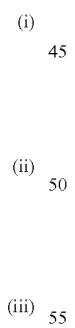

(iii)

g is 0 or 1;
M is a bivalent connecting group selected from the group consisting of —($C_1$-$C_6$)alkylene-, —$(CH_2)_a$—V—$(CH_2)_b$—, —$(CH_2)_d$—W—$(CH_2)_e$— and -Z-;
y is selected from the group consisting of 0 and 1;
V is selected from the group consisting of —C(=O)—, —C(=S)—, —S(=O)—, —$SO_2$—, —C(=O)$NR^4$—, —C(=S)$NR^4$— and —$SO_2NR^4$—;

W is selected from the group consisting of —$NR^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3;
-Z- is

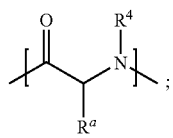

wherein the absolute stereochemistry of -Z- is either D or L; and
$R^a$ is selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;
wherein the substituents for the substituted aryl and substituted heterocyclic groups comprising or included within $R^1$, $R^a$, $R^2$, $R^6$ and $R^7$, are independently selected from the group consisting of halogen, ($C_1$-$C_6$)alkyl, ($C_1$-$C_6$)alkoxy, —$NO_2$, —C≡N, —$CO_2R^5$, —C(=O)O($C_1$-$C_3$)alkyl, —OH, —($C_2$-$C_6$)alkylene-OH, phosphonato, —$NR^4{}_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$;
provided:
  (1) when $R^1$ is a monovalent peptidyl moiety of molecular weight less than 1000 and V is —C(=O)—, —C(=S)—, —S(=O)— or —$SO_2$—, and b is 0;
  then said peptidyl moiety is coupled to M through the amino terminus of the peptidyl moiety or through a sidechain amino group to form an amide, thioamide, sulfinamide or sulfonamide respectively;
  (2) when $R^1$ is a monovalent peptidyl moiety of molecular weight less than 1000 and V is —C(=O)$NR^4$— or —$SO_2NR^4$—, and b is 0,
  then said peptidyl moiety is coupled to M through the carboxy terminus of the peptidyl moiety or through a sidechain carboxyl group to form an imide or sulfonimide, respectively; and
  (3) when $R^1$ is a monovalent peptidyl moiety of molecular weight less than 1000 and W is —$NR^4$—, —S— or —O—, and e is 0,
  then said peptidyl moiety is coupled to M through the carboxy terminus of the peptidyl moiety or through a sidechain carboxyl group to form a carboxamide, carbothioic acid ester or carboxylic ester respectively;
or a salt of such a compound.

10. A compound according to claim 9, wherein g is 0; or a salt of such a compound.

11. A compound according to claim 10 selected from the group consisting of:
(E)-2,4,6-trimethoxystyryl-3-(carboxyacetamido)-4-methoxybenzylsulfone;

(E)-2,4,6-trimethoxystyryl-3-(3,5-dinitrobenzamido)-4-methoxybenzylsulfone;
(E)-2,4,6-trimethoxystyryl-3-(3,5-diaminobenzamido)-4-methoxybenzylsulfone;
(E)-2,4,6-trimethoxystyryl-3-(chloroacetamido)-4-methoxybenzylsulfone;
(E)-2,4,6-trimethoxystyryl-3-[(4-methylpiperazinyl)acetamido]-4-methoxybenzylsulfone;
(E)-2,4,6-trimethoxystyryl-3-(benzamido)-4-methoxybenzylsulfone;
(E)-2,4,6-trimethoxystyryl-3-(4-nitrobenzamido)-4-methoxybenzylsulfone;
(E)-2,4,6-trimethoxystyryl-3-(4-aminobenzamido)-4-methoxybenzylsulfone;
(E)-2,4,6-trimethoxystyryl-3-(dimethylaminoacetamido)-4-methoxybenzylsulfone;
(E)-2,4,6-trimethoxystyryl-3-(hydroxyacetamido)-4-methoxybenzylsulfone;
(E)-2,4,6-trimethoxystyryl-3-(2-hydroxypropionamido)-4-methoxybenzylsulfone
(E)-2,4,6-trimethoxystyryl-3-(pyridinium-1-yl)acetamido-4-methoxybenzylsulfone;
(E)-2,4,6-trimethoxystyryl-3(ethylmalonamido)-4-methoxybenzylsulfone;
(E)-2,4,6-trimethoxystyryl-3-(glutaramido)-4-methoxybenzylsulfone
(E)-2,4,6-trimethoxystyryl-3-(methylsuccinamido)-4-methoxybenzylsulfone;
(E)-2,4,6-trimethoxystyryl-3-succinamido-4-methoxybenzylsulfone; and
(E)-2,4,6-trimethoxystyryl-3-(aminoacetamido)-4-methoxybenzylsulfone;
or a salt of such a compound.

12. A compound according to claim 5 wherein:
X is

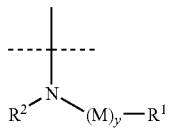

y is 1; and M is -Z-; or a salt of such a compound.

13. A compound according to claim 12, having the formula V:

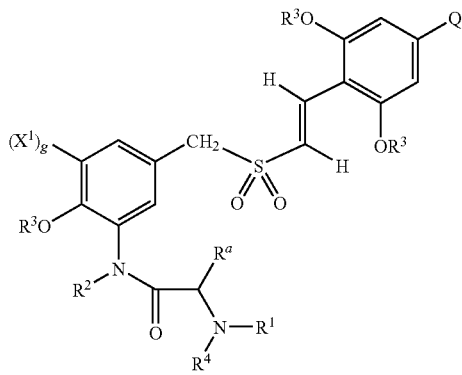

wherein:
X$^1$ is selected from the group consisting of (i), (ii) and (iii) below:

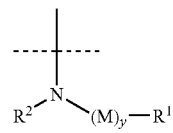 (i)

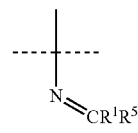 (ii)

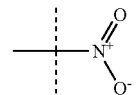 (iii)

g is 0 or 1;
M is a bivalent connecting group selected from the group consisting of —(C$_1$-C$_6$)alkylene-, —(CH$_2$)$_a$—V—(CH$_2$)$_b$—, —(CH$_2$)$_d$—W—(CH$_2$)$_e$— and -Z-;
y is selected from the group consisting of 0 and 1;
V is selected from the group consisting of —C(=O)—, —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3; and
-Z- is

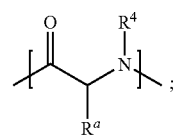

wherein the absolute stereochemistry of -Z- is either D or L; and
wherein the substituents for the substituted aryl and substituted heterocyclic groups comprising or included within R$^1$, R$^a$, R$^2$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
provided:
(1) when R$^1$ is a monovalent peptidyl moiety of molecular weight less than 1000 and V is —C(=O)—, —C(=S)—, —S(=O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)NR$^4$— or —SO$_2$NR$^4$—, and b is 0, then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —NR$^4$—, —S— or —O—, and e is 0, then said peptidyl moiety is coupled to M through the carboxy terminus of the peptidyl moiety or through a sidechain carboxyl group to form a carboxamide, carbothioic acid ester or carboxylic ester respectively;

or a salt of such a compound.

14. A compound according to claim 13, wherein g is 0; or a salt of such a compound.

15. A compound according to claim 5, wherein:
X is

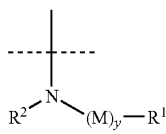
(i)

y is 1; M is —(CH$_2$)$_a$—V—(CH$_2$)$_b$—; and V is —SO$_2$—; or a salt of such a compound.

16. A compound according to claim 15, having the formula VI:

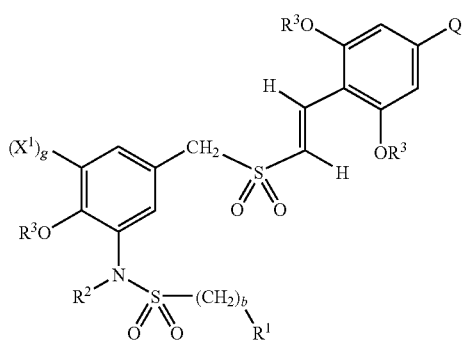
VI wherein:
X$^1$ is selected from the group consisting of (i), (ii) and (iii) below:

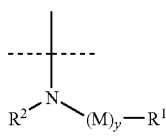
(i)

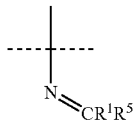
(ii)

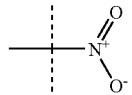
(iii)

g is 0 or 1;
M is a bivalent connecting group selected from the group consisting of —(C$_1$-C$_6$)alkylene-, —(CH$_2$)$_a$—V—(CH$_2$)$_b$—, —(CH$_2$)$_d$—W—(CH$_2$)$_e$— and -Z-;
y is selected from the group consisting of 0 and 1;
V is selected from the group consisting of —C(=O)—, —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3;
-Z- is

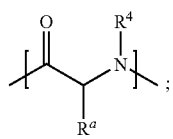

wherein the absolute stereochemistry of -Z- is either D or L; and
R$^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein R$^a$ and R$^1$ combine to form a 5-, 6- or 7-membered heterocyclic ring;
wherein the substituents for the substituted aryl and substituted heterocyclic groups comprising or included within R$^1$, R$_a$, R$^2$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
provided:
(1) when R$^1$ is a monovalent peptidyl moiety of molecular weight less than 1000 and V is —C(=O)—, —C(=S)—, —S(=O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;
(2) when R$^1$ is a monovalent peptidyl moiety of molecular weight less than 1000 and V is —C(=O)NR$^4$— or —SO$_2$NR$^4$—, and b is 0,
then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —$NR^4$—, —S— or —O—, and e is 0, then said peptidyl moiety is coupled to M through the carboxy terminus of the peptidyl moiety or through a sidechain carboxyl group to form a carboxamide, carbothioic acid ester or carboxylic ester respectively;

or a salt of such a compound.

17. A compound according to claim 16, wherein g is 0; or a salt of such a compound.

18. A compound according to claim 17 selected from the group consisting of:
(E)-2,4,6-trimethoxystyryl-3-(carboxymethylsulfamyl)-4-methoxybenzylsulfone;
(E)-2,4,6-trimethoxystyryl-3-(4-methoxybenzenesulfamyl)-4-methoxybenzylsulfone;
(E)-2,4,6-trimethoxystyryl-3-(2,4-dinitrobenzenesulfamyl)-4-methoxybenzylsulfone;
(E)-2,4,6-trimethoxystyryl-3-(2,4-diaminobenzenesulfamyl)-4-methoxybenzylsulfone;
or a salt of such a compound.

19. A compound according to claim 5 wherein:
X is

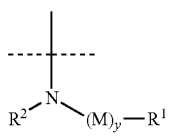

(i)

y is 0; and
$R^1$ is —C(=NH)—$NR^4_2$;
or a salt of such a compound.

20. A compound according to claim 5 having the formula VII:

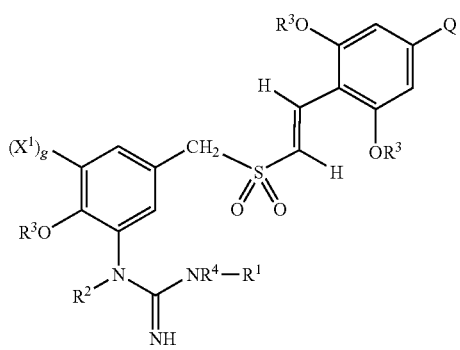

VII wherein:
$X^1$ is selected from the group consisting of (i), (ii) and (iii) below:

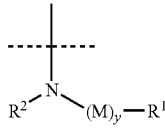

(i)

-continued

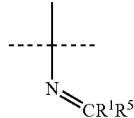

(ii)

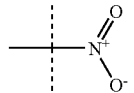

(iii)

g is 0 or 1;
M is a bivalent connecting group selected from the group consisting of —($C_1$-$C_6$)alkylene-, —$(CH_2)_a$—V—$(CH_2)_b$—, —$(CH_2)_d$—W—$(CH_2)_e$— and -Z-;
y is selected from the group consisting of 0 and 1;
V is selected from the group consisting of —C(=O)—, —C(=S)—, —S(=O)—, —$SO_2$—, —C(=O)$NR^4$—, —C(=S)$NR^4$— and —$SO_2NR^4$—;
W is selected from the group consisting of —$NR^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3;
-Z- is

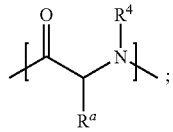

wherein the absolute stereochemistry of -Z- is either D or L;
$R^a$ is selected from the group consisting of —H, —$CH_3$, —$(CH_2)_3$—NH—C($NH_2$)(=NH), —$CH_2$C(=O)$NH_2$, —$CH_2COOH$, —$CH_2SH$, —$(CH_2)_2$C(=O)—$NH_2$, —$(CH_2)_2COOH$, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring; and
$R^1$ is selected from the group consisting of unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H;
wherein the substituents for the substituted aryl and substituted heterocyclic groups comprising or included within $R^1$, $R^a$, $R^2$, $R^6$ and $R^7$, are independently selected from the group consisting of halogen, ($C_1$-$C_6$)alkyl, ($C_1$-$C_6$)alkoxy, —$NO_2$, —C≡N, —$CO_2R^5$, —C(=O)O($C_1$-$C_3$)alkyl, —OH, —($C_2$-$C_6$)alkylene-OH, phosphonato, —$NR^4_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$;

provided:
(1) when $R^1$ is a monovalent peptidyl moiety of molecular weight less than 1000 and V is —C(═O)—, —C(═S)—, —S(═O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;
(2) when $R^1$ is a monovalent peptidyl moiety of molecular weight less than 1000 and V is —C(═O)NR$^4$— or —SO$_2$NR$^4$—, and b is 0,
then said peptidyl moiety is coupled to M through the carboxy terminus of the peptidyl moiety or through a sidechain carboxyl group to form an imide or sulfonimide, respectively; and
(3) when $R^1$ is a monovalent peptidyl moiety of molecular weight less than 1000 and W is —NR$^4$—, —S— or —O—, and e is 0,
then said peptidyl moiety is coupled to M through the carboxy terminus of the peptidyl moiety or through a sidechain carboxyl group to form a carboxamide, carbothioic acid ester or carboxylic ester respectively;
or a salt of such a compound.

21. A compound according to claim 20, wherein g is 0, or a salt of such a compound.

22. A compound according to claim 19 wherein said compound is (E)-2,4,6-trimethoxystyryl-3-guanidino-4-methoxybenzylsulfone; or a salt of such a compound.

23. A compound according to claim 5 wherein:
X is

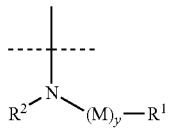
(i)

y is 1; and M is —(C$_1$-C$_6$)alkylene;
or a salt of such a compound.

24. A compound according to claim 23 having the formula VIII:

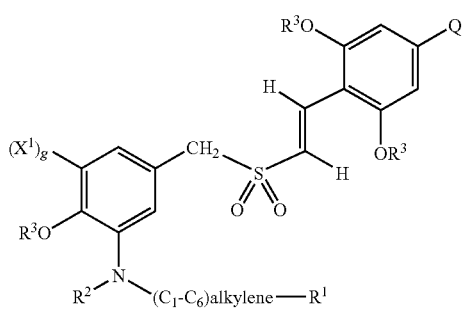
VIII wherein:
$X^1$ is selected from the group consisting of (i), (ii) and (iii) below:

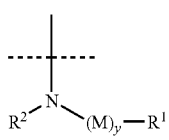
(i)

(ii)

(iii)

g is 0 or 1;
M is a bivalent connecting group selected from the group consisting of —(C$_1$-C$_6$)alkylene-, —(CH$_2$)$_a$—V—(CH$_2$)$_b$—, —(CH$_2$)$_d$—W—(CH$_2$)$_e$— and -Z-;
y is selected from the group consisting of 0 and 1;
V is selected from the group consisting of, —C(═O)—, —C(═S)—, —S(═O)—, —SO$_2$—, —C(═O)NR$^4$—, —C(═S)NR$^4$— and —SO$_2$NR$^4$—;
W is selected from the group consisting of —NR$^4$—, —O— and —S—;
a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3;
-Z- is

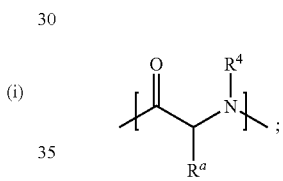

wherein the absolute stereochemistry of -Z- is either D or L; and
$R^a$ is selected from the group consisting of —H, —CH$_3$, —(CH$_2$)$_3$—NH—C(NH$_2$)(═NH), —CH$_2$C(═O)NH$_2$, —CH$_2$COOH, —CH$_2$SH, —(CH$_2$)$_2$C(═O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;
wherein the substituents for the substituted aryl and substituted heterocyclic groups comprising or included within $R^1$, $R^a$, $R^2$, $R^6$ and $R^7$, are independently selected from the group consisting of halogen, (C$_1$-C$_6$)alkyl, (C$_1$-C$_6$)alkoxy, —NO$_2$, —C≡N, —CO$_2$R$^5$, —C(═O)O(C$_1$-C$_3$)alkyl, —OH, —(C$_2$-C$_6$)alkylene-OH, phosphonato, —NR$^4$$_2$, —NHC(═O)(C$_1$-C$_6$)alkyl, sulfamyl, —OC(═O)(C$_1$-C$_3$)alkyl, —O(C$_2$-C$_6$)alkylene-N((C$_1$-C$_6$)alkyl)$_2$ and —CF$_3$;
provided:
(1) when $R^1$ is a monovalent peptidyl moiety of molecular weight less than 1000 and V is —C(═O)—, —C(═S)—, —S(═O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)NR$^4$— or —SO$_2$NR$^4$—, and b is 0,
then said peptidyl moiety is coupled to M through the carboxy terminus of the peptidyl moiety or through a sidechain carboxyl group to form an imide or sulfonimide, respectively; and
(3) when $R^1$ is a monovalent peptidyl moiety of molecular weight less than 1000 and W is —NR$^4$—, —S— or —O—, and e is 0,
then said peptidyl moiety is coupled to M through the carboxy terminus of the peptidyl moiety or through a sidechain carboxyl group to form a carboxamide, carbothioic acid ester or carboxylic ester respectively;
or a salt of such a compound.

25. A compound according to claim 24, wherein g is 0; or a salt of such a compound.

26. A compound according to claim 1 having the formula IX:

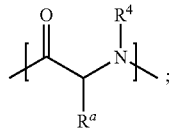

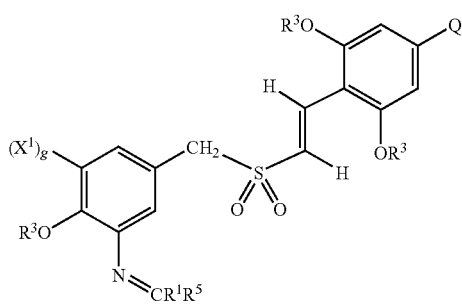

wherein:
$X^1$ is selected from the group consisting of (i), (ii) and (iii) below:

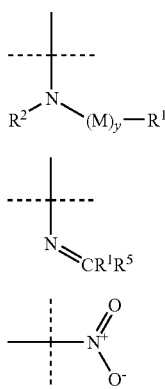

g is 0 or 1;
M is a bivalent connecting group selected from the group consisting of —(C$_1$-C$_6$)alkylene-, —(CH$_2$)$_a$—V—(CH$_2$)$_b$—, —(CH$_2$)$_d$—W—(CH$_2$)$_e$— and -Z-;
y is selected from the group consisting of 0 and 1;
V is selected from the group consisting of —C(=O)—, —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3;
-Z- is $$\ce{ \underset{R^a}{\overset{O}{\|}} }$$

wherein the absolute stereochemistry of -Z- is either D or L;
$R^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;
each $R^1$ is independently selected from the group consisting of unsubstituted aryl, substituted aryl, substituted heterocyclic, unsubstituted heterocyclic, —CO$_2$R$^5$, —C(=O)NR$^4$$_2$, —CHR$^6$R$^7$, —C(=NH)—NR$^4$$_2$ and a monovalent peptidyl moiety with a molecular weight of less than 1000; provided that when y is 0 and $R^1$ is —CO$_2$R$^5$, $R^5$ is not —H;
each $R^6$ is independently selected from the group consisting of —(C$_1$-C$_6$)alkyl, —CO$_2$R$^5$, —C(=O)R$^7$, —OH, —SR$^4$, —(C$_1$-C$_3$)alkoxy, —(C$_1$-C$_3$)alkylthio, guanidino, —NR$^4$$_2$, phenyl, substituted phenyl, heterocyclic, substituted heterocyclic and halogen; and
each $R^7$ is independently selected from the group consisting of —H, halogen, —(C$_1$-C$_6$)alkyl, —NR$^4$$_2$, and heterocycles containing two nitrogen atoms; and
wherein the substituents for the substituted aryl and substituted heterocyclic groups comprising or included within $R^1$, $R^a$, $R^2$, $R^6$ and $R^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
provided:
(1) when $R^1$ is a monovalent peptidyl moiety of molecular weight less than 1000 and V is —C(=O)—, —C(=S)—, —S(=O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;
(2) when $R^1$ is a monovalent peptidyl moiety of molecular weight less than 1000 and V is —C(=O)NR$^4$— or —SO$_2$NR$^4$—, and b is 0,
then said peptidyl moiety is coupled to M through the carboxy terminus of the peptidyl moiety or through a sidechain carboxyl group to form an imide or sulfonimide, respectively; and
(3) when $R^1$ is a monovalent peptidyl moiety of molecular weight less than 1000 and W is —NR$^4$—, —S— or —O—, and e is 0, then said peptidyl moiety is coupled to M through the carboxy terminus of the peptidyl moiety or through a sidechain carboxyl group to form a carboxamide, carbothioic acid ester or carboxylic ester respectively;

or a salt of such a compound.

27. A compound according to claim 26, wherein g is 0; or a salt of such a compound.

28. A compound according to claim 27 wherein said compound is (E)-2,4,6-trimethoxystyryl-3-(4-nitrophenylimino)-4-methoxybenzylsulfone; or a salt of such a compound.

29. A compound according to claim 1 wherein:
X is

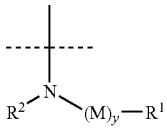

(i)

y is 1; M is —$(CH_2)_a$—V—$(CH_2)_b$—; and V is —C(=O)NR$^4$—; or a salt of such a compound.

30. A compound according to claim 29 having the formula X:

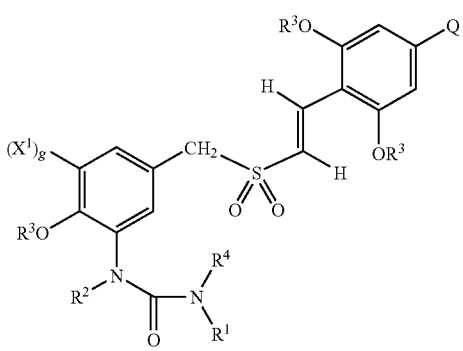

X wherein:
$X^1$ is selected from the group consisting of (i), (ii) and (iii) below:

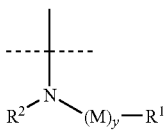

(i)

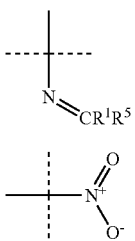

(ii)

(iii)

g is 0 or 1;
M is a bivalent connecting group selected from the group consisting of —$(C_1-C_6)$alkylene-, —$(CH_2)_a$—V—$(CH_2)_b$—, —$(CH_2)_d$—W—$(CH_2)_e$— and -Z-;
y is selected from the group consisting of 0 and 1;
V is selected from the group consisting of —C(=O)—, —C(=S)—, —S(=O)—, —$SO_2$—, —C(=O)NR$^4$—, —C(=S)NR$^4$— and —$SO_2$NR$^4$—;
W is selected from the group consisting of —NR$^4$—, —O— and —S—;
a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3;
-Z- is

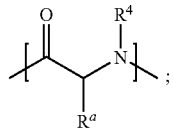

wherein the absolute stereochemistry of -Z- is either D or L; and $R^a$ is selected from the group consisting of —H, —$CH_3$, —$(CH_2)_3$—NH—C(NH$_2$)(=NH), —$CH_2$C(=O)NH$_2$, —$CH_2$COOH, —$CH_2$SH, —$(CH_2)_2$C(=O)—NH$_2$, —$(CH_2)_2$COOH, —$CH_2$-(2-imidazolyl), —CH(CH$_3$)—$CH_2$—$CH_3$, —$CH_2$CH(CH$_3$)$_2$, —$(CH_2)_4$—NH$_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH(CH$_3$)$_2$ and —$CH_2$—$CH_3$; and includes compounds wherein $R^a$ and $R^1$ combine to form a 5-, 6- or 7-membered heterocyclic ring;

wherein the substituents for the substituted aryl and substituted heterocyclic groups comprising or included within $R^1$, $R^a$, $R^2$, $R^6$ and $R^7$, are independently selected from the group consisting of halogen, $(C_1-C_6)$alkyl, $(C_1-C_6)$alkoxy, —$NO_2$, —C≡N, —$CO_2R^5$, —C(=O)O$(C_1-C_3)$alkyl, —OH, —$(C_2-C_6)$alkylene-OH, phosphonato, —NR$^4{}_2$, —NHC(=O)$(C_1-C_6)$alkyl, sulfamyl, —OC(=O)$(C_1-C_3)$alkyl, —O$(C_2-C_6)$alkylene-N$((C_1-C_6)$alkyl)$_2$ and —$CF_3$;

provided:

(1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)NR$^4$— or —$SO_2$NR$^4$—, and b is 0, then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —NR$^4$—, —S— or —O—, and e is 0, then said peptidyl moiety is coupled to M through the carboxy terminus of the peptidyl moiety or through a sidechain carboxyl group to form a carboxamide, carbothioic acid ester or carboxylic ester respectively;

or a salt of such a compound.

31. A compound according to claim 30, wherein g is 0; or a salt of such a compound.

32. A compound according to claim 1 wherein:
X is

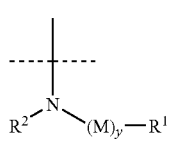

(i)

y is 0; $R^1$ is —CHR$^6$R$^7$; $R^6$ is $CO_2R^5$ and $R^7$ is $R^a$; or a salt of such a compound.

33. A compound according to claim 32 of formula XX:

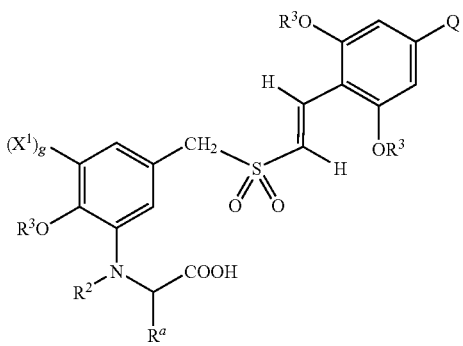

wherein:

$X^1$ is selected from the group consisting of (i), (ii) and (iii) below:

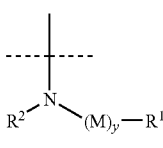 (i)

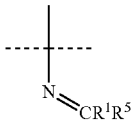 (ii)

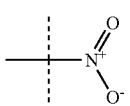 (iii)

g is 0 or 1;

M is a bivalent connecting group selected from the group consisting of —$(C_1\text{-}C_6)$alkylene-, —$(CH_2)_a$—V—$(CH_2)_b$—, —$(CH_2)_d$—W—$(CH_2)_e$— and -Z-;

y is selected from the group consisting of 0 and 1;

V is selected from the group consisting of arylene, heteroarylene, —C(=O)—, —C(=S)—, —S(=O)—, —$SO_2$—, —C(=O)O—; —C(=O)$(C_1\text{-}C_6)$perfluoroalkylene-, —C(=O)$NR^4$—, —C(=S)$NR^4$— and —$SO_2NR^4$—;

W is selected from the group consisting of —$NR^4$—, —O— and —S—;

a is selected from the group consisting of 0, 1, 2 and 3;

b is selected from the group consisting of 0, 1, 2 and 3;

d is selected from the group consisting of 1, 2 and 3;

e is selected from the group consisting of 0, 1, 2 and 3;

-Z- is

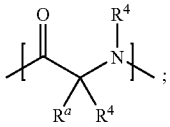

wherein the absolute stereochemistry of -Z- is D, L or a mixture of D and L;

$R^1$ is selected from the group consisting of unsubstituted aryl, substituted aryl, substituted heterocyclic, unsubstituted heterocyclic, —$CO_2R^5$, —C(=O)$NR^4{}_2$, —$CR^4R^6R^7$, —C(=NH)—$NR^4{}_2$, —$(C_1\text{-}C_6)$perfluoroalkyl, —$CF_2Cl$, —P(=O)$(OR^4)_2$, —OP(=O)$(OR^4)_2$, and a monovalent peptidyl moiety with a molecular weight of less than 1000; provided that when y is 0 and $R^1$ is —$CO_2R^5$, $R^5$ is not —H;

$R^4$ is selected from the group consisting of —H, and —$(C_1\text{-}C_6)$alkyl;

$R^5$ is selected from the group consisting of —H, —$(C_1\text{-}C_6)$alkyl and —$(C_1\text{-}C_6)$acyl;

$R^6$ is selected from the group consisting of —$(C_1\text{-}C_6)$alkyl, —$CO_2R^5$, —C(=O)$R^7$, —$OR^5$, —$SR^4$, guanidino, —$NR^4{}_2$, —$N^+(CH_2CH_2OH)_3$, —$NR^4{}_3{}^+$, phenyl, substituted phenyl, heterocyclic, substituted heterocyclic and halogen; and $R^7$ is selected from the group consisting of $R^a$, halogen, —$NR^4{}_2$, and heterocycles containing two nitrogen atoms;

wherein the substituents for the substituted aryl and substituted heterocyclic groups comprising or included within $R^1$, $R^2$, $R^a$, $R^6$ and $R^7$, are independently selected from the group consisting of halogen, $(C_1\text{-}C_6)$alkyl, $(C_1\text{-}C_6)$alkoxy, —$NO_2$, —C≡N, —$CO_2R^5$, —C(=O)O$(C_1\text{-}C_3)$alkyl, —$OR^5$, —$(C_2\text{-}C_6)$alkylene-OH, phosphonato, —$NR^4{}_2$, —NHC(=O)$(C_1\text{-}C_6)$alkyl, sulfamyl, —OC(=O)$(C_1\text{-}C_3)$alkyl, —O$(C_2\text{-}C_6)$alkylene-N$((C_1\text{-}C_6)$alkyl$)_2$ and —$CF_3$;

provided:

(1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)$NR^4$— or —$SO_2NR^4$—, and b is 0, then said peptidyl moiety is coupled to M through the carboxy terminus of the peptidyl moiety or through a sidechain carboxyl group to form an imide or sulfonimide, respectively; and (3) when $R^1$ is a monovalent peptidyl moiety of molecular weight less than 1000 and W is —$NR^4$—, —S— or —O—, and e is 0, then said peptidyl moiety is coupled to M through the carboxy terminus of the peptidyl moiety or through a sidechain carboxyl group to form a carboxamide, carbothioic acid ester or carboxylic ester respectively;

or a salt of such a compound.

34. A compound according to claim 33, wherein g is 0; or a salt of such a compound.

35. A compound according to claim 34 selected from the group consisting of:

racemic-(E)-2,4,6-trimethoxystyryl-3-(1-carboxyethyl)amino-4-methoxybenzylsulfone;

D-(E)-2,4,6-trimethoxystyryl-3-(1-carboxyethyl)amino-4-methoxybenzylsulfone; and L-(E)-2,4,6-trimethoxystyryl-3-(1-carboxyethyl)amino-4-methoxybenzylsulfone;

or a salt of such a compound.

36. A compound according to claim 35 selected from the group consisting of sodium and potassium salts.

37. A compound according to claim 36 wherein the compound is a sodium salt.

38. A compound according to claim 1 wherein:
X is

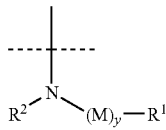

(i)

and y is 1; and M is —(C$_1$-C$_6$)alkylene-;
or a salt of such a compound.

39. A compound according to claim 38 of formula XXI:

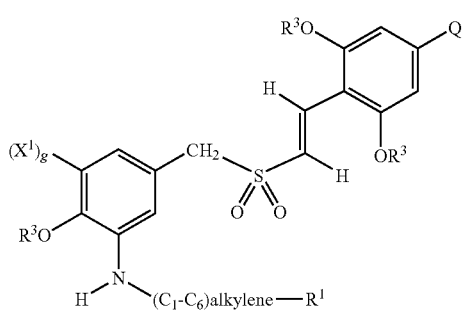

XXI wherein:
X$^1$ is selected from the group consisting of (i), (ii) and (iii) below:

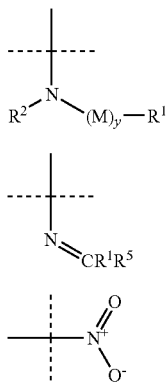

(i)

(ii)

(iii)

g is 0 or 1;
M is a bivalent connecting group selected from the group consisting of —(C$_1$-C$_6$)alkylene-, —(CH$_2$)$_a$—V—(CH$_2$)$_b$—, —(CH$_2$)$_d$—W—(CH$_2$)$_e$— and -Z-;
y is selected from the group consisting of 0 and 1;
V is selected from the group consisting of arylene, heteroarylene, —C(=O)—, —C(=S)—, —S(=O)—, —SO$_2$—, —C(=O)O—; —C(=O)(C$_1$-C$_6$)perfluoroalkylene-, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3;

-Z- is

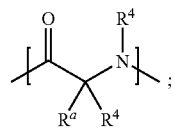

wherein the absolute stereochemistry of -Z- is D, L or a mixture of D and L;
R$^2$ is selected from the group consisting of —H, —(C$_1$-C$_6$) alkyl, and aryl(C$_1$-C$_3$)alkyl, wherein —R$^2$ and -(M)$_y$-R$^1$ may optionally be linked covalently to form a 5-, 6- or 7-membered substituted or unsubstituted heterocycle; and
each R$^6$ is independently selected from the group consisting of —(C$_1$-C$_6$)alkyl, —CO$_2$R$^5$, —C(=O)R$^7$, —OR$^5$, —SR$^4$, guanidino, —NR$^4{}_2$, —N$^+$(CH$_2$CH$_2$OH)$_3$, —NR$^4{}_3{}^+$, phenyl, substituted phenyl, heterocyclic, substituted heterocyclic and halogen;
wherein the substituents for the substituted aryl and substituted heterocyclic groups comprising or included within R$^1$, R$^2$, R$^a$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OR$^5$, —(C$_2$-C$_6$)alkylene-OH, phosphonato, —NR$^4{}_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
provided:
(1) when R$^1$ is a monovalent peptidyl moiety of molecular weight less than 1000 and V is —C(=O)—, —C(=S)—, —S(=O)— or —SO$_2$—, and b is 0;
then said peptidyl moiety is coupled to M through the amino terminus of the peptidyl moiety or through a sidechain amino group to form an amide, thioamide, sulfinamide or sulfonamide respectively;
(2) when R$^1$ is a monovalent peptidyl moiety of molecular weight less than 1000 and V is —C(=O)NR$^4$— or —SO$_2$NR$^4$—, and b is 0,
then said peptidyl moiety is coupled to M through the carboxy terminus of the peptidyl moiety or through a sidechain carboxyl group to form an imide or sulfonimide, respectively; and
(3) when R$^1$ is a monovalent peptidyl moiety of molecular weight less than 1000 and W is —NR$^4$—, —S— or —O—, and e is 0,
then said peptidyl moiety is coupled to M through the carboxy terminus of the peptidyl moiety or through a sidechain carboxyl group to form a carboxamide, carbothioic acid ester or carboxylic ester respectively;
or a salt of such a compound.

40. A compound according to claim 39 selected from the group consisting of:
(E)-2,4,6-trimethoxystyryl-3-(3-carboxypropylamino)-4-methoxybenzylsulfone; and
(E)-2,4,6-trimethoxystyryl-3-(2-carboxyethylamino)-4-methoxybenzylsulfone; or a salt of such a compound.

41. A process for preparing a compound of claim 1 comprising:

(1) coupling a compound of formula IIIa:

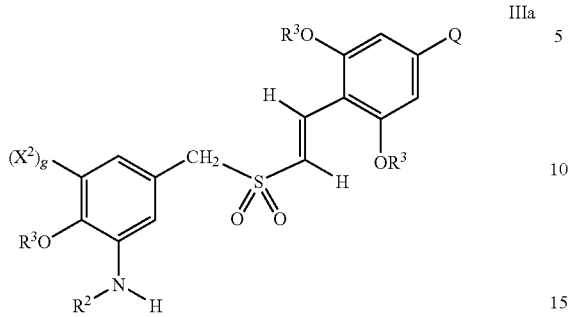

wherein:
$X^2$ is selected from the group consisting of —$NO_2$ and —$NH_2$, optionally protected with a chemical protecting group; and
g is 0 or 1;
or a salt of such a compound;
with a compound of formula XI:

$R^1$-A    XI wherein:
each $R^1$ is selected from the group consisting of unsubstituted aryl, substituted aryl, substituted heterocyclic, unsubstituted heterocyclic, —$CO_2R^5$, —C(=O)$NR^4{}_2$, —$CR^4R^6R^7$, —C(=NH)—$NR^4{}_2$, —($C_1$-$C_6$)perfluoroalkyl, —$CF_2Cl$, —P(=O)(O$R^4$)$_2$, —OP(=O)(O$R^4$)$_2$ and a monovalent peptidyl moiety with a molecular weight of less than 1000;
each $R^4$ is independently selected from the group consisting of —H, and —($C_1$-$C_6$)alkyl;
each $R^5$ is independently selected from the group consisting of —H, —($C_1$-$C_6$)alkyl and —($C_1$-$C_6$)acyl;
each $R^6$ is independently selected from the group consisting of —($C_1$-$C_6$)alkyl, —$CO_2R^5$, —C(=O)$R^7$, —$OR^5$, —OC(=O)($CH_2$)$_2$$CO_2R^5$, —$SR^4$, guanidino, —$NR^4{}_2$, —$NR^4{}_3{}^+$, —$N^+(CH_2CH_2OR^5)_3$, phenyl, substituted phenyl, heterocyclic, substituted heterocyclic and halogen;
each $R^7$ is independently selected from the group consisting of —$R^a$, halogen, —$NR^4{}_2$, and heterocycles containing two nitrogen atoms;
wherein the substituents for the substituted aryl and substituted heterocyclic groups comprising or included within $R^1$, —$R^a$, $R^6$ and $R^7$, are independently selected from the group consisting of halogen, ($C_1$-$C_6$)alkyl, ($C_1$-$C_6$)alkoxy, —$NO_2$, —C≡N, —$CO_2R^5$, —C(=O)O($C_1$-$C_3$)alkyl, —$OR^5$, —($C_2$-$C_6$)alkylene-OH, phosphonato, —$NR^4{}_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$; and wherein one or more functional groups comprising $R^1$ are optionally protected by chemical protecting groups; and
wherein A is a moiety containing an electrophilic reactive center, said moiety selected from the group consisting of:
(a) an alkyl moiety having a leaving group;
(b) an aryl halide or aryl pseudo halide;
(c) a carboxylic acid activated with a leaving group;
(d) a sulfonic acid activated with a leaving group;
(e) a carbamic acid moiety activated with a leaving group;
(f) a cyanate moiety;
(g) an aldehyde or ketone moiety, or a hydrate thereof or a ketal or acetal thereof;
(h) a carboxylic acid moiety and an amide coupling reagent; or
(i) the intermediate product of a thiourea moiety and 2-chloro-1-methyl pyridinium iodide;
to form a compound of formula Ia:

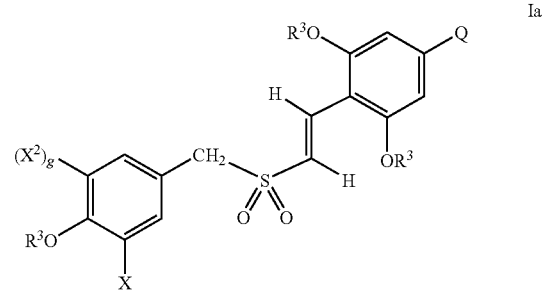

(2) optionally:
(a) when —$X^2$ is —$NH_2$ protected with a protecting group; removing said protecting group from —$X^2$ to yield a compound of formula Ib; or
(b) when —$X^2$ is —$NO_2$, chemically reducing said —$NO_2$ to —$NH_2$;
to form a compound of formula Ib:

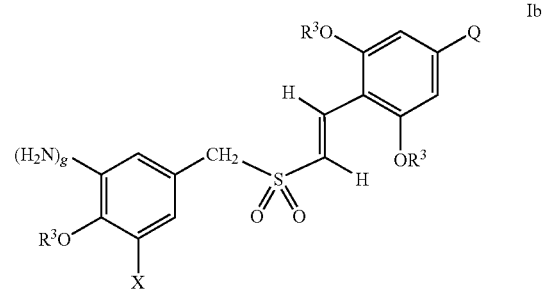

(3) optionally coupling said compound of formula Ib or a salt thereof:
with a compound of formula XI:

$R^1$-A    XI wherein one or more functional groups comprising $R^1$ are optionally protected by chemical protecting groups; and
wherein A is a moiety containing an electrophilic reactive center as defined above; and
(4) optionally removing said protecting groups protecting functionalities comprising $R^1$ to form a compound of formula I:

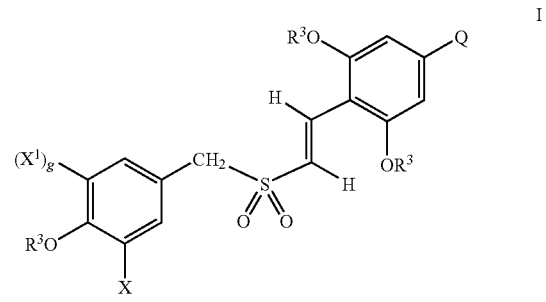

or a salt thereof.

42. A process according to claim 41 for preparing the compound of formula IIIa:

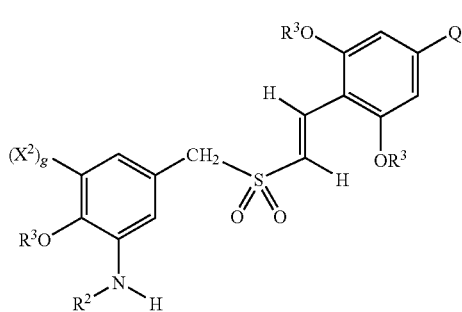

comprising: (1) chemically reducing a compound according to formula IIa:

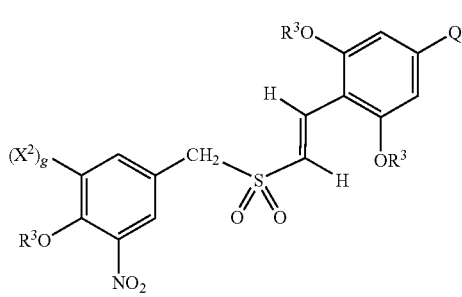

wherein
g is 0 or 1;
each $R^3$ is independently selected from —$(C_1$-$C_6)$alkyl;
each $R^4$ is independently selected from the group consisting of —H, and —$(C_1$-$C_6)$alkyl;
Q is selected from the group consisting of —H, —$(C_1$-$C_6)$ alkoxy, halogen, —$(C_1$-$C_6)$alkyl and —$NR^4{}_2$; and
$X^2$ is selected from the group consisting of —$NO_2$ and —$NH_2$, optionally protected with a chemical protecting group, or a salt of such a compound, to form an aniline, or a salt thereof; and (2) optionally alkylating the aniline with an alkylating reagent or by reductive amination,
to form said compound of formula IIIa; or a salt thereof.

43. A process according to claim 42 wherein the compound of formula IIa is prepared by condensing a compound of formula D:

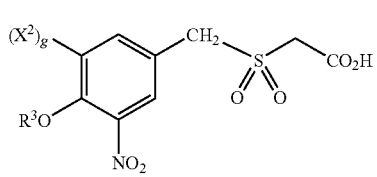

wherein:
each $R^3$ is independently selected from —$(C_1$-$C_6)$alkyl; and
g is 0 or 1; and
$X^2$ is selected from the group consisting of —$NO_2$ and —$NH_2$, optionally protected with a chemical protecting group;

with a compound of formula E:

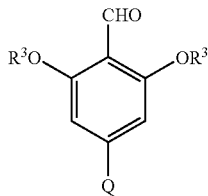

wherein:
each $R^3$ is independently selected from —$(C_1$-$C_6)$alkyl; and
each $R^4$ is independently selected from the group consisting of —H, and —$(C_1$-$C_6)$alkyl;
Q is selected from the group consisting of —H, —$(C_1$-$C_6)$ alkoxy, halogen, —$(C_1$-$C_6)$alkyl and —$NR^4{}_2$; and salts thereof;
to form said compound of formula IIa; or a salt of such a compound.

44. A process for producing a compound according to claim 9 having the formula IV

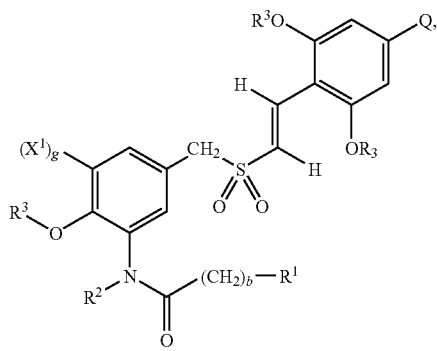

comprising,
(1) coupling a compound of formula IIIa:

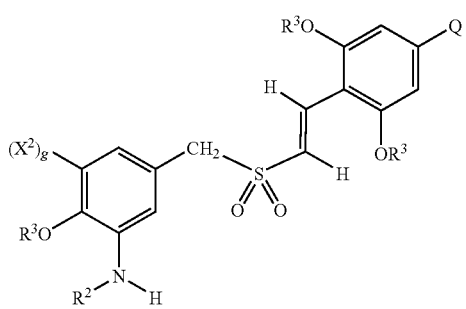

wherein:
g is 0 or 1; and
$X^2$ is selected from the group consisting of —$NO_2$ and —$NH_2$, optionally protected with a chemical protecting group; or a salt of such a compound;
with a compound of formula XII:

$$R^1\text{-}A^1 \qquad \text{XII}$$

wherein:
each $R^1$ is independently selected from the group consisting of unsubstituted aryl, substituted aryl, substituted heterocyclic, unsubstituted heterocyclic, —$CO_2R^5$, —$C(=O)NR^4{}_2$, —$CR^4R^6R^7$, —$C(=NH)$—$NR^4{}_2$, —$(C_1$-$C_6)$perfluoroalkyl, —$CF_2Cl$, —$P(=O)(OR^4)_2$, —OP(=O)(OR⁴)₂ and a monovalent peptidyl moiety with a molecular weight of less than 1000; provided that when y is 0 and R¹ is —CO₂R⁵, R⁵ is not —H;

each R⁴ is independently selected from the group consisting of —H, and —(C₁-C₆)alkyl;

each R⁵ is independently selected from the group consisting of —H, —(C₁-C₆)alkyl and —(C₁-C₆)acyl;

each R⁶ is independently selected from the group consisting of —(C₁-C₆)alkyl, —CO₂R⁵, —C(=O)R⁷, —OH, —SR⁴, —(C₁-C₃)alkoxy, —(C₁-C₃)alkylthio, guanidino, —NR⁴₂, phenyl, substituted phenyl, heterocyclic, substituted heterocyclic and halogen; and each R⁷ is independently selected from the group consisting of —H, halogen, —(C₁-C₆)alkyl, —NR⁴₂, and heterocycles containing two nitrogen atoms; and wherein the substituents for the substituted aryl and substituted heterocyclic groups comprising or included within R¹, R², Rᵃ, R⁶ and R⁷, are independently selected from the group consisting of halogen, (C₁-C₆)alkyl, —NO₂, —C≡N, —CO₂R⁵, —C(=O)O(C₁-C₃)alkyl, —OR⁵, —(C₂-C₆)alkylene-OH, phosphonato, —NR⁴₂, —NHC(=O)(C₁-C₆)alkyl, sulfamyl, —OC(=O)(C₁-C₃)alkyl, —O(C₂-C₆)alkylene-N((C₁-C₆)alkyl)₂ and —CF₃; and wherein one or more functional groups comprising R¹ are optionally protected by chemical protecting groups; and A¹ is a carboxylic acid moiety with a leaving group, to form a compound of formula IVa:

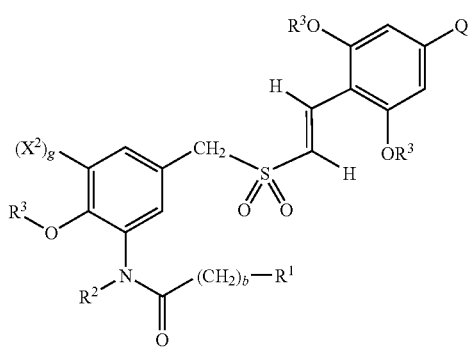

IVa (2) optionally:
(a) when —X² is —NH₂ protected with a protecting group, removing said protecting group from —X² to yield a compound of formula IVb; or
(b) when —X² is —NO₂, chemically reducing said —NO₂ to —NH₂
to form a compound of formula IVb:

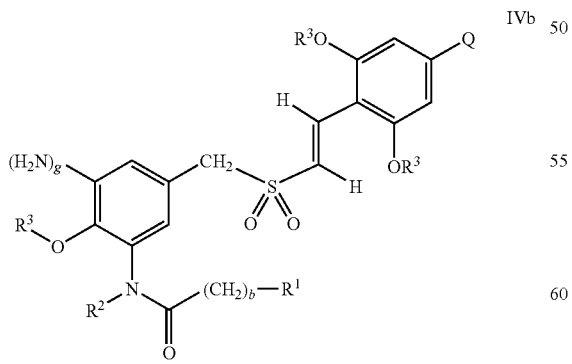

IVb (3) optionally coupling said compound of formula IVb or a salt thereof with a compound of formula XI:

R¹-A   XI wherein one or more functional groups comprising R¹ are optionally protected by chemical protecting groups; and wherein A is a moiety containing an electrophilic reactive center; and (4) optionally removing said protecting groups protecting functionalities comprising R¹ to form said compound of formula IV or a salt thereof.

45. The process according to claim 44 wherein in the structure of said compound of formula XII:

R¹ is selected from the group consisting of unsubstituted aryl, substituted aryl, substituted heterocyclic, unsubstituted heterocyclic, —CO₂R⁵, —C(=O)NR⁴₂, —CHR⁶R⁷, —C(=NH)—NR⁴₂ and a monovalent peptidyl moiety with a molecular weight of less than 1000;

each R⁴ is independently selected from the group consisting of —H, and —(C₁-C₆)alkyl;

each R⁵ is independently selected from the group consisting of —H, —(C₁-C₆)alkyl and —(C₁-C₆)acyl;

each R⁶ is independently selected from the group consisting of —(C₁-C₆)alkyl, —CO₂R⁵, —C(=O)R⁷, —OH, —SR⁴, —(C₁-C₃)alkoxy, —(C₁-C₃)alkylthio, guanidino, —NR⁴₂, phenyl, substituted phenyl, heterocyclic, substituted heterocyclic and halogen;

each R⁷ is independently selected from the group consisting of —H, halogen, —(C₁-C₆)alkyl, —NR⁴₂, and heterocycles containing two nitrogen atoms;

wherein the substituents for the substituted aryl and substituted heterocyclic groups comprising or included within R¹, R⁶ and R⁷, are independently selected from the group consisting of halogen, (C₁-C₆)alkyl, (C₁-C₆)alkoxy, —NO₂, —C≡N, —CO₂R⁵, —C(=O)O(C₁-C₃)alkyl, —OH, —(C₂-C₆)alkylene-OH, phosphonato, —NR⁴₂, —NHC(=O)(C₁-C₆)alkyl, sulfamyl, —OC(=O)(C₁-C₃)alkyl, —O(C₂-C₆)alkylene-N((C₁-C₆)alkyl)₂ and —CF₃; and wherein one or more functional groups comprising R¹ optionally protected by chemical protecting groups; and A¹ is a carboxylic acid moiety with a leaving group.

46. A process for producing a compound according to claim 13 having the formula V:

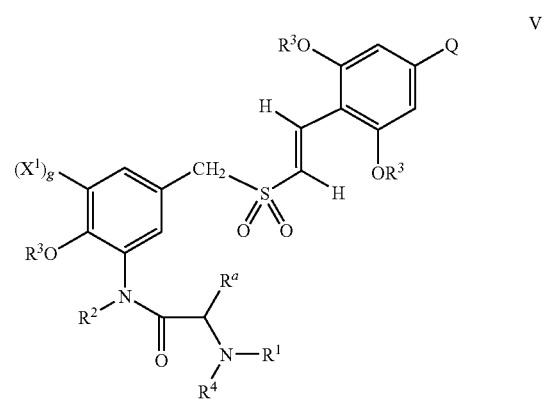

V comprising:
(1) reacting a compound of formula IIIa:

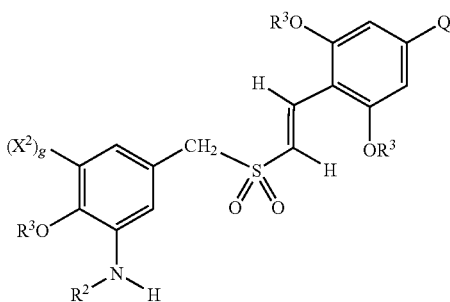

wherein:
g is 0 or 1;
and
$X^2$ is selected from the group consisting of —$NO_2$ and —$NH_2$, optionally protected with a chemical protecting group; or a salt of such a compound;
with
(a) a compound of formula XIII:

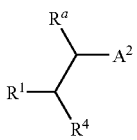

wherein:
each $R^a$ is independently selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;
each $R^1$ is independently selected from the group consisting of unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$, —($C_1$-$C_6$)perfluoroalkyl, —$CF_2$Cl, —P(=O)($OR^4$)$_2$, —OP(=O)($OR^4$)$_2$ and a monovalent peptidyl moiety with a molecular weight of less than 1000; provided that when y is 0 and $R^1$ is —$CO_2R^5$, $R^5$ is not —H;
each $R^4$ is independently selected from the group consisting of —H, and —($C_1$-$C_6$)alkyl;
each $R^5$ is independently selected from the group consisting of —H, —($C_1$-$C_6$)alkyl and —($C_1$-$C_6$)acyl;
each $R^6$ is independently selected from the group consisting of —($C_1$-$C_6$)alkyl, —$CO_2R^5$, —C(=O)$R^7$, —OH, —$SR^4$, —($C_1$-$C_3$)alkoxy, —($C_1$-$C_3$)alkylthio, guanidino, —$NR^4_2$, phenyl, substituted phenyl, heterocyclic, substituted heterocyclic and halogen; and
each $R^7$ is independently selected from the group consisting of —H, halogen, —($C_1$-$C_6$)alkyl, —$NR^4_2$, and heterocycles containing two nitrogen atoms; and
wherein the substituents for the substituted aryl and substituted heterocyclic groups comprising or included within $R^1$, $R^2$, $R^a$, $R^6$ and $R^7$, are independently selected from the group consisting of halogen, ($C_1$-$C_6$)alkyl, —$NO_2$, —C≡N, —$CO_2R^5$, —C(=O)O($C_1$-$C_3$)alkyl, —$OR^5$, —($C_2$-$C_6$)alkylene-OH, phosphonato, —$NR^4_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$; and wherein one or more functional groups comprising $R^1$ are optionally protected by chemical protecting groups; and $A^2$ comprises an electrophilic moiety; and
(b) an amide coupling reagent;
to form a compound of formula Va:

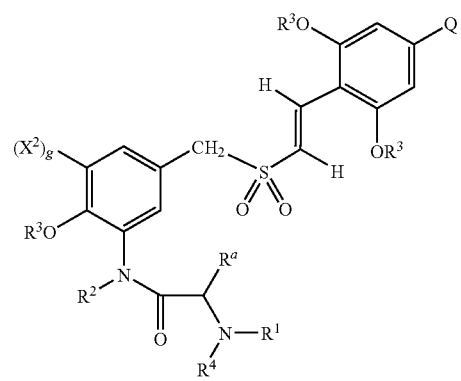

(2) optionally:
(a) when —$X^2$ is —$NH_2$ protected with a protecting group, removing said protecting group from —$X^2$ to yield a compound of formula Vb; or
(b) when —$X^2$ is —$NO_2$, chemically reducing said —$NO_2$ to —$NH_2$,
to form a compound of formula Vb:

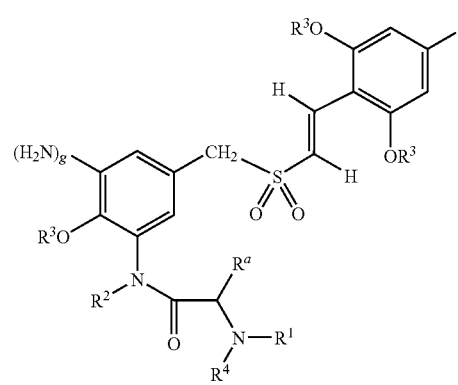

(3) optionally coupling said compound of formula Vb or a salt thereof:
with a compound of formula XI:

$$R^1\text{-A} \qquad \qquad \text{XI}$$

wherein one or more functional groups comprising $R^1$ are optionally protected by chemical protecting groups; and
wherein A is a moiety containing an electrophilic reactive center; and
(4) optionally removing said protecting groups protecting functionalities comprising $R^1$ to form said compound of formula V; or a salt thereof.

47. The process of claim 46 wherein in the structure of said compound of formula XIII:
$R^a$ is selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —CH$_2$-(4-hydroxyphenyl), —CH(CH$_3$)$_2$ and —CH$_2$—CH$_3$; and includes compounds wherein R$^a$ and R$^1$ combine to form a 5-, 6- or 7-membered heterocyclic ring;

R$^1$ is selected from the group consisting of unsubstituted aryl, substituted aryl, substituted heterocyclic, unsubstituted heterocyclic, —CO$_2$R$^5$, —C(═O)NR$^4$$_2$, —CHR$^6$R$^7$, —C(═NH)—NR$^4$$_2$ and a monovalent peptidyl moiety with a molecular weight of less than 1000 and coupled through the carboxy terminus of the peptidyl moiety or through a sidechain carboxyl group to form a carboxamide bond;

each R$^4$ is independently selected from the group consisting of —H, and —(C$_1$-C$_6$)alkyl;

R$^5$ is selected from the group consisting of —H, —(C$_1$-C$_6$)alkyl and —(C$_1$-C$_6$)acyl;

each R$^6$ is independently selected from the group consisting of —(C$_1$-C$_6$)alkyl, —CO$_2$R$^5$, —C(═O)R$^7$, —OH, —SR$^4$, —(C$_1$-C$_3$)alkoxy, —(C$_1$-C$_3$)alkylthio, guanidino, —NR$^4$$_2$, phenyl, substituted phenyl, heterocyclic, substituted heterocyclic and halogen;

each R$^7$ is independently selected from the group consisting of —H, halogen, —(C$_1$-C$_6$)alkyl, —NR$^4$$_2$, and heterocycles containing two nitrogen atoms;

wherein the substituents for the substituted aryl and substituted heterocyclic groups comprising or included within R$^1$, R$^a$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(═O)O(C$_1$-C$_3$)alkyl, —OH, —(C$_2$-C$_6$)alkylene-OH, phosphonato, —NR$^4$$_2$, —NHC(═O)(C$_1$-C$_6$)alkyl, sulfamyl, —OC(═O)(C$_1$-C$_3$)alkyl, —O(C$_2$-C$_6$)alkylene-N((C$_1$-C$_6$)alkyl)$_2$ and —CF$_3$; and wherein one or more functional groups comprising R$^1$ are optionally protected by chemical protecting groups.

48. A process for producing a compound according to claim 16 having the formula VI:

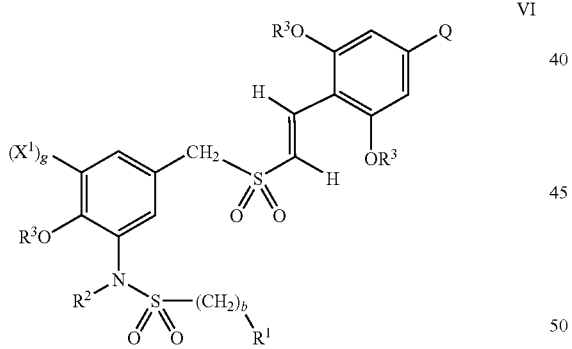

VI comprising, (1) coupling a compound of formula IIIa:

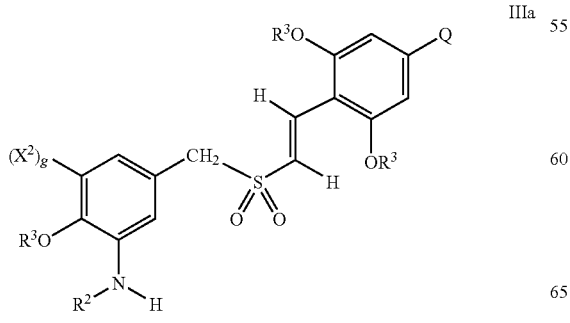

IIIa wherein:

g is 0 or 1; and

X$^2$ is selected from the group consisting of —NO$_2$ and —NH$_2$, optionally protected with a chemical protecting group; or a salt of such a compound;

with a compound of formula XIV:

$$R^1\text{-}A^3 \qquad \text{XIV}$$

wherein:

each R$^1$ is independently selected from the group consisting of unsubstituted aryl, substituted aryl, substituted heterocyclic, unsubstituted heterocyclic, —CO$_2$R$^5$, —C(═O)NR$^4$$_2$, —CR$^4$R$^6$R$^7$, —C(═NH)—NR$^4$$_2$, —(C$_1$-C$_6$)perfluoroalkyl, —CF$_2$Cl, —P(═O)(OR$^4$)$_2$, —OP(═O)(OR$^4$)$_2$ and a monovalent peptidyl moiety with a molecular weight of less than 1000; provided that when y is 0 and R$^1$ is —CO$_2$R$^5$, R$^5$ is not —H;

each R$^4$ is independently selected from the group consisting of —H, and —(C$_1$-C$_6$)alkyl;

each R$^5$ is independently selected from the group consisting of —H, —(C$_1$-C$_6$)alkyl and —(C$_1$-C$_6$)acyl;

each R$^6$ is independently selected from the group consisting of —(C$_1$-C$_6$)alkyl, —CO$_2$R$^5$, —C(═O)R$^7$, —OH, —SR$^4$, —(C$_1$-C$_3$)alkoxy, —(C$_1$-C$_3$)alkylthio, guanidino, —NR$^4$$_2$, phenyl, substituted phenyl, heterocyclic, substituted heterocyclic and halogen; and each R$^7$ is independently selected from the group consisting of —H, halogen, —(C$_1$-C$_6$)alkyl, —NR$^4$$_2$, and heterocycles containing two nitrogen atoms; and wherein the substituents for the substituted aryl and substituted heterocyclic groups comprising or included within R$^1$, R$^2$, R$^a$, R$^6$ and R$^7$, are independently selected from the group consisting of halogen, (C$_1$-C$_6$)alkyl, —NO$_2$, —C≡N, —CO$_2$R$^5$, —C(═O)O(C$_1$-C$_3$)alkyl, —OR$^5$, —(C$_2$-C$_6$)alkylene-OH, phosphonato, —NR$^4$$_2$, —NHC(═O)(C$_1$-C$_6$)alkyl, sulfamyl, —OC(═O)(C$_1$-C$_3$)alkyl, —O(C$_2$-C$_6$)alkylene-N((C$_1$-C$_6$)alkyl)$_2$ and —CF$_3$; and wherein one or more functional groups comprising R$^1$ are optionally protected by chemical protecting groups; and A$^3$ is a sulfonyl chloride moiety;

to form a compound of formula VIa:

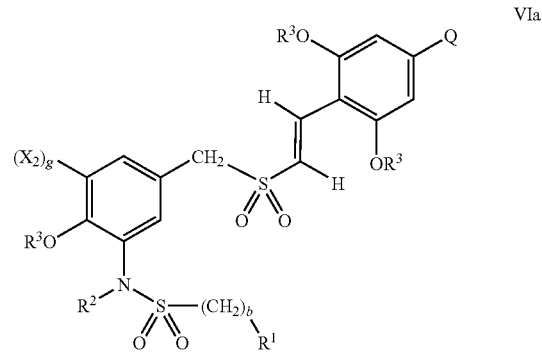

VIa (2) optionally:

(a) when —X$^2$ is —NH$_2$ protected with a protecting group, removing said protecting group from —X$^2$ to yield a compound of formula VIb; or (b) when —X$^2$ is —NO$_2$, chemically reducing said —NO$_2$ to —NH$_2$, to form a compound of formula VIb:

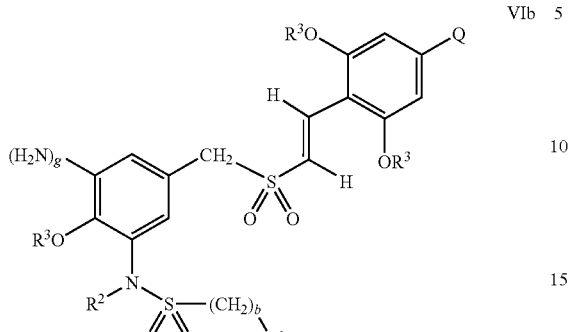

(3) optionally coupling said compound of formula VIb or a salt thereof:

with a compound of formula XI:

R¹-A  XI wherein one or more functional groups comprising $R^1$ are optionally protected by chemical protecting groups; and wherein A is a moiety containing an electrophilic reactive center; and (4) optionally removing said protecting groups protecting functionalities comprising $R^1$ to form said compound of formula VI.

49. The process of claim 48 wherein in the structure of said compound of formula XIV:

$R^1$ is selected from the group consisting of unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000;

each $R^4$ is independently selected from the group consisting of —H, and —($C_1$-$C_6$) alkyl;

each $R^5$ is independently selected from the group consisting of —H, —($C_1$-$C_6$)alkyl and —($C_1$-$C_6$)acyl;

each $R^6$ is independently selected from the group consisting of —($C_1$-$C_6$)alkyl, —$CO_2R^5$, —C(=O)$R^7$, —OH, —$SR^4$, —($C_1$-$C_3$)alkoxy, —($C_1$-$C_3$)alkylthio, guanidino, —$NR^4_2$, phenyl, substituted phenyl, heterocyclic, substituted heterocyclic and halogen;

each $R^7$ is independently selected from the group consisting of —H, halogen, —($C_1$-$C_6$)alkyl, —$NR^4_2$, and heterocycles containing two nitrogen atoms;

wherein the substituents for the substituted aryl and substituted heterocyclic groups comprising or included within $R^1$, $R^6$ and $R^7$, are independently selected from the group consisting of halogen, ($C_1$-$C_6$)alkyl, ($C_1$-$C_6$) alkoxy, —$NO_2$, —C≡N, —$CO_2R^5$, —C(=O)O($C_1$-$C_3$)alkyl, —OH, —($C_2$-$C_6$)alkylene-OH, phosphonato, —$NR^4_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$) alkyl)$_2$ and —$CF_3$; and wherein one or more functional groups comprising $R^1$ are optionally protected by chemical protecting groups; and $A^3$ is a sulfonyl chloride moiety.

50. A process for producing a compound according to claim 20 having the formula VII:

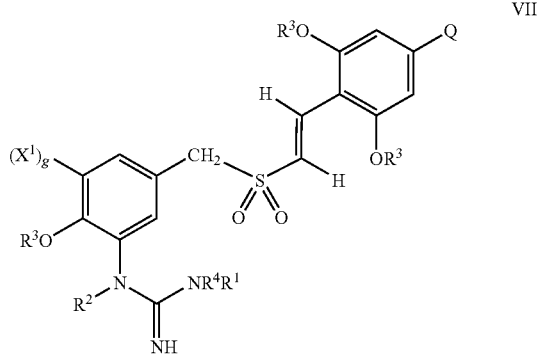

comprising, (1) coupling a compound of formula IIIa:

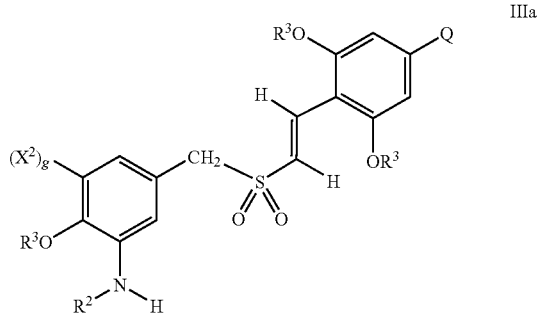

wherein:
g is 0 or 1;
and
$X^2$ is selected from the group consisting of —$NO_2$ and —$NH_2$, optionally protected with a chemical protecting group; or a salt of such a compound;

with a compound of formula XV:

R¹-A⁴  XV wherein one or more functional groups comprising $R^1$ are optionally protected by chemical protecting groups; and wherein $A^4$ is a moiety which is a reactive intermediate product of a substituted thiourea and 2-chloro-1-methyl pyridinium iodide;

to form a compound of formula VIIa:

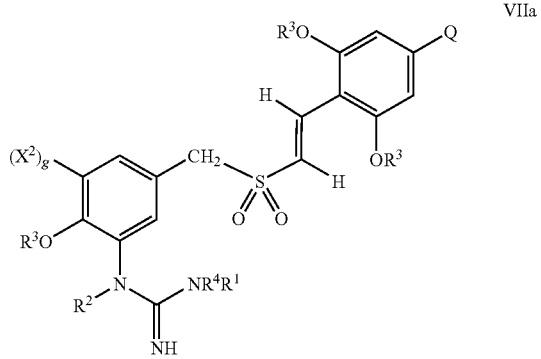

(2) optionally:

(a) when —$X^2$ is —$NH_2$ protected with a protecting group, removing said protecting group from —$X^2$ to yield a compound of formula VIIb; or (b) when —$X^2$ is —$NO_2$, chemically reducing said —$NO_2$ to —$NH_2$, to form a compound of formula VIIb:

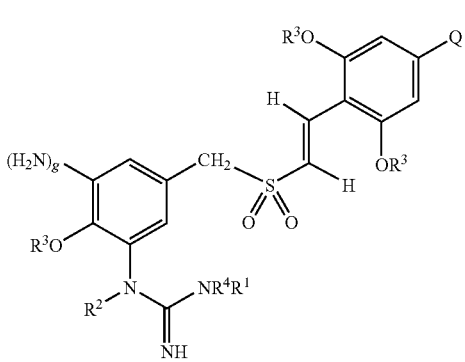

(3) optionally coupling said compound of formula VIIb or a salt thereof:
with a compound of formula XI:

R$^1$-A                                    XI wherein one or more functional groups comprising R$^1$ are optionally protected by chemical protecting groups; and
wherein A is a moiety containing an electrophilic reactive center; and (4) optionally removing said protecting groups protecting functionalities comprising R$^1$ to form said compound of formula VII; or a salt thereof.

51. A process for producing a compound according to claim 24 having the formula VIII:

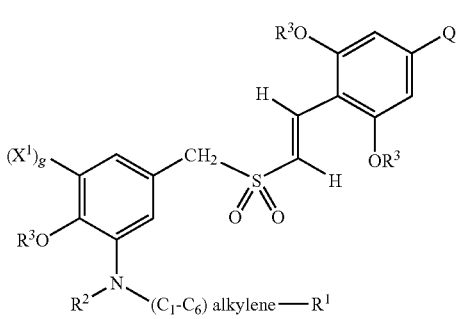

comprising:
(1) coupling a compound of formula IIIa:

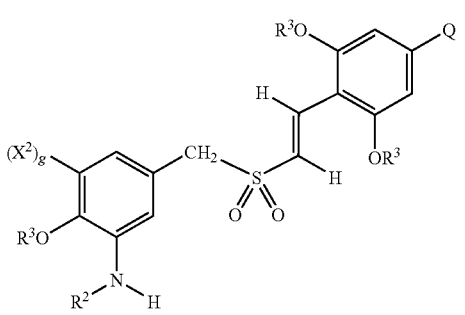

wherein:
g is 0 or 1;
and
X$^2$ is selected from the group consisting of NO$_2$ and —NH$_2$, optionally protected with a chemical protecting group; or a salt of such a compound;
with a compound of formula XVI:

R$^1$-A$^5$                                 XVI wherein:
each R$^1$ is selected from the group consisting of unsubstituted aryl, substituted aryl, substituted heterocyclic, unsubstituted heterocyclic, —CO$_2$R$^5$, —C(=O)NR$^4{}_2$, —CHR$^6$R$^7$, —C(=NH)—NR$^4{}_2$ and a monovalent peptidyl moiety with a molecular weight of less than 1000;
each R$^4$ is independently selected from the group consisting of —H, and —(C$_1$-C$_6$)alkyl;
each R$^5$ is independently selected from the group consisting of —H, —(C$_1$-C$_6$)alkyl and —(C$_1$-C$_6$)acyl;
each R$^6$ is independently selected from the group consisting of —(C$_1$-C$_6$)alkyl, —CO$_2$R$^5$, —C(=O)R$^7$, —OH, —SR$^4$, —(C$_1$-C$_3$)alkoxy, —(C$_1$-C$_3$)alkylthio, guanidino, —NR$^4{}_2$, phenyl, substituted phenyl, heterocyclic, substituted heterocyclic and halogen;
each R$^7$ is independently selected from the group consisting of —H, halogen, —(C$_1$-C$_6$)alkyl, —NR$^4{}_2$, and heterocycles containing two nitrogen atoms;
wherein the substituents for the substituted aryl and substituted heterocyclic groups comprising or included within R$^1$, R$^6$ and R$^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4{}_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$; and wherein one or more functional groups comprising R$^1$ are optionally protected by chemical protecting groups; and
wherein A$^5$ is an alkyl moiety with a leaving group;
to form a compound of formula VIIIa:

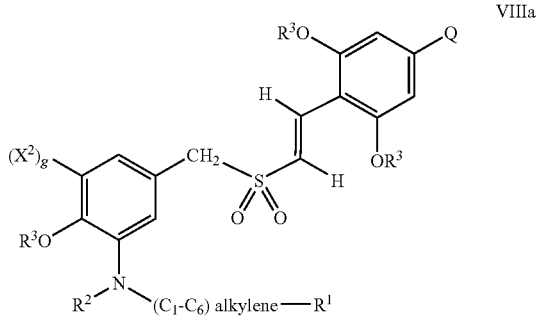

(2) optionally:
(a) when —X$^2$ is —NH$_2$ protected with a protecting group, removing said protecting group from —X$^2$ to yield a compound of formula VIIIb; or
(b) when —X$^2$ is —NO$_2$, chemically reducing said —NO$_2$ to —NH$_2$, to form a compound of formula VIIIb:

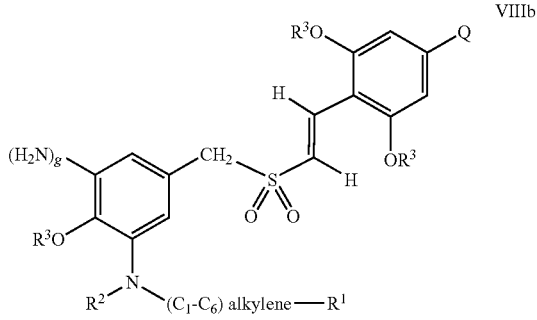

(3) optionally coupling said compound of formula VIIIb or a salt thereof: with a compound of formula XI:

R$^1$-A                                    XI wherein one or more functional groups comprising R$^1$ are optionally protected by chemical protecting groups; and
wherein A is a moiety containing an electrophilic reactive center; and (4) optionally removing said protecting groups protecting functionalities comprising $R^1$ to form said compound of formula VIII; or a salt thereof.

52. A process for producing a compound according to claim 26 having the formula IX:

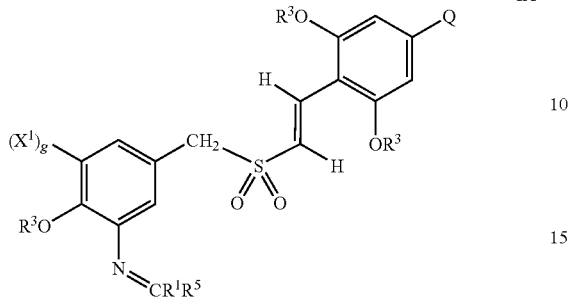

IX comprising;
(1) coupling a compound of formula IIIa:

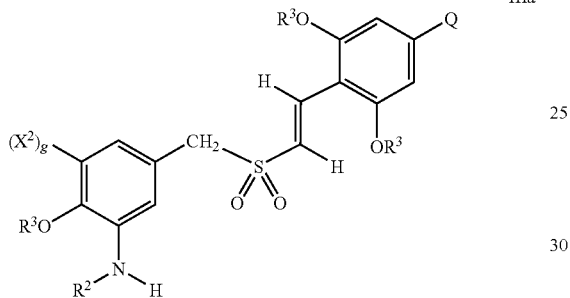

IIIa wherein:
g is 0 or 1; and
$X^2$ is selected from the group consisting of $-NO_2$ and $-NH_2$, optionally protected with a chemical protecting group; or a salt of such a compound;
with a compound of formula XVII:

$R^1-A^6$ XVII wherein:
each $R^1$ is selected from the group consisting of unsubstituted aryl, substituted aryl, substituted heterocyclic, unsubstituted heterocyclic, $-CO_2R^5$, $-C(=O)NR^4_2$, $-CHR^6R^7$, $-C(=NH)-NR^4_2$ and a monovalent peptidyl moiety with a molecular weight of less than 1000;
each $R^4$ is independently selected from the group consisting of $-H$, and $-(C_1-C_6)$alkyl;
each $R^5$ is independently selected from the group consisting of $-H$, $-(C_1-C_6)$alkyl and $-(C_1-C_6)$acyl;
each $R^6$ is independently selected from the group consisting of $-(C_1-C_6)$alkyl, $-CO_2R^5$, $-C(=O)R^7$, $-OH$, $-SR^4$, $-(C_1-C_3)$alkoxy, $-(C_1-C_3)$alkylthio, guanidino, $-NR^4_2$, phenyl, substituted phenyl, heterocyclic, substituted heterocyclic and halogen;
each $R^7$ is independently selected from the group consisting of $-H$, halogen, $-(C_1-C_6)$alkyl, $-NR^4_2$, and heterocycles containing two nitrogen atoms;
wherein the substituents for the substituted aryl and substituted heterocyclic groups comprising or included within $R^1$, $R^6$ and $R^7$, are independently selected from the group consisting of halogen, $(C_1-C_6)$alkyl, $(C_1-C_6)$alkoxy, $-NO_2$, $-C\equiv N$, $-CO_2R^5$, $-C(=O)O(C_1-C_3)$alkyl, $-OH$, $-(C_2-C_6)$alkylene-OH, phosphonato, $-NR^4_2$, $-NHC(=O)(C_1-C_6)$alkyl, sulfamyl, $-OC(=O)(C_1-C_3)$alkyl, $-O(C_2-C_6)$alkylene-N$((C_1-C_6)$alkyl$)_2$ and $-CF_3$; and wherein one or more functional groups comprising $R^1$ are optionally protected by chemical protecting groups; and
wherein $A^6$ comprises an aldehyde or ketone moiety, or a hydrate thereof or a ketal or acetal thereof;
to form a compound of formula IXa:

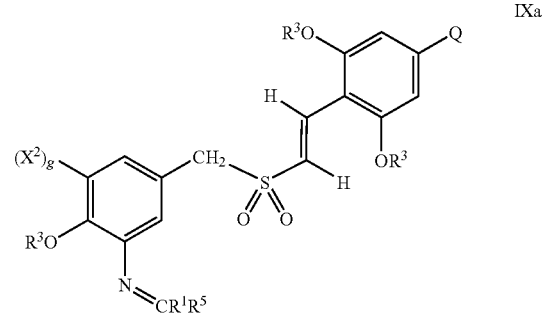

IXa (2) optionally:
(a) when $-X^2$ is $-NH_2$ protected with a protecting group, removing said protecting group from $-X^2$ to yield a compound of formula IXb; or
(b) when $-X^2$ is $-NO_2$, chemically reducing said $-NO_2$ to $-NH_2$, to form a compound of formula IXb:

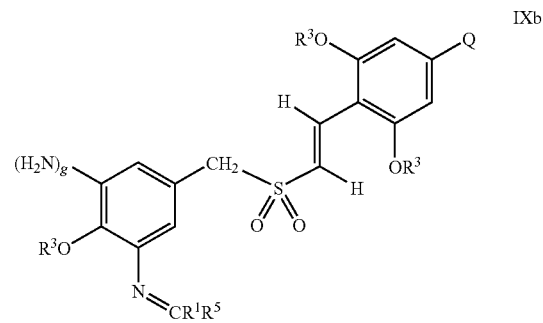

IXb (3) optionally coupling said compound of formula IXb or a salt thereof: with a compound of formula XI:

$R^1-A$ XI wherein one or more functional groups comprising $R^1$ are optionally protected by chemical protecting groups; and
wherein A is a moiety containing an electrophilic reactive center; and
(4) optionally removing said protecting groups protecting functionalities comprising $R^1$ to form said compound of formula IX; or a salt thereof.

53. A process for producing a compound according to claim 30 having the formula X:

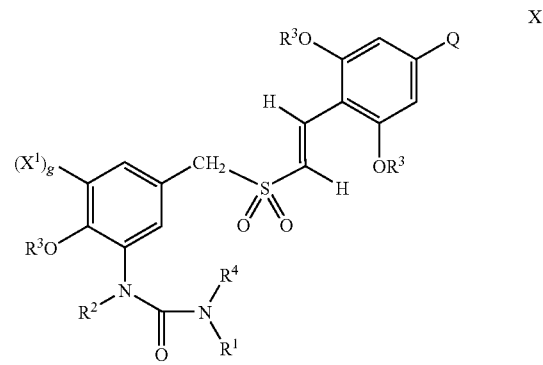

X comprising;

(1) coupling a compound of formula IIIa:

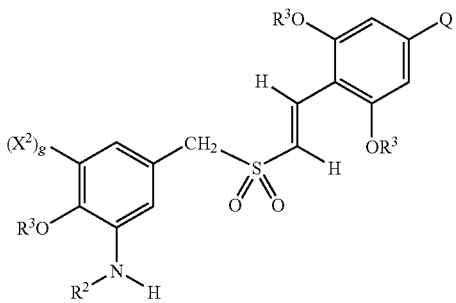

wherein:
g is 0 or 1;
and
$X^2$ is selected from the group consisting of $-NO_2$ and $-NH_2$, optionally protected with a chemical protecting group; or a salt of such a compound;
with a compound of formula XVIII:

$$R^1-A^7 \qquad \text{XVIII}$$

wherein:
each $R^1$ is selected from the group consisting of unsubstituted aryl, substituted aryl, substituted heterocyclic, unsubstituted heterocyclic, $-CO_2R^5$, $-C(=O)NR^4_2$, $-CHR^6R^7$, $-C(=NH)-NR^4_2$ and a monovalent peptidyl moiety with a molecular weight of less than 1000;
each $R^4$ is independently selected from the group consisting of $-H$, and $-(C_1-C_6)$alkyl;
each $R^5$ is independently selected from the group consisting of $-H$, $-(C_1-C_6)$alkyl and $-(C_1-C_6)$acyl;
each $R^6$ is independently selected from the group consisting of $-(C_1-C_6)$alkyl, $-CO_2R^5$, $-C(=O)R^7$, $-OH$, $-SR^4$, $-(C_1-C_3)$alkoxy, $-(C_1-C_3)$alkylthio, guanidino, $-NR^4_2$, phenyl, substituted phenyl, heterocyclic, substituted heterocyclic and halogen;
each $R^7$ is independently selected from the group consisting of $-H$, halogen, $-(C_1-C_6)$alkyl, $-NR^4_2$, and heterocycles containing two nitrogen atoms;
wherein the substituents for the substituted aryl and substituted heterocyclic groups comprising or included within $R^1$, $R^6$ and $R^7$, are independently selected from the group consisting of halogen, $(C_1-C_6)$alkyl, $(C_1-C_6)$alkoxy, $-NO_2$, $-C\equiv N$, $-CO_2R^5$, $-C(=O)O(C_1-C_3)$alkyl, $-OH$, $-(C_2-C_6)$alkylene-OH, phosphonato, $-NR^4_2$, $-NHC(=O)(C_1-C_6)$alkyl, sulfamyl, $-OC(=O)(C_1-C_3)$alkyl, $-O(C_2-C_6)$alkylene-N$((C_1-C_6)$alkyl$)_2$ and $CF_3$; and wherein one or more functional groups comprising $R^1$ are optionally protected by chemical protecting groups; and
wherein:
(a) if $A^7$ is a cyanate moiety, then
$R^1$ is selected from the group consisting of $-H$, $(C_1-C_6)$alkyl and aryl; and and $R^4$ is $-H$; and
(b) if $A^7$ is a carbamic acid moiety activated with a leaving group, then $R^1$ and $R^4$ of formula X are as defined above;

to form a compound of formula Xa:

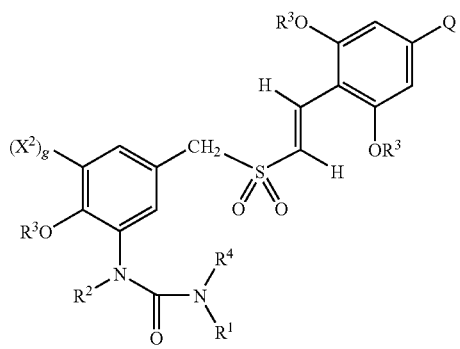

(2) optionally:
(a) when $-X^2$ is $-NH_2$ protected with a protecting group, removing said protecting group from $-X^2$ to yield a compound of formula Xb; or
(b) when $-X^2$ is $-NO_2$, chemically reducing said $-NO_2$ to $-NH_2$;
to form a compound of formula Xb:

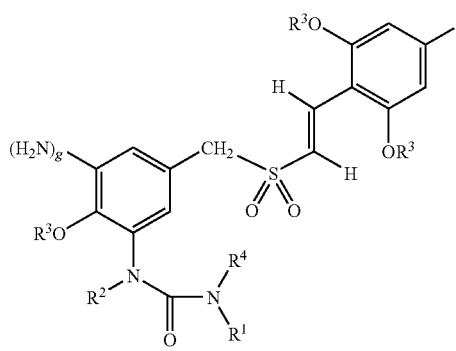

(3) optionally coupling said compound of formula Xb or a salt thereof: with a compound of formula XI:

$$R^1-A \qquad \text{XI}$$

wherein one or more functional groups comprising $R^1$ are optionally protected by chemical protecting groups; and
wherein A is a moiety containing an electrophilic reactive center; and
(4) optionally removing said protecting groups protecting functionalities comprising $R^1$ to form said compound of formula X; or a salt thereof.

54. A process for producing a compound according to claim 33 having the formula XX as a carboxylic acid salt

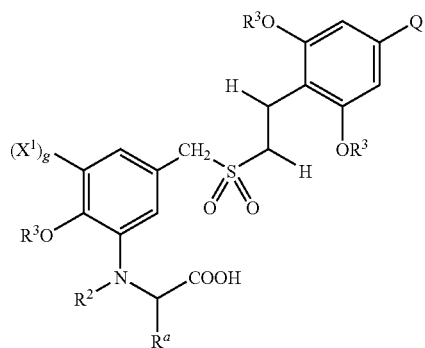

comprising:
(1) coupling a compound of formula IIIa:

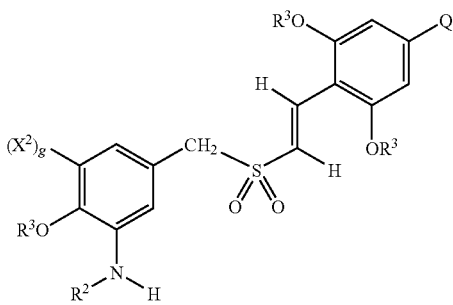

wherein:
g is 0 or 1; and
$X^2$ is selected from the group consisting of —$NO_2$ and —$NH_2$, optionally protected with a chemical protecting group; or a salt of such a compound; with a compound of formula XIX:

$R^1$-$A^8$    XIX wherein:
$R^1$ is —$CHR^6R^7$;
$R^6$ is —$CO_2(C_1-C_6)$alkyl;
$R^7$ is $R^a$; and
$A^8$ is a leaving group;
wherein one or more functional groups comprising $R^1$ are optionally protected by chemical protecting groups;
to form a compound of formula XXa:

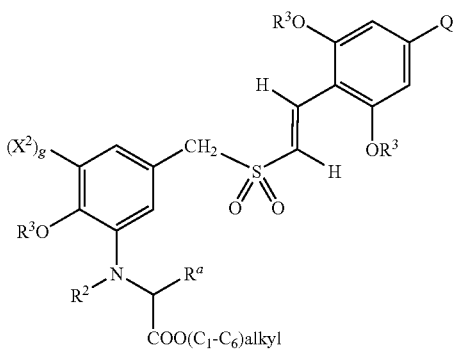

(2) optionally:
(a) when —$X^2$ is —$NH_2$ protected with a protecting group, removing said protecting group from —$X^2$ to yield a compound of formula XXb; or
(b) when —$X^2$ is —$NO_2$, chemically reducing said —$NO_2$ to —$NH_2$;
to form a compound of formula XXb:

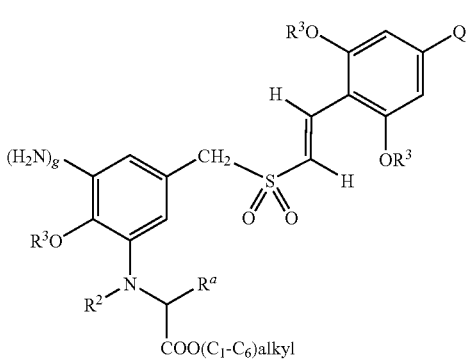

(3) optionally coupling said compound of formula XXb or a salt thereof; with a compound of formula XI:

$R^1$-A    XI wherein one or more functional groups comprising $R^1$ are optionally protected by chemical protecting groups; and
wherein A is a moiety containing an electrophilic reactive center; and
(4) optionally removing said protecting groups protecting functionalities comprising $R^1$ to form said compound of formula XXc;

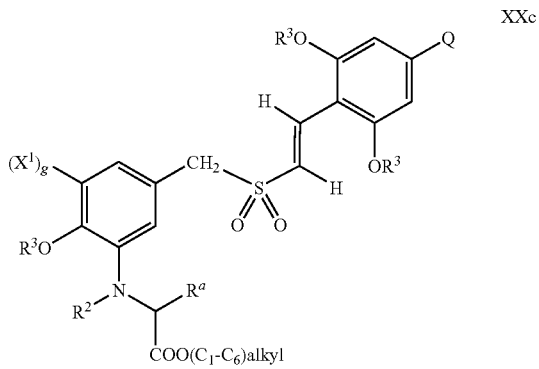

(5) reacting XXa, or optionally XXc, with an aqueous base to yield the compound according to claim 33 of formula XX as the carboxylic acid salt.

55. The method of claim 54 wherein the aqueous base of step 5 is sodium hydroxide and the product is a sodium salt of the compound of formula XX.

56. A conjugate of the formula, I-L-Ab; wherein I is a compound according to claim 1; Ab is an antibody; and -L- is a single covalent bond or a linking group covalently linking said compound to said antibody.

57. A conjugate of the formula, I-L-Ab; wherein I is a compound according to claim 5; Ab is an antibody; and -L- is a single covalent bond or a linking group covalently linking said compound to said antibody.

58. A conjugate according to claim 56 or 57 wherein said antibody Ab is a monoclonal antibody or a monospecific polyclonal antibody.

59. A conjugate according to claim 58 wherein said antibody Ab is a tumor-specific antibody.

60. A pharmaceutical composition comprising a pharmaceutically acceptable carrier and at least one compound according to claim 1, or a pharmaceutically acceptable salt of such a compound.

61. A pharmaceutical composition comprising a pharmaceutically acceptable carrier and at least one compound according to claim 5, or a pharmaceutically acceptable salt of such a compound.

62. A pharmaceutical composition comprising a pharmaceutically acceptable carrier and at least one conjugate according to claim 56 or claim 57.

63. A pharmaceutical composition comprising a pharmaceutically acceptable carrier and at least one conjugate according to claim 58.

64. A method of treating an individual for a cancer selected from the group consisting of breast, prostate, lung and colorectal cancers comprising administering to said individual in need of such treatment an effective amount of at least one compound according to claim 1, or a pharmaceutically acceptable salt of such a compound.

65. A method of inducing apoptosis of tumor cells in an individual afflicted with a cancer selected from the group consisting of breast, prostate, lung and colorectal cancers, comprising administering to said individual an effective amount of at least one compound according to claim 1, or a pharmaceutically acceptable salt of such a compound.

66. A method of inducing apoptosis of tumor cells in an individual afflicted with a cancer selected from the group consisting of breast, prostate, lung and colorectal cancers, comprising administering to said individual an effective amount of at least one compound according to claim 5, or a pharmaceutically acceptable salt of such a compound.

67. A method of treating an individual afflicted with a cancer selected from the group consisting of breast, prostate, lung and colorectal cancers, comprising administering to said individual an effective amount of at least one conjugate according to any one of claims 56 or 57.

68. A compound according to claim 34 which is (E)-2,4,6-trimethoxystyryl-3-(carboxymethylamino)-4-methoxybenzylsulfone or a salt thereof.

69. A compound according to claim 68 which is (E)-2,4,6-trimethoxystyryl-3-(carboxymethylamino)-4-methoxybenzylsulfone sodium salt.

70. A pharmaceutical composition according to claim 60 comprising (E)-2,4,6-trimethoxystyryl-3-(carboxymethylamino)-4-methoxybenzylsulfone or a pharmaceutically acceptable salt thereof.

71. A method according to claim 64 comprising administering to the individual an effective amount of (E)-2,4,6-trimethoxystyryl-3-(carboxymethylamino)-4-methoxybenzylsulfone or a pharmaceutically acceptable salt thereof.

72. A compound according to claim 1 wherein:
X is

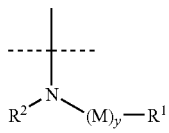

(i)

y is 0; $R^1$ is —$CR^4R^6R^7$; $R^4$ is —$(C_1$-$C_6)$alkyl, $R^6$ is $CO_2R^5$ and $R^7$ is $R^a$; and g is 0; or a salt of such a compound.

73. A compound according to claim 72 wherein $R^5$ is hydrogen; or a salt of such a compound.

74. A compound according to claim 73 selected from the group consisting of sodium and potassium salts.

75. A compound according to claim 74 wherein the compound is a sodium salt.

76. A compound according to claim 73 wherein said compound is (E)-2,4,6-trimethoxystyryl-3-(2-carboxy-2-propyl)amino-4-methoxybenzylsulfone; or a salt of such a compound.

77. A compound according to claim 76 wherein the compound is a sodium salt.

78. A process according to claim 41, wherein the compound of formula IIIa is (E)-2,4,6-trimethoxystyryl-4-methoxy-3-aminobenzylsulfone, or a salt thereof.

79. A process according to claim 42, wherein the compound of formula IIIa is (E)-2,4,6-trimethoxystyryl-4-methoxy-3-aminobenzylsulfone, or a salt thereof.

80. A compound of formula I:

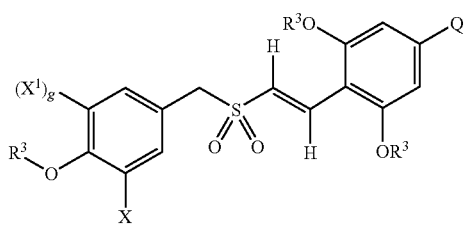

I wherein:
X is selected from the group consisting of (i) and (ii) below:

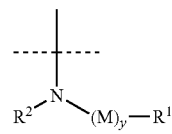

(i)

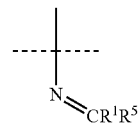

(ii)

$X^1$ is selected from the group consisting of (i), (ii) and (iii) below:

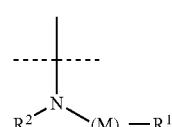

(i)

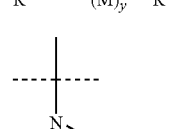

(ii)

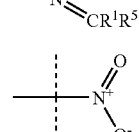

(iii)

g is 0 or 1;
each M is a bivalent connecting group independently selected from the group consisting of —$(CH_2)_a$—V—$(CH_2)_b$—, —$(CH_2)_d$—W—$(CH_2)_e$— and -Z-;
each y is 1;
each V is independently selected from the group consisting of arylene, heteroarylene, —C(=O)—, —C(=S)—, —S(=O)—, —$SO_2$—, —C(=O)O—; —C(=O)($C_1$-$C_6$)perfluoroalkylene-, —C(=O)$NR^4$—, —C(=S)$NR^4$— and —$SO_2NR^4$—;
each W is independently selected from the group consisting of —$NR^4$—, —O— and —S—;
each a is independently selected from the group consisting of 0, 1, 2 and 3;
each b is independently selected from the group consisting of 0, 1, 2 and 3;
each d is independently selected from the group consisting of 1, 2 and 3;
each e is independently selected from the group consisting of 0, 1, 2 and 3;

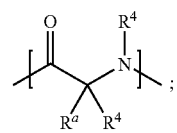

wherein the absolute stereochemistry of -Z- is D or L or a mixture of D and L;
each $R^a$ is independently selected from the group consisting of —H, —$(C_1$-$C_6)$alkyl, —$(CH_2)_3$—NH—C($NH_2$)(=NH), —$CH_2C$(=O)$NH_2$, —$CH_2COOH$, —$CH_2SH$, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$;

each R$^1$ is —H;

each R$^2$ is independently selected from the group consisting of —H, —(C$_1$-C$_6$)alkyl, and aryl(C$_1$-C$_3$)alkyl, wherein —R$^2$ and -(M)$_y$-R$^1$ may optionally be linked covalently to form a 5-, 6- or 7-membered substituted or unsubstituted heterocycle;

each R$^3$ is independently selected from —(C$_1$-C$_6$)alkyl;

each R$^4$ is independently selected from the group consisting of —H, and —(C$_1$-C$_6$)alkyl;

each R$^5$ is independently selected from the group consisting of —H, —(C$_1$-C$_6$)alkyl and —(C$_1$-C$_6$)acyl; and Q is selected from the group consisting of —H, —(C$_1$-C$_6$)alkoxy, halogen, —(C$_1$-C$_6$)alkyl and NR$^4_2$;

wherein the substituents for the substituted aryl and substituted heterocyclic groups comprising or included within R$^2$ and R$^a$ are independently selected from the group consisting of halogen, (C$_1$-C$_6$)alkyl, —NO$_2$, —C≡N, —CO$_2$R$^5$, —C(=O)O(C$_1$-C$_3$)alkyl, —OR$^5$, —(C$_2$-C$_6$)alkylene-OH, phosphonato, —NR$^4_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

81. A compound according to claim 80 wherein:
each V is independently selected from the group consisting of

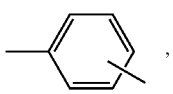,

—C(=O)—, —C(=S)—, —S(=O)—, —SO$_2$—, —C(=O)O—; —C(=O)(C$_1$-C$_6$)perfluoroalkylene-, —C(=O)NR$^4$—, —C(=S)NR$^4$— and —SO$_2$NR$^4$—;

or a salt of such a compound.

82. A compound according to claim 80 wherein:
each V is independently selected from the group consisting of

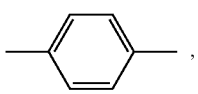,

—C(=O)—, —C(=S)—, —S(=O)—, —SO$_2$—, —C(=O)O—; —C(=O)(C$_1$-C$_6$)perfluoroalkylene-, —C(=O)NR$^4$—, —C(=S)NR$^4$— and —SO$_2$NR$^4$—;

or a salt of such a compound.

83. A compound according to claim 80 wherein:
each V is independently selected from the group consisting of —C(=O)—, —C(=S)—, —S(=O)—, —SO$_2$—; —C(=O)NR$^4$—, —C(=S)NR$^4$— and —SO$_2$NR$^4$—;

-Z- is

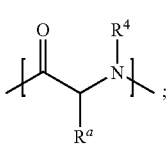

wherein the absolute stereochemistry of -Z- is either D or L;

each R$^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and each R$^1$ is —H;

wherein the substituents for the substituted aryl and substituted heterocyclic groups comprising or included within R$^a$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

84. A compound according to claim 83, wherein:
X is

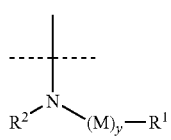

y is 1;
M is —(CH$_2$)$_a$—V—(CH$_2$)$_b$—;
V is —C(=O)—;

or a salt of such a compound.

85. A compound according to claim 84, having the formula IV:

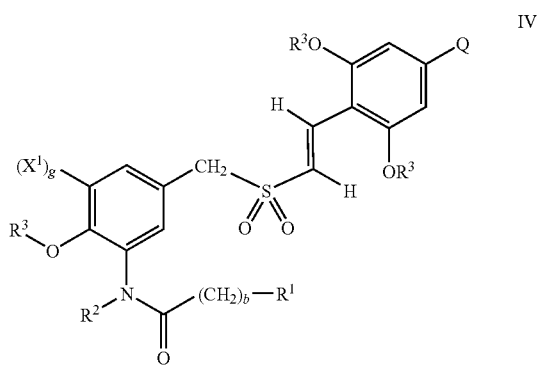

wherein:
X$^1$ is selected from the group consisting of (i), (ii) and (iii) below:

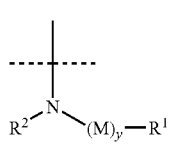

-continued

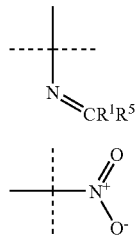
(ii)

(iii)

g is 0 or 1;
M is a bivalent connecting group selected from the group consisting of —(CH$_2$)$_a$—V—(CH$_2$)$_b$—, —(CH$_2$)$_d$—W—(CH$_2$)$_e$— and -Z-;
y is 1;
V is selected from the group consisting of —C(=O)—, —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3;
-Z- is

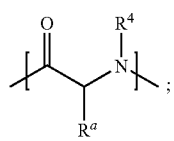

wherein the absolute stereochemistry of -Z- is either D or L; and
R$^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$;
wherein the substituents for the substituted aryl and substituted heterocyclic groups comprising or included within R$^a$ and R$^2$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;
or a salt of such a compound.

86. A compound according to claim 85, wherein g is 0; or a salt of such a compound.

87. A compound according to claim 86, which is (E)-2,4,6-trimethoxystyryl-3-(acetamido)-4-methoxybenzylsulfone.

88. A compound according to claim 83 wherein:
X is

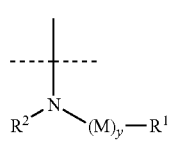
(i)

y is 1; and M is -Z-; or a salt of such a compound.

89. A compound according to claim 88, having the formula V:

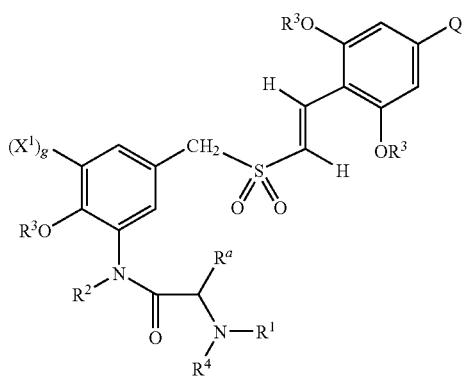

wherein:
X$^1$ is selected from the group consisting of (i), (ii) and (iii) below:

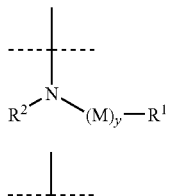
(i)

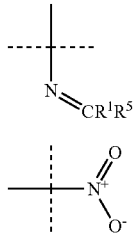
(ii)

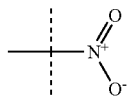
(iii)

g is 0 or 1;
M is a bivalent connecting group selected from the group consisting of —(CH$_2$)$_a$—V—(CH$_2$)$_b$—, —(CH$_2$)$_d$—W—(CH$_2$)$_e$— and -Z-;
y is 1;
V is selected from the group consisting of —C(=O), —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3; and
-Z- is

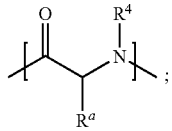

wherein the absolute stereochemistry of -Z- is either D or L; and wherein the substituents for the substituted aryl and substituted heterocyclic groups comprising or included within R$^a$ and R$^2$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

90. A compound according to claim 89, wherein g is 0; or a salt of such a compound.

91. A compound according to claim 83, wherein:
X is

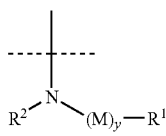

(i)

y is 1; M is —(CH$_2$)$_a$—V—(CH$_2$)$_b$—; and V is —SO$_2$—; or a salt of such a compound.

92. A compound according to claim 91, having the formula VI:

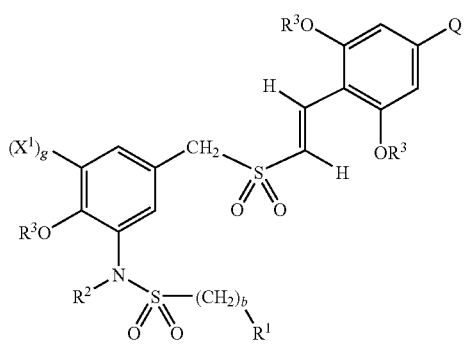

VI wherein:
X$^1$ is selected from the group consisting of (i), (ii) and (iii) below:

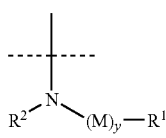

(i)

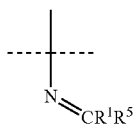

(ii)

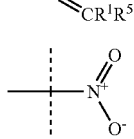

(iii)

g is 0 or 1;
M is a bivalent connecting group selected from the group consisting of —(CH$_2$)$_a$—V—(CH$_2$)$_b$—, —(CH$_2$)$_d$—W—(CH$_2$)$_e$— and -Z-;
y is 1;
V is selected from the group consisting of —C(=O)—, —C(=S)—, —S(=O)—, —SO$_2$—, —C(=O)NR$^4$—, —C(=S)NR$^4$— and —SO$_2$NR$^4$—;
W is selected from the group consisting of —NR$^4$—, —O— and —S—;
a is selected from the group consisting of 0, 1, 2 and 3;
each b is independently selected from the group consisting of 0, 1, 2 and 3;
d is selected from the group consisting of 1, 2 and 3;
e is selected from the group consisting of 0, 1, 2 and 3;
-Z- is

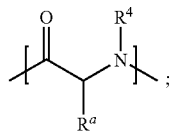

;

wherein the absolute stereochemistry of -Z- is either D or L; and

R$^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$;

wherein the substituents for the substituted aryl and substituted heterocyclic groups comprising or included within R$^a$ and R$^2$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

93. A compound according to claim 92, wherein g is 0; or a salt of such a compound.

94. A compound according to claim 80 having the formula IX:

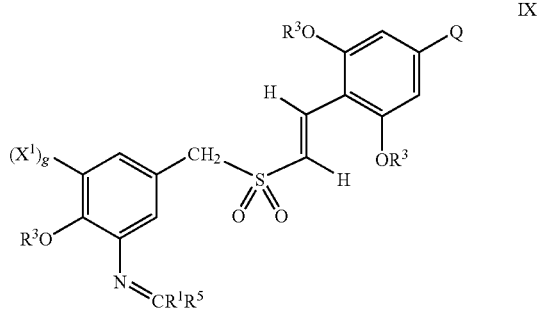

IX wherein:
X$^1$ is selected from the group consisting of (i), (ii) and (iii) below:

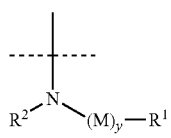

(i)

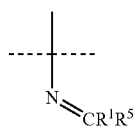

(ii)

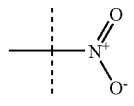

(iii)

g is 0 or 1;

M is a bivalent connecting group selected from the group consisting of —(CH$_2$)$_a$—V—(CH$_2$)$_b$—, —(CH$_2$)$_d$—W—(CH$_2$)$_e$— and -Z-;

y is 1;

V is selected from the group consisting of —C(=O)—, —C(=S)—, —S(=O)—, —SO$_2$—, —C(=O)NR$^4$—, —C(=S)NR$^4$— and —SO$_2$NR$^4$—;

W is selected from the group consisting of —NR$^4$—, —O— and —S—;

a is selected from the group consisting of 0, 1, 2 and 3;

b is selected from the group consisting of 0, 1, 2 and 3;

d is selected from the group consisting of 1, 2 and 3;

e is selected from the group consisting of 0, 1, 2 and 3;

-Z- is

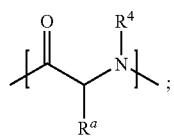

wherein the absolute stereochemistry of -Z- is either D or L;

R$^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and each R$^1$ is H;

wherein the substituents for the substituted aryl and substituted heterocyclic groups comprising or included within R$^a$ and R$^2$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4{}_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

95. A compound according to claim 94, wherein g is 0; or a salt of such a compound.

96. A compound according to claim 80 wherein:

X is (i)

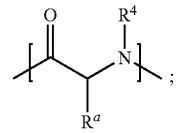

y is 1; M is —(CH$_2$)$_a$—V—(CH$_2$)$_b$—; and V is —C(=O)NR$^4$—; or, a salt of such a compound.

97. A compound according to claim 96 having the formula X:

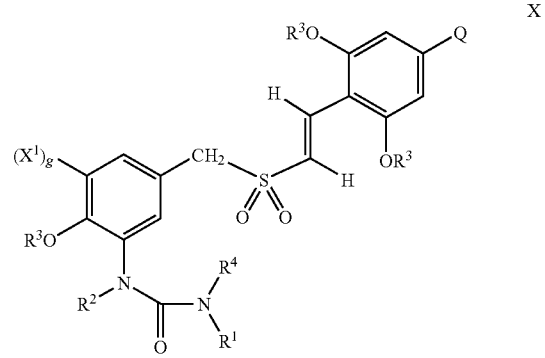

wherein:

X$^1$ is selected from the group consisting of (i), (ii) and (iii) below:

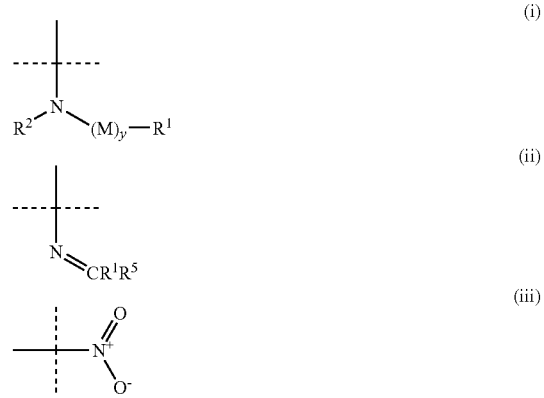

g is 0 or 1;

M is a bivalent connecting group selected from the group consisting of —(CH$_2$)$_a$—V—(CH$_2$)$_b$—, —(CH$_2$)$_d$—W—(CH$_2$)$_e$— and -Z-;

y is 1;

V is selected from the group consisting of —C(=O)—, —C(=S)—, —S(=O)—, —SO$_2$—, —C(=O)NR$^4$—, —C(=S)NR$^4$— and —SO$_2$NR$^4$—;

W is selected from the group consisting of —NR$^4$—, —O— and —S—;

a is selected from the group consisting of 0, 1, 2 and 3;

b is selected from the group consisting of 0, 1, 2 and 3;

d is selected from the group consisting of 1, 2 and 3;

e is selected from the group consisting of 0, 1, 2 and 3;

-Z- is

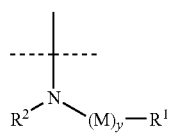

wherein the absolute stereochemistry of -Z- is either D or L; and

R$^a$ is selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$;

wherein the substituents for the substituted aryl and substituted heterocyclic groups comprising or included within R$^a$ and R$^2$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$;

or a salt of such a compound.

98. A compound according to claim 97, wherein g is 0; or a salt of such a compound.

99. A process for preparing a compound of claim 80 comprising:

(1) coupling a compound of formula IIIa:

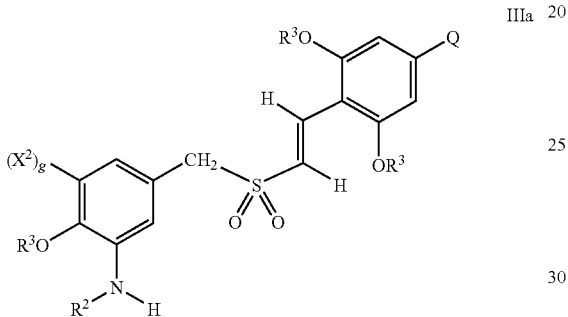

wherein:
X$^2$ is selected from the group consisting of —NO$_2$ and —NH$_2$, optionally protected with a chemical protecting group; and
g is 0 or 1;
or a salt of such a compound;
with a compound of formula XI:

R$^1$-A     XI wherein:
each R$^1$ is —H;
each R$^4$ is independently selected from the group consisting of —H, and —(C$_1$-C$_6$)alkyl;
each R$^5$ is independently selected from the group consisting of —H, —(C$_1$-C$_6$)alkyl and —(C$_1$-C$_6$)acyl;
wherein the substituents for the substituted aryl and substituted heterocyclic groups comprising or included within R$^a$ are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OR$^5$, —(C$_2$-C$_6$)alkylene-OH, phosphonato, —NR$^4$$_2$, —NHC(=O)(C$_1$-C$_6$)alkyl, sulfamyl, —OC(=O)(C$_1$-C$_3$)alkyl, —O(C$_2$-C$_6$)alkylene-N((C$_1$-C$_6$)alkyl)$_2$ and —CF$_3$; and
wherein A is a moiety containing an electrophilic reactive center, said moiety selected from the group consisting of:

(a) an alkyl moiety having a leaving group;
(b) an aryl halide or aryl pseudo halide;
(c) a carboxylic acid activated with a leaving group;
(d) a sulfonic acid activated with a leaving group;
(e) a carbamic acid moiety activated with a leaving group;
(f) a cyanate moiety;
(g) an aldehyde or ketone moiety, or a hydrate thereof or a ketal or acetal thereof;
(h) a carboxylic acid moiety and an amide coupling reagent; or
(i) the intermediate product of a thiourea moiety and 2-chloro-1-methyl pyridinium iodide;

to form a compound of formula Ia:

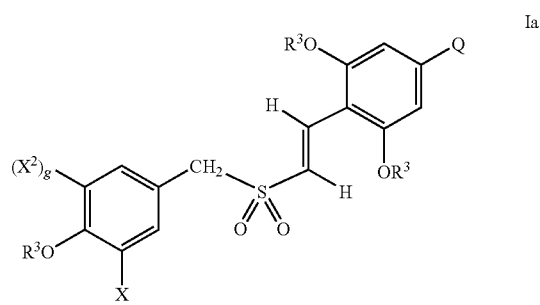

(2) optionally:

(a) when —X$^2$ is —NH$_2$ protected with a protecting group; removing said protecting group from —X$^2$ to yield a compound of formula Ib; or
(b) when —X$^2$ —NO$_2$, chemically reducing said —NO$_2$ to —NH$_2$;

to form a compound of formula Ib:

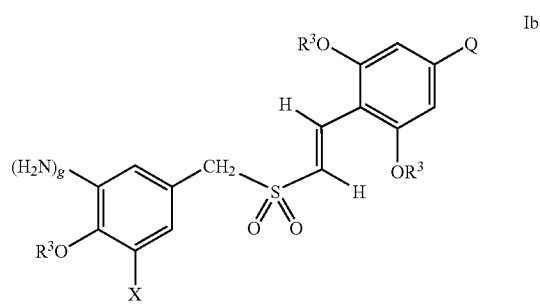

(3) optionally coupling said compound of formula Ib or a salt thereof: with a compound of formula XI:

R$^1$-A     XI wherein A is a moiety containing an electrophilic reactive center as defined above, to form a compound of formula I:

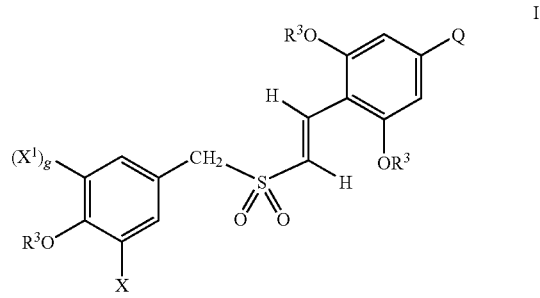

or a salt thereof.

100. A process according to claim 99 for preparing the compound of formula IIIa:

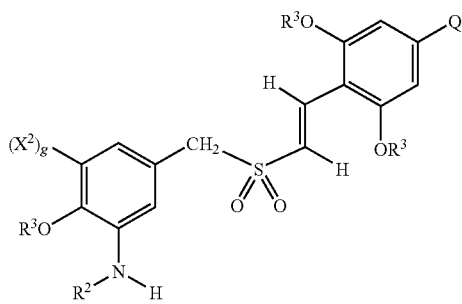

comprising: (1) chemically reducing a compound according to formula IIa:

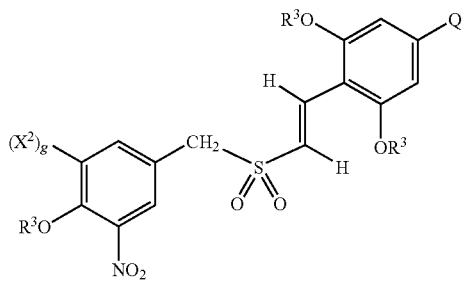

wherein
g is 0 or 1;
each $R^3$ is independently selected from —($C_1$-$C_6$)alkyl;
each $R^4$ is independently selected from the group consisting of —H, and —($C_1$-$C_6$) alkyl;
Q is selected from the group consisting of —H, —($C_1$-$C_6$) alkoxy, halogen, —($C_1$-$C_6$)alkyl and —$NR^4{}_2$; and
$X^2$ is selected from the group consisting of —$NO_2$ and —$NH_2$, optionally protected with a chemical protecting group, or a salt of such a compound, to form an aniline, or a salt thereof; and
(2) optionally alkylating the aniline with an alkylating reagent or by reductive amination, to form said compound of formula IIIa; or a salt thereof.

101. A process according to claim 100 wherein the compound of formula IIa is prepared by condensing a compound of formula D:

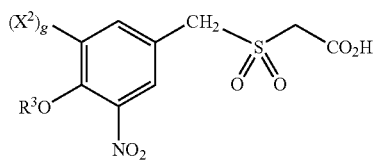

wherein:
each $R^3$ is independently selected from —($C_1$-$C_6$)alkyl; and
g is 0 or 1; and
$X^2$ is selected from the group consisting of —$NO_2$ and —$NH_2$, optionally protected with a chemical protecting group;

with a compound of formula E:

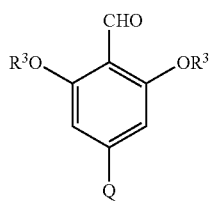

wherein:
each $R^3$ is independently selected from —($C_1$-$C_6$)alkyl; and
each $R^4$ is independently selected from the group consisting of —H, and —($C_1$-$C_6$)alkyl;
Q is selected from the group consisting of —H, —($C_1$-$C_6$) alkoxy, halogen, —($C_1$-$C_6$)alkyl and —$NR^4{}_2$; and salts thereof;
to form said compound of formula IIa; or a salt of such a compound.

102. A process according to claim 99, wherein the compound of formula IIIa is (E)-2,4,6-trimethoxystyryl-4-methoxy-3-aminobenzylsulfone, or a salt thereof.

103. A process according to claim 100, wherein the compound of formula IIIa is (E)-2,4,6-trimethoxystyryl-4-methoxy-3-aminobenzylsulfone, or a salt thereof.

104. A process for producing a compound according to claim 85 having the formula IV:

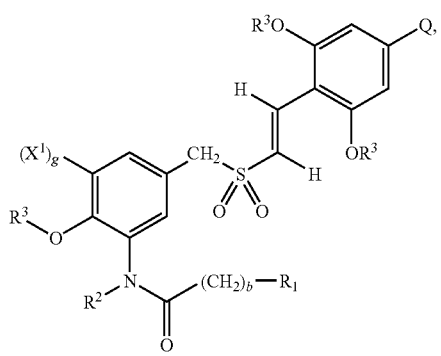

comprising,
(1) coupling a compound of formula IIIa:

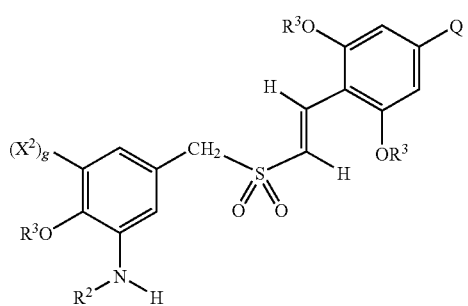

wherein:
g is 0 or 1;
and $X^2$ is selected from the group consisting of —$NO_2$ and —$NH_2$, optionally protected with a chemical protecting group; or a salt of such a compound;
with a compound of formula XII:

$$R^1-A^1 \qquad \text{XII}$$

wherein:
each $R^1$ is —H;
each $R^4$ is independently selected from the group consisting of —H, and —($C_1$-$C_6$)alkyl; and
each $R^5$ is independently selected from the group consisting of —H, —($C_1$-$C_6$)alkyl and —($C_1$-$C_6$)acyl;
wherein the substituents for the substituted aryl and substituted heterocyclic groups comprising or included within $R^2$ and $R^a$ are independently selected from the group consisting of halogen, ($C_1$-$C_6$)alkyl, —$NO_2$, —C≡N, —$CO_2R^5$, —C(=O)O($C_1$-$C_3$)alkyl, —$OR^5$, —($C_2$-$C_6$)alkylene-OH, phosphonato, —$NR^4{}_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$; and
$A^1$ is a carboxylic acid moiety with a leaving group, to form a compound of formula IVa:

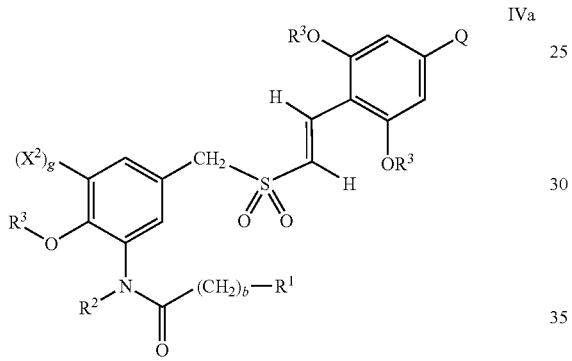

(2) optionally:
(a) when —$X^2$ is —$NH_2$ protected with a protecting group, removing said protecting group from —$X^2$ to yield a compound of formula IVb; or
(b) when —$X^2$ is —$NO_2$, chemically reducing said —$NO_2$ to —$NH_2$ to form a compound of formula IVb:

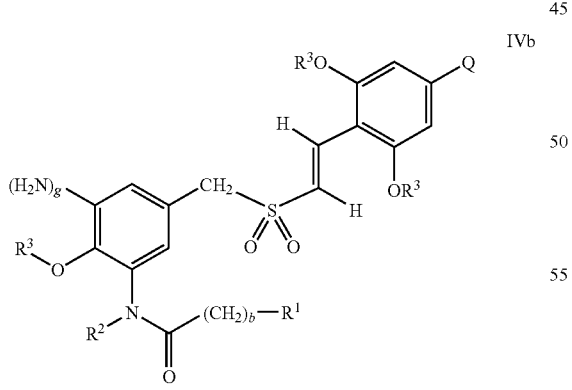

(3) optionally coupling said compound of formula IVb or a salt thereof with a compound of formula XI:

$$R^1-A \qquad \text{XI}$$

wherein A is a moiety containing an electrophilic reactive center;
to form said compound of formula IV or a salt thereof.

105. A process for producing a compound according to claim 89 having the formula V:

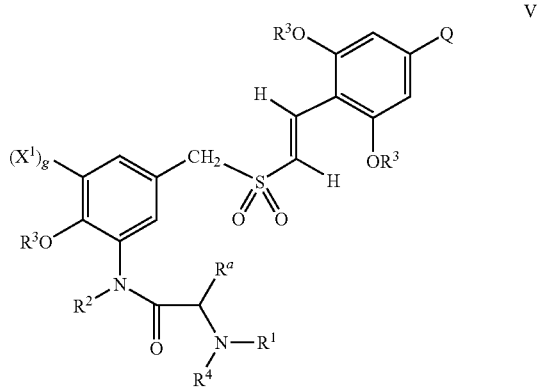

comprising:
(1) reacting a compound of formula IIIa:

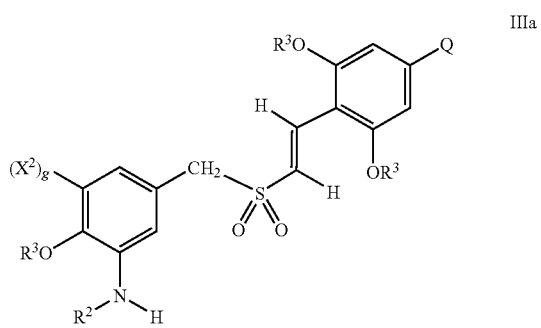

wherein:
g is 0 or 1;
and
$X^2$ is selected from the group consisting of —$NO_2$ and —$NH_2$, optionally protected with a chemical protecting group; or a salt of such a compound;
with
(a) a compound of formula XIII:

wherein:
each $R^a$ is independently selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, —($CH_2$)$_2$COOH, —$CH_2$-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$;
each $R^1$ is —H;
each $R^4$ is independently selected from the group consisting of —H, and —($C_1$-$C_6$)alkyl; and each $R^5$ is independently selected from the group consisting of —H, —$(C_1$-$C_6)$alkyl and —$(C_1$-$C_6)$acyl;

wherein the substituents for the substituted aryl and substituted heterocyclic groups comprising or included within $R^2$ and $R^a$ are independently selected from the group consisting of halogen, $(C_1$-$C_6)$alkyl, —$NO_2$, —C≡N, —$CO_2R^5$, —C(=O)O$(C_1$-$C_3)$alkyl, —$OR^5$, —$(C_2$-$C_6)$alkylene-OH, phosphonato, —$NR^4{}_2$, —NHC(=O)$(C_1$-$C_6)$alkyl, sulfamyl, —OC(=O)$(C_1$-$C_3)$alkyl, —O$(C_2$-$C_6)$alkylene-N$((C_1$-$C_6)$alkyl$)_2$ and —$CF_3$; and $A^2$ comprises an electrophilic moiety; and (b) an amide coupling reagent;

to form a compound of formula Va:

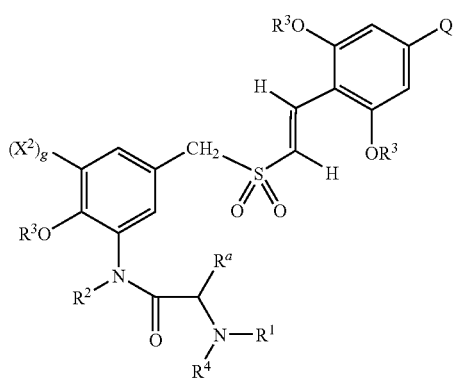

Va (2) optionally:
(a) when —$X^2$ is —$NH_2$ protected with a protecting group, removing said protecting group from —$X^2$ to yield a compound of formula Vb; or
(b) when —$X^2$ is —$NO_2$, chemically reducing said —$NO_2$ to —$NH_2$, to form a compound of formula Vb:

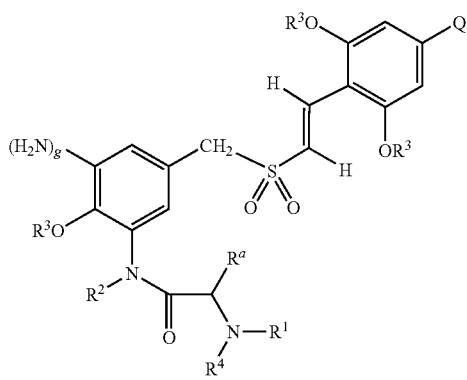

Vb (3) optionally coupling said compound of formula Vb or a salt thereof:

with a compound of formula XI:

$R^1$-A    XI wherein A is a moiety containing an electrophilic reactive center; to form said compound of formula V; or a salt thereof.

106. A process for producing a compound according to claim 92 having the formula VI:

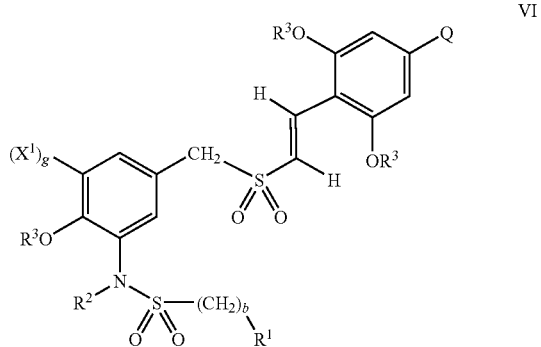

VI comprising, (1) coupling a compound of formula IIIa:

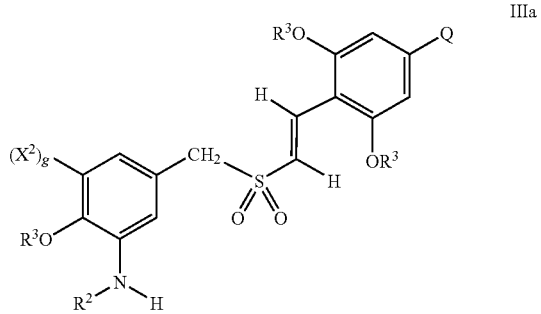

IIIa wherein:

g is 0 or 1;

and $X^2$ is selected from the group consisting of —$NO_2$ and —$NH_2$, optionally protected with a chemical protecting group; or a salt of such a compound;

with a compound of formula XIV:

$R^1$-$A^3$    XIV wherein:

each $R^1$ is —H;

each $R^4$ is independently selected from the group consisting of —H, and —$(C_1$-$C_6)$alkyl; and each $R^5$ is independently selected from the group consisting of —H, —$(C_1$-$C_6)$alkyl and —$(C_1$-$C_6)$acyl;

wherein the substituents for the substituted aryl and substituted heterocyclic groups comprising or included within $R^2$ and $R^a$ are independently selected from the group consisting of halogen, $(C_1$-$C_6)$alkyl, —$NO_2$, —C≡N, —$CO_2R^5$, —C(=O)O$(C_1$-$C_3)$alkyl, —$OR^5$, —$(C_2$-$C_6)$alkylene-OH, phosphonato, —$NR^4{}_2$, —NHC(=O)$(C_1$-$C_6)$alkyl, sulfamyl, —OC(=O)$(C_1$-$C_3)$alkyl, —O$(C_2$-$C_6)$alkylene-N$((C_1$-$C_6)$alkyl$)_2$ and —$CF_3$; and $A^3$ is a sulfonyl chloride moiety;

to form a compound of formula VIa:

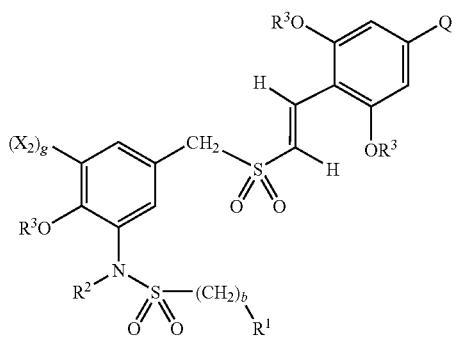

VIa (2) optionally:
  (a) when —$X^2$ is —$NH_2$ protected with a protecting group, removing said protecting group from —$X^2$ to yield a compound of formula VIb; or
  (b) when —$X^2$ is —$NO_2$, chemically reducing said —$NO_2$ to —$NH_2$, to form a compound of formula VIb:

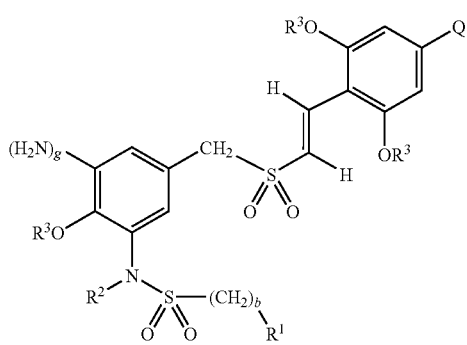

VIb (3) optionally coupling said compound of formula VIb or a salt thereof: with a compound of formula XI:

$R^1$-A     XI wherein A is a moiety containing an electrophilic reactive center;
to form said compound of formula VI.

107. A process for producing a compound according to claim 94 having the formula IX:

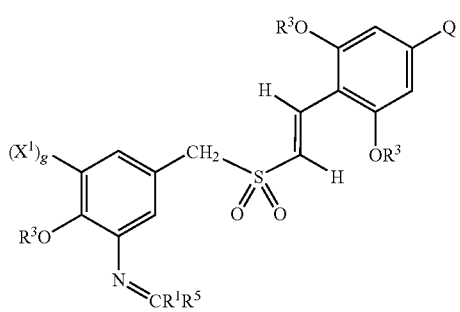

IX comprising;
(1) coupling a compound of formula IIIa:

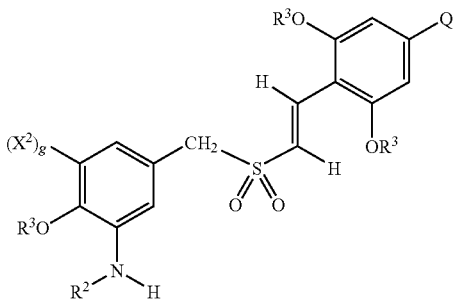

IIIa wherein:
  g is 0 or 1;
  and
  $X^2$ is selected from the group consisting of —$NO_2$ and —$NH_2$, optionally protected with a chemical protecting group; or a salt of such a compound; with a compound of formula XVII:

$R^1$-A     XVII wherein:
  each $R^1$ is —H;
  each $R^4$ is independently selected from the group consisting of —H, and —($C_1$-$C_6$)alkyl; and
  each $R^5$ is independently selected from the group consisting of —H, —($C_1$-$C_6$)alkyl and —($C_1$-$C_6$)acyl;
  wherein $A^6$ comprises an aldehyde or ketone moiety, or a hydrate thereof or a ketal or acetal thereof;
to form a compound of formula IXa:

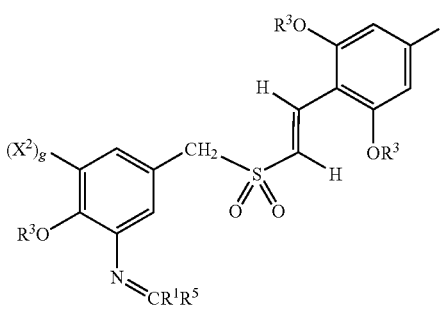

IXa (2) optionally:
  (a) when —$X^2$ is —$NH_2$ protected with a protecting group, removing said protecting group from —$X^2$ to yield a compound of formula IXb; or
  (b) when —$X^2$ is —$NO_2$, chemically reducing said —$NO_2$ to —$NH_2$, to form a compound of formula IXb:

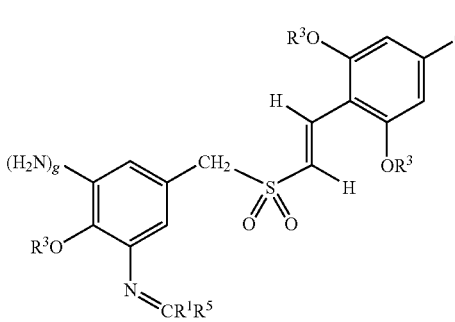

IXb (3) optionally coupling said compound of formula IXb or a salt thereof: with a compound of formula XI:

R¹-A  XI wherein A is a moiety containing an electrophilic reactive center; to form said compound of formula IX; or a salt thereof.

108. A process for producing a compound according to claim 97 having the formula X:

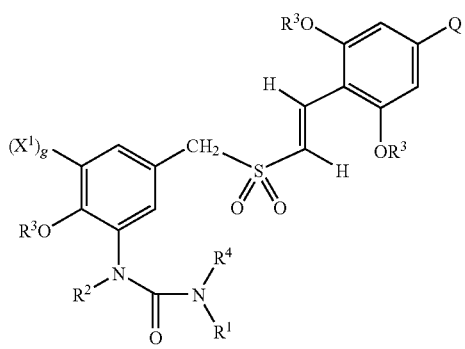

comprising;
(1) coupling a compound of formula IIIa:

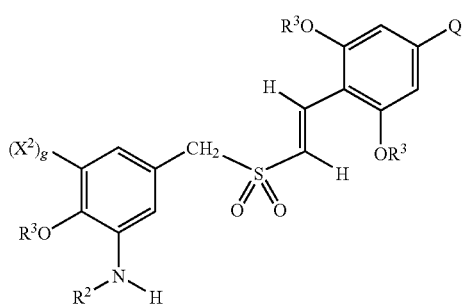

wherein:
g is 0 or 1; and
$X^2$ is selected from the group consisting of —$NO_2$ and —$NH_2$, optionally protected with a chemical protecting group; or a salt of such a compound;
with a compound of formula XVIII:

R¹-A⁷  XVIII wherein:
each $R^1$ is —H;
each $R^4$ is independently selected from the group consisting of —H, and —($C_1$-$C_6$)alkyl; and
each $R^5$ is independently selected from the group consisting of —H, —($C_1$-$C_6$)alkyl and —($C_1$-$C_6$)acyl;
wherein:
(a) if $A^7$ is a cyanate moiety, then
$R^1$ is —H; and
and $R^4$ is —H; and
(b) if $A^7$ is a carbamic acid moiety activated with a leaving group, then $R^1$ and $R^4$ of formula X are as defined above;

to form a compound of formula Xa:

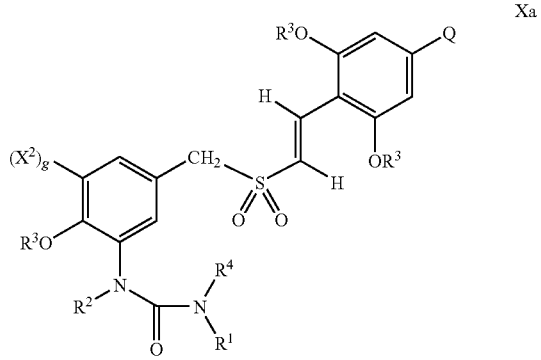

(2) optionally:
(a) when —$X^2$ is —$NH_2$ protected with a protecting group, removing said protecting group from —$X^2$ to yield a compound of formula Xb; or
(b) when —$X^2$ is $NO_2$, chemically reducing said —$NO_2$ to —$NH_2$; to form a compound of formula Xb:

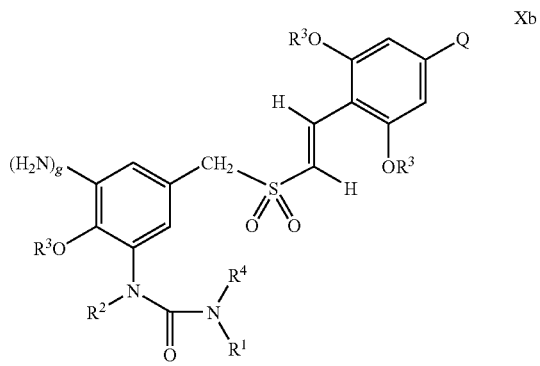

(3) optionally coupling said compound of formula Xb or a salt thereof: with a compound of formula XI:

R¹-A  XI wherein A is a moiety containing an electrophilic reactive center; to form said compound of formula X; or a salt thereof.

109. A conjugate of the formula, I-L-Ab; wherein I is a compound according to claim 80, Ab is an antibody; and -L- is a single covalent bond or a linking group covalently linking said compound to said antibody.

110. A conjugate of the formula, I-L-Ab; wherein I is a compound according to claim 83;1 Ab is an antibody; and -L- is a single covalent bond or a linking group covalently linking said compound to said antibody.

111. A conjugate according to claim 109 or 110 wherein said antibody Ab is a monoclonal antibody or a monospecific polyclonal antibody.

112. A conjugate according to claim 111 wherein said antibody Ab is a tumor-specific antibody.

113. A pharmaceutical composition comprising a pharmaceutically acceptable carrier and at least one compound according to claim 80, or a pharmaceutically acceptable salt of such a compound.

114. A pharmaceutical composition comprising a pharmaceutically acceptable carrier and at least one compound according to claim 83, or a pharmaceutically acceptable salt of such a compound.

115. A pharmaceutical composition comprising a pharmaceutically acceptable carrier and at least one conjugate according to claim 109 or claim 110.

116. A pharmaceutical composition comprising a pharmaceutically acceptable carrier and at least one conjugate according to claim 111.

117. A method of treating an individual for a cancer selected from the group consisting of breast, prostate, lung and colorectal cancers comprising administering to said individual in need of such treatment an effective amount of at least one compound according to claim 80, or a pharmaceutically acceptable salt of such a compound.

118. A method of inducing apoptosis of tumor cells in an individual afflicted with a cancer selected from the group consisting of breast, prostate, lung and colorectal cancers, comprising administering to said individual an effective amount of at least one compound according to claim 80, or a pharmaceutically acceptable salt of such a compound.

119. A method of inducing apoptosis of tumor cells in an individual afflicted with a cancer selected from the group consisting of breast, prostate, lung and colorectal cancers, comprising administering to said individual an effective amount of at least one compound according to claim 83, or a pharmaceutically acceptable salt of such a compound.

120. A method of treating an individual afflicted with a cancer selected from the group consisting of breast, prostate, lung and colorectal cancers, comprising administering to said individual an effective amount of at least one conjugate according to any one of claims 109 or 110.

121. A compound according to claim 90 selected from the group consisting of:
- (E)-2,4,6-trimethoxystyryl-3-amino-4-methoxybenzyl-sulfone-L-lysineamide;
- (E)-2,4,6-trimethoxystyryl-3-amino-4-methoxybenzyl-sulfone-L-serineamide; and
- (E)-2,4,6-trimethoxystyryl-3-amino-4-methoxybenzyl-sulfone-D-serineamide; or a salt of such a compound.

122. A compound according to claim 98 which is (E)-2,4,6-trimethoxystyryl-3-(ureido)-4-methoxybenzylsulfone, or a salt thereof.

* * * * *

UNITED STATES PATENT AND TRADEMARK OFFICE
CERTIFICATE OF CORRECTION

| | | |
|---|---|---|
| PATENT NO. | : 7,598,232 B2 | Page 1 of 1 |
| APPLICATION NO. | : 10/506005 | |
| DATED | : October 6, 2009 | |
| INVENTOR(S) | : Reddy et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 651 days Delete the phrase "by 651 days" and insert -- by 1,139 days --

Signed and Sealed this

Twenty-seventh Day of July, 2010

David J. Kappos
*Director of the United States Patent and Trademark Office*